(12) United States Patent
Raja et al.

(10) Patent No.: US 9,242,010 B2
(45) Date of Patent: Jan. 26, 2016

(54) LIVING COPOLYMER-PROTEIN/PEPTIDE HYBRIDS FOR BIOMEDICAL APPLICATIONS

(75) Inventors: Krishnaswami Raja, Staten Island, NY (US); Wei Shi, Staten Island, NY (US); Sukanta Dolai, Staten Island, NY (US); Saadyah Averick, Staten Island, NY (US); William L'Amoreaux, Freehold, NJ (US); Probal Banerjee, Staten Island, NY (US)

(73) Assignee: Research Foundation of The City University of New York, New York, NY (US)

( * ) Notice: Subject to any disclaimer, the term of this patent is extended or adjusted under 35 U.S.C. 154(b) by 869 days.

(21) Appl. No.: 12/992,854

(22) PCT Filed: May 18, 2009

(86) PCT No.: PCT/US2009/044371
§ 371 (c)(1),
(2), (4) Date: Jul. 5, 2011

(87) PCT Pub. No.: WO2009/140683
PCT Pub. Date: Nov. 19, 2009

(65) Prior Publication Data
US 2011/0262991 A1  Oct. 27, 2011

Related U.S. Application Data

(60) Provisional application No. 61/054,077, filed on May 16, 2008.

(51) Int. Cl.
| | |
|---|---|
| A61K 38/00 | (2006.01) |
| A61K 31/74 | (2006.01) |
| A61K 47/48 | (2006.01) |
| A61K 49/00 | (2006.01) |
| A61K 49/08 | (2006.01) |
| A61K 49/12 | (2006.01) |

(52) U.S. Cl.
CPC ......... *A61K 47/4823* (2013.01); *A61K 47/4813* (2013.01); *A61K 47/48215* (2013.01); *A61K 47/48246* (2013.01); *A61K 49/0032* (2013.01); *A61K 49/0054* (2013.01); *A61K 49/0056* (2013.01); *A61K 49/085* (2013.01); *A61K 49/12* (2013.01)

(58) Field of Classification Search
None
See application file for complete search history.

(56) References Cited

U.S. PATENT DOCUMENTS

| | | | |
|---|---|---|---|
| 4,264,466 A | 4/1981 | Carleton et al. | |
| 5,466,747 A * | 11/1995 | Rolando et al. | 525/54.1 |
| 5,554,501 A * | 9/1996 | Coassin et al. | 506/9 |
| 5,672,334 A | 9/1997 | Ranney et al. | |
| 5,948,763 A | 9/1999 | Soto-Jara et al. | |
| 2005/0267221 A1 | 12/2005 | Wellen | |
| 2007/0207180 A1 | 9/2007 | Tanihara et al. | |
| 2007/0258889 A1 | 11/2007 | Douglas et al. | |
| 2008/0290321 A1 * | 11/2008 | Charreyre et al. | 252/301.35 |
| 2010/0316631 A1 * | 12/2010 | Safavy | 424/133.1 |

FOREIGN PATENT DOCUMENTS

WO     WO0064486 A1 * 11/2000 ............. A61K 47/48

OTHER PUBLICATIONS

Bures et al., Surface modifications and molecular imprinting of polymers in medical and pharmaceutical applications, J. of Controlled Release, 72 (2001) 25-33.*
Lowik et al., Synthesis of Bio-Inspired Hybrid Polymers Using Peptide Synthesis and Protein Engineering, Adv. Polym. Sci (2006) 202:19-52.*
Veronese & Pasut, PEGylation, successful approach to drug delivery, Drug Discovery Today, vol. 10, No. 21, Nov. 2005, 1451-1458.*
Bioconjugate Techniques, Greg T. Hermanson, Academic Press (1996 and/or 2008 versions, referenced by Applicant).*

* cited by examiner

*Primary Examiner* — Karlheinz R Skowronek
*Assistant Examiner* — Joseph Fischer
(74) *Attorney, Agent, or Firm* — Hoffmann & Baron, LLP

(57) ABSTRACT

Water soluble polymers having formula I: $Y-(L^1)_{n1}-(C(O))_{n2}-(R^1)_{n3}-R^2$ are claimed. The polymers may contain multiple water soluble, immunogenicity reducing moieties and multiple active moieties. The polymers may be linked to a protein, or a peptide having up to twelve amino acids.

25 Claims, 63 Drawing Sheets

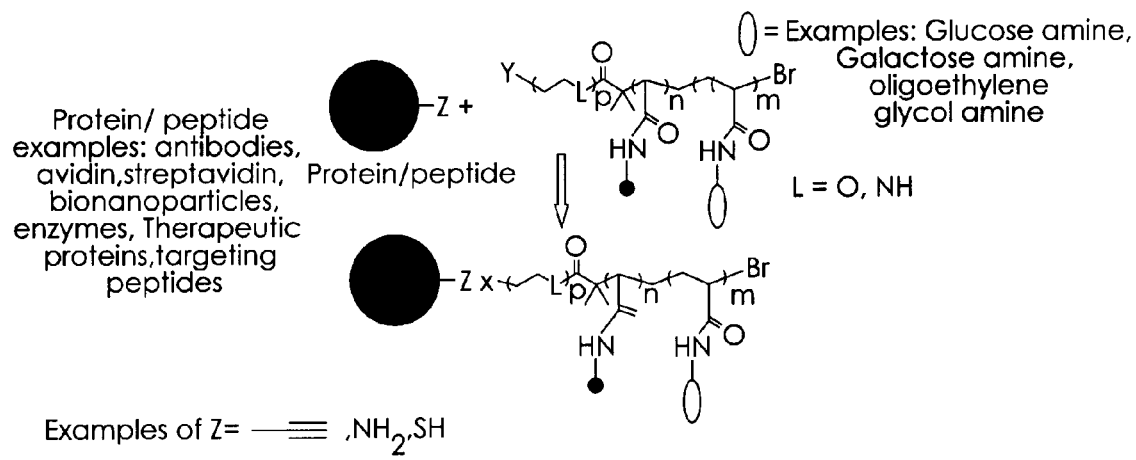
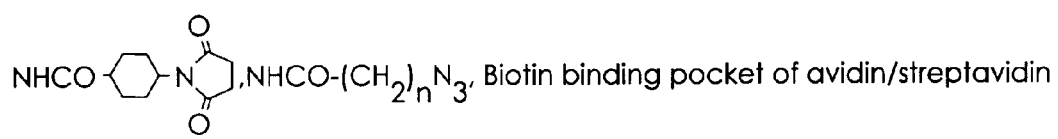
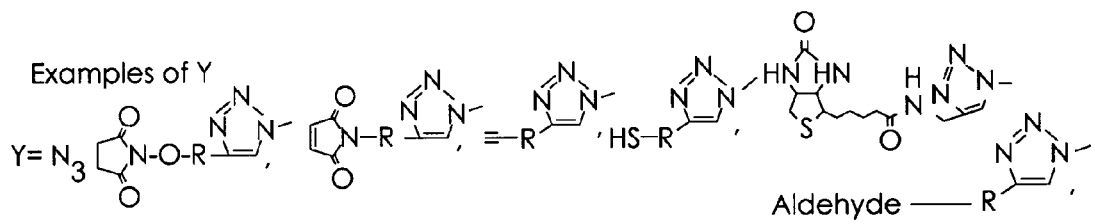
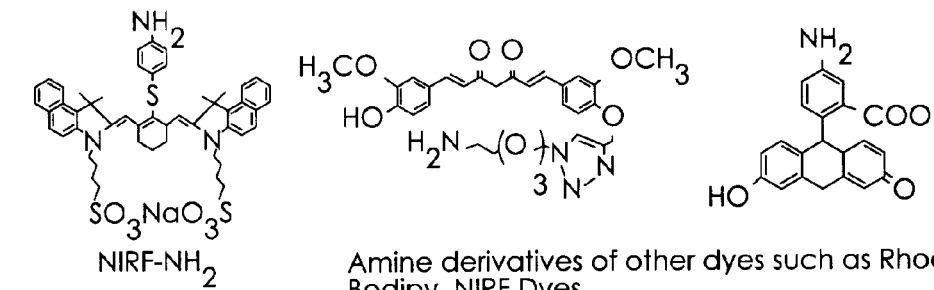
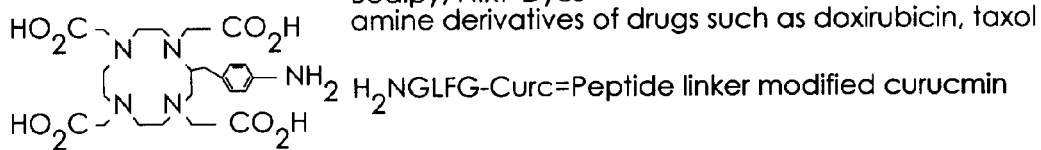
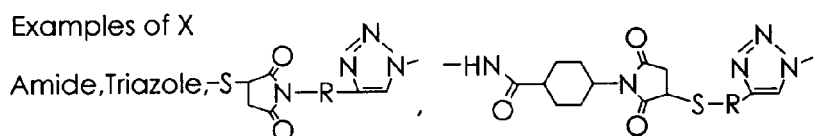
FIG. 7

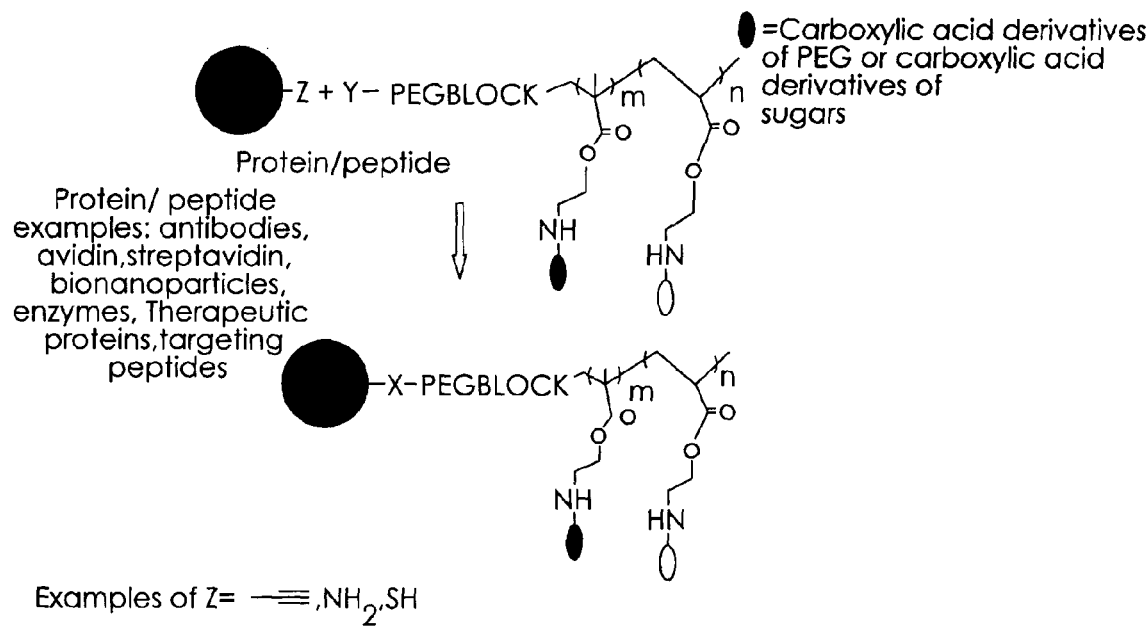
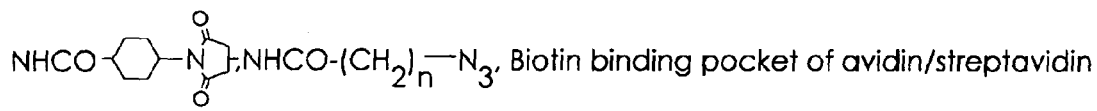
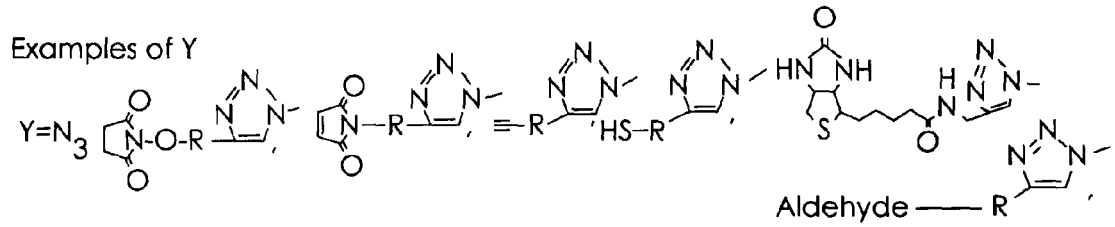
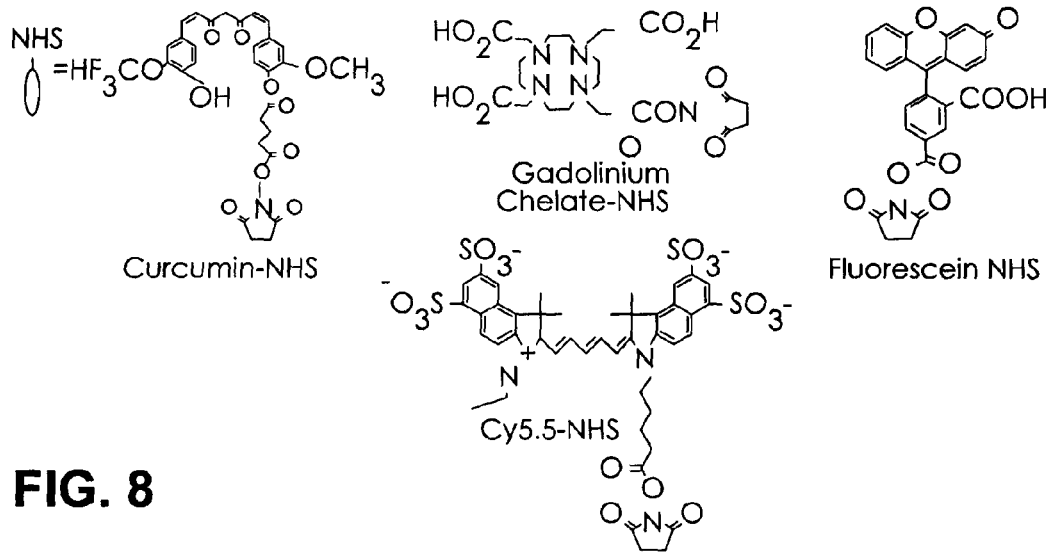
FIG. 8

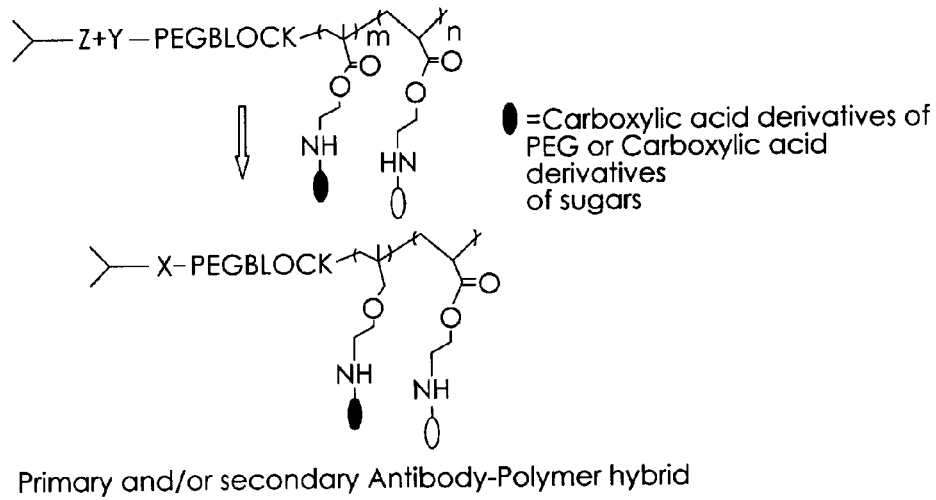
Primary and/or secondary Antibody-Polymer hybrid
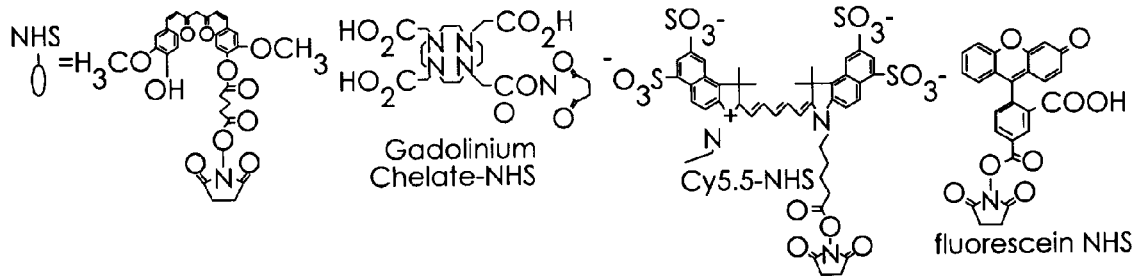
Carboxylic acid and N-hydroxysuccinimide dervatives of other dyes or drugs such as rhodamine Bodipy, Taxol doxirubicin, peptide modified curcumin
Example of $Z= SH, NH_2$, $NHCO-(CH_2)_n$
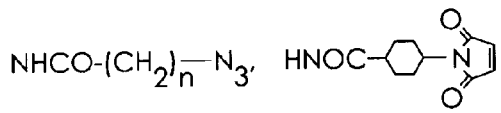
Examples of Y
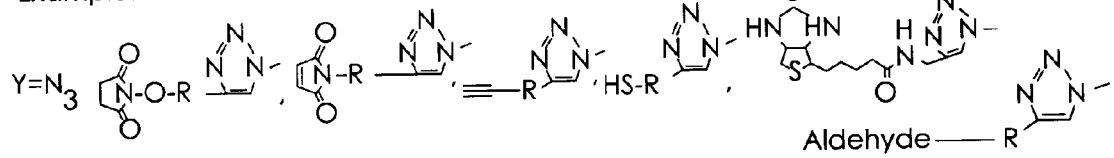
R= Linker Examples: aliphatic, aromatic, chromophoric, cyclic non-aromatic
FIG. 9

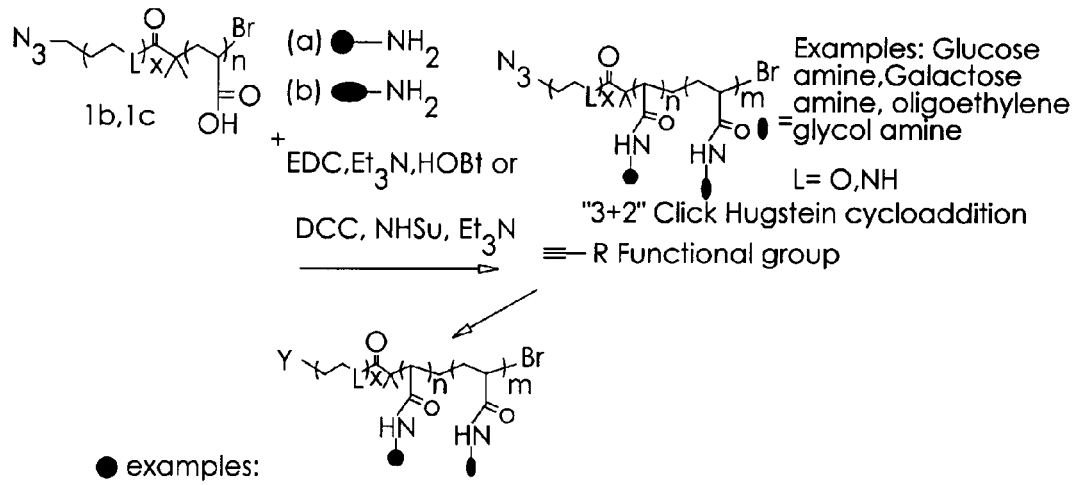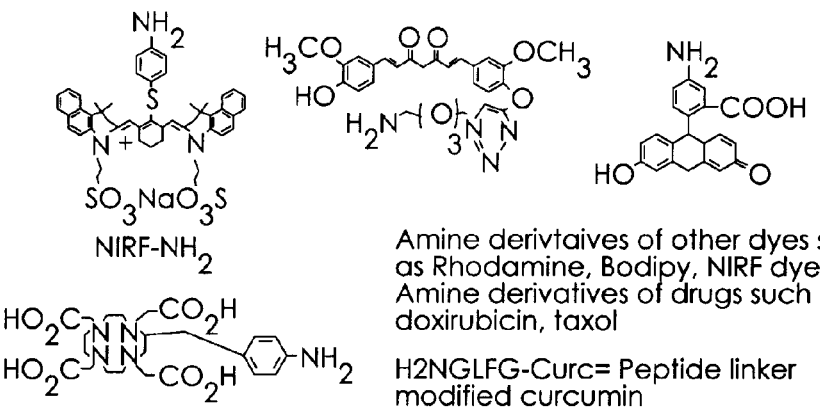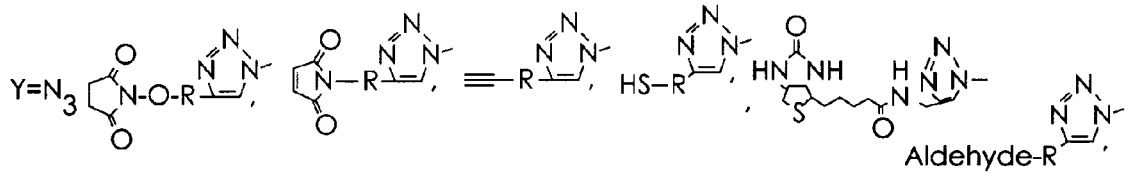
FIG. 14

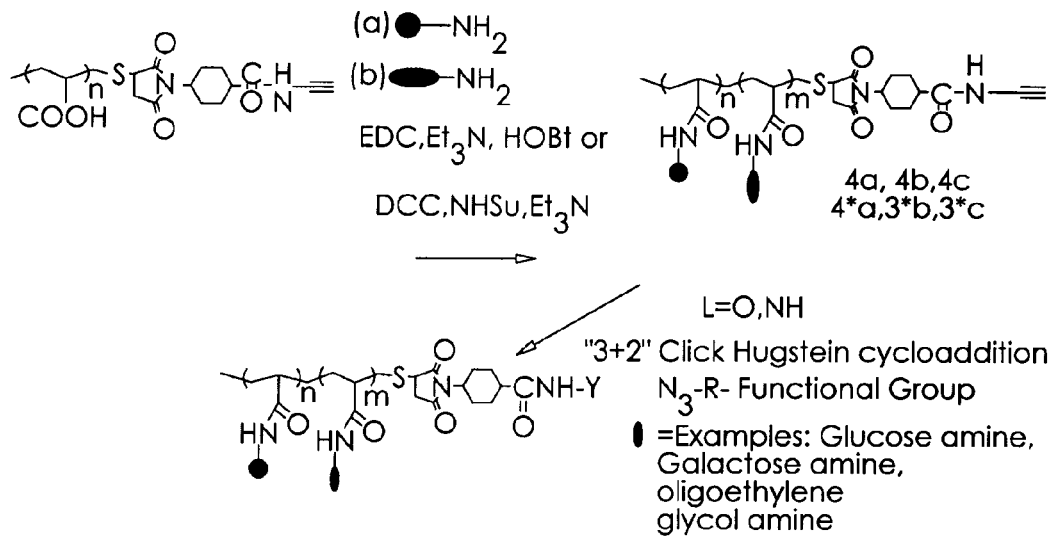

Examples of ≡—R—Functional Group

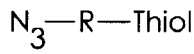   
   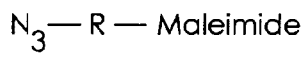

R= Linker Examples: aliphatic, aromatic, chromophoric, cyclic non-aromatic

Examples of Y

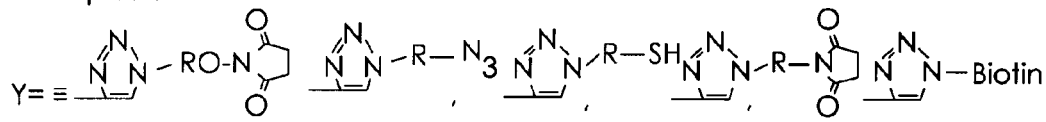

R= Linker Examples: aliphatic, aromatic, chromophoric, cyclic non-aromatic

● Examples:

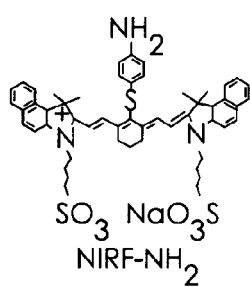

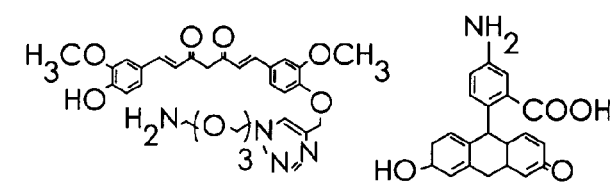

Amine derivtaives of other dyes such as Rhodamine, Bodipy, NIRF dyes
Amine derivatives of drugs such as doxirubicin, taxol

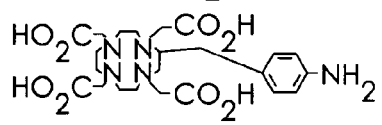

H2NGLFG-Curc= Peptide linker modified curcumin

FIG. 16

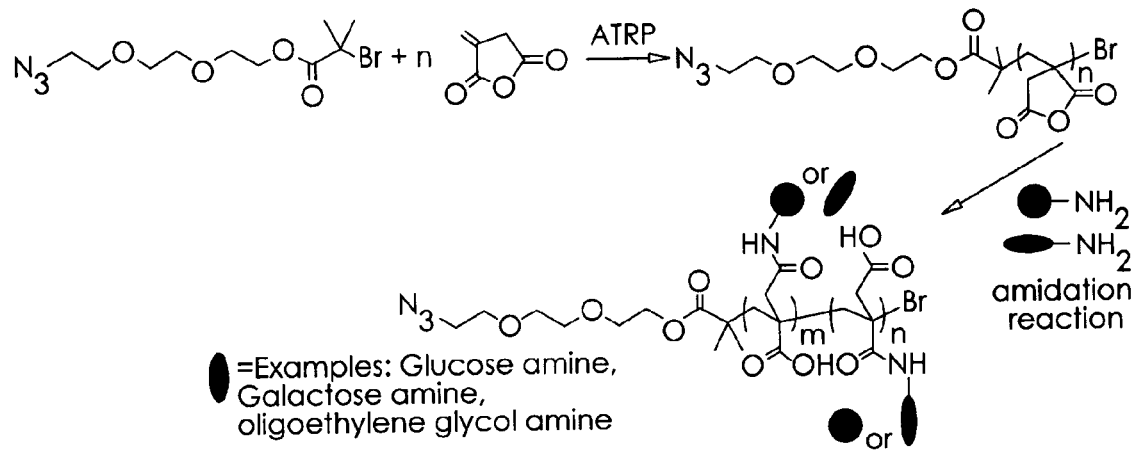
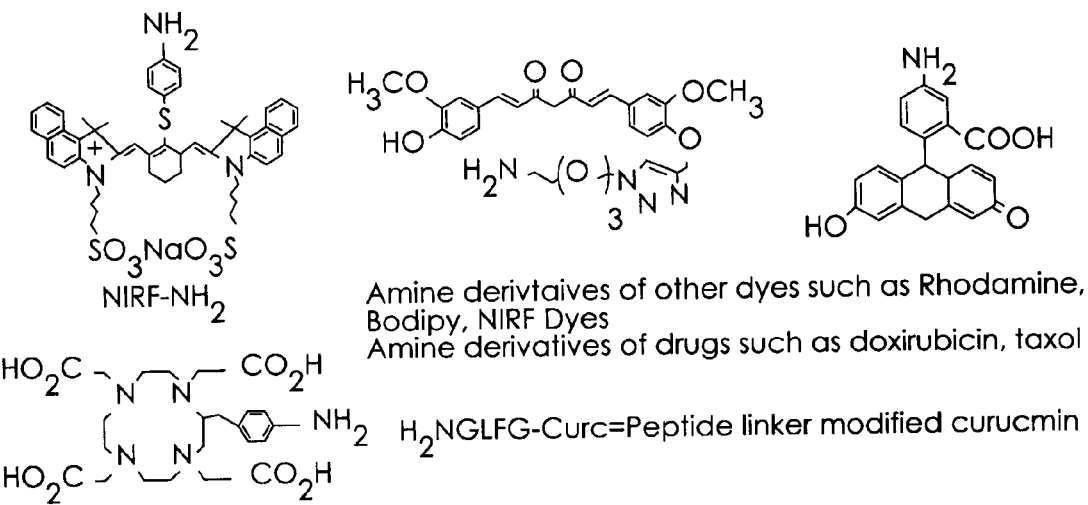
FIG. 20

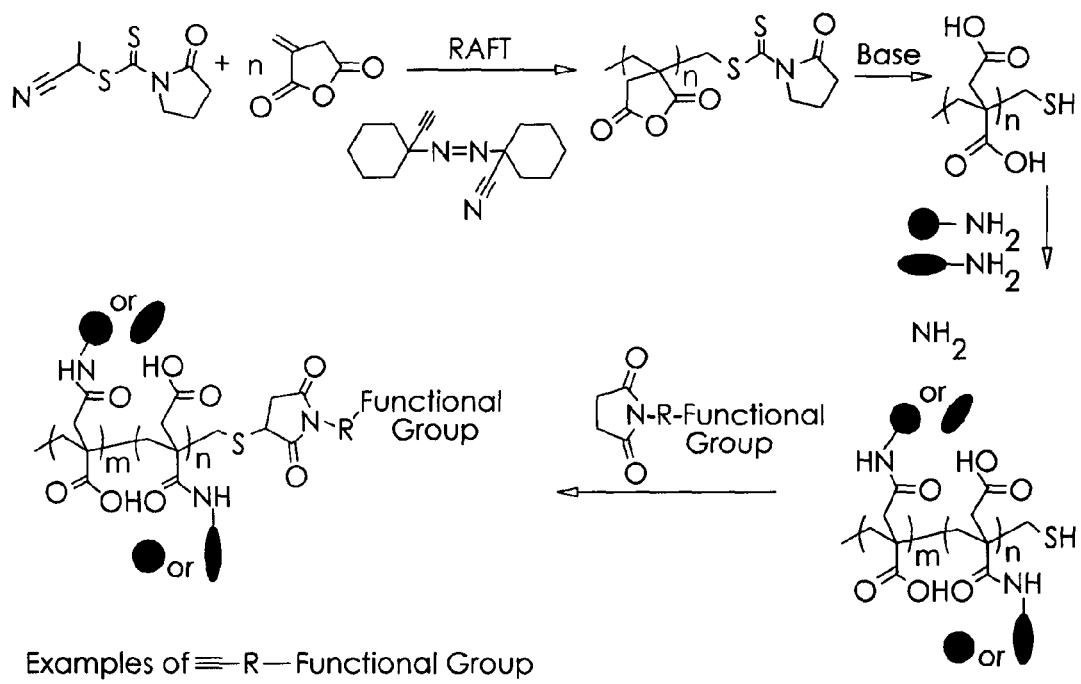

Examples of ≡—R—Functional Group

≡—R—Thiol   ≡—R—N Hydroxy succinimide

≡—R—Maleimide   ≡—R—≡   ≡—R—Maleimide

≡—R— Biotin   No Reagent

R= Linker Examples: aliphatic, aromatic, chromophoric, cyclic non-aromatic

● =Examples: Glucose amine, Galactose amine, oligoethylene glycol amine

● Examples:

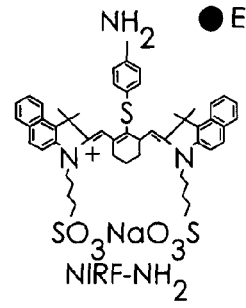

NIRF-NH$_2$

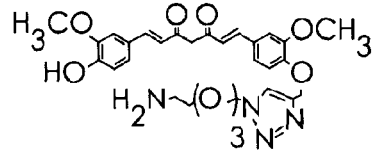

Amine derivtaives of other dyes such as Rhodamine, Bodipy, NIRF Dyes
Amine derivatives of drugs such as doxirubicin, taxol

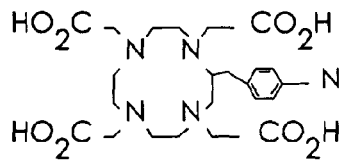

H$_2$NGLFG-Curc=Peptide linker modified curucmin

FIG. 21

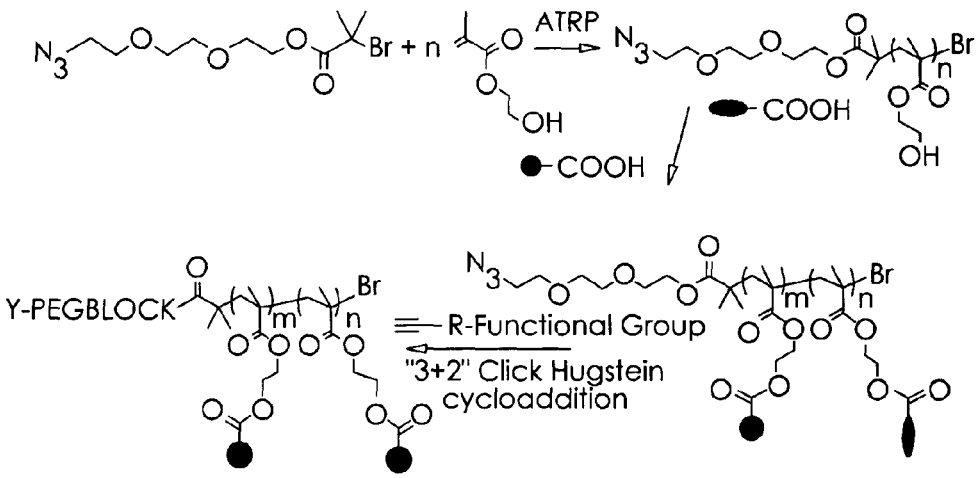
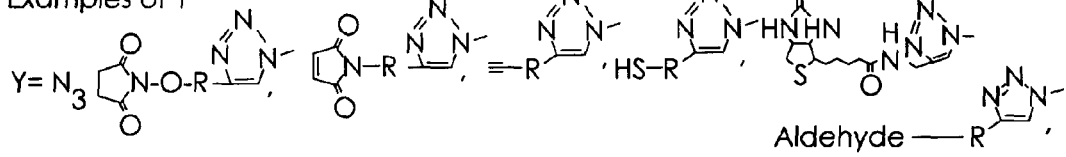
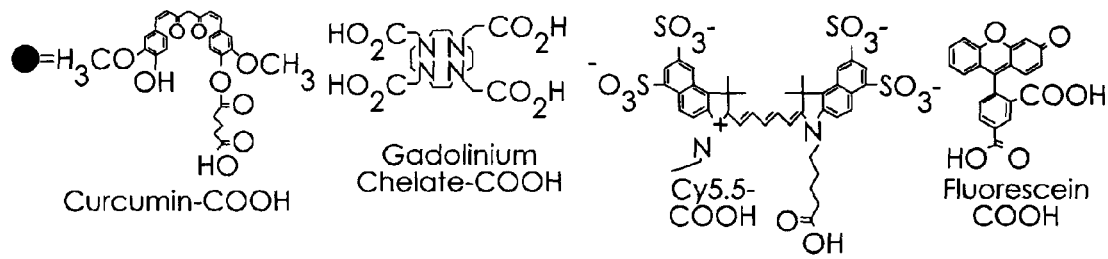
Carboxylic acid and N-Hydroxysuccinimde dervatives of other dyes or drugs such as rhodamine Bodipy, Taxol doxirbicin, peptide modified curcumin
FIG. 22

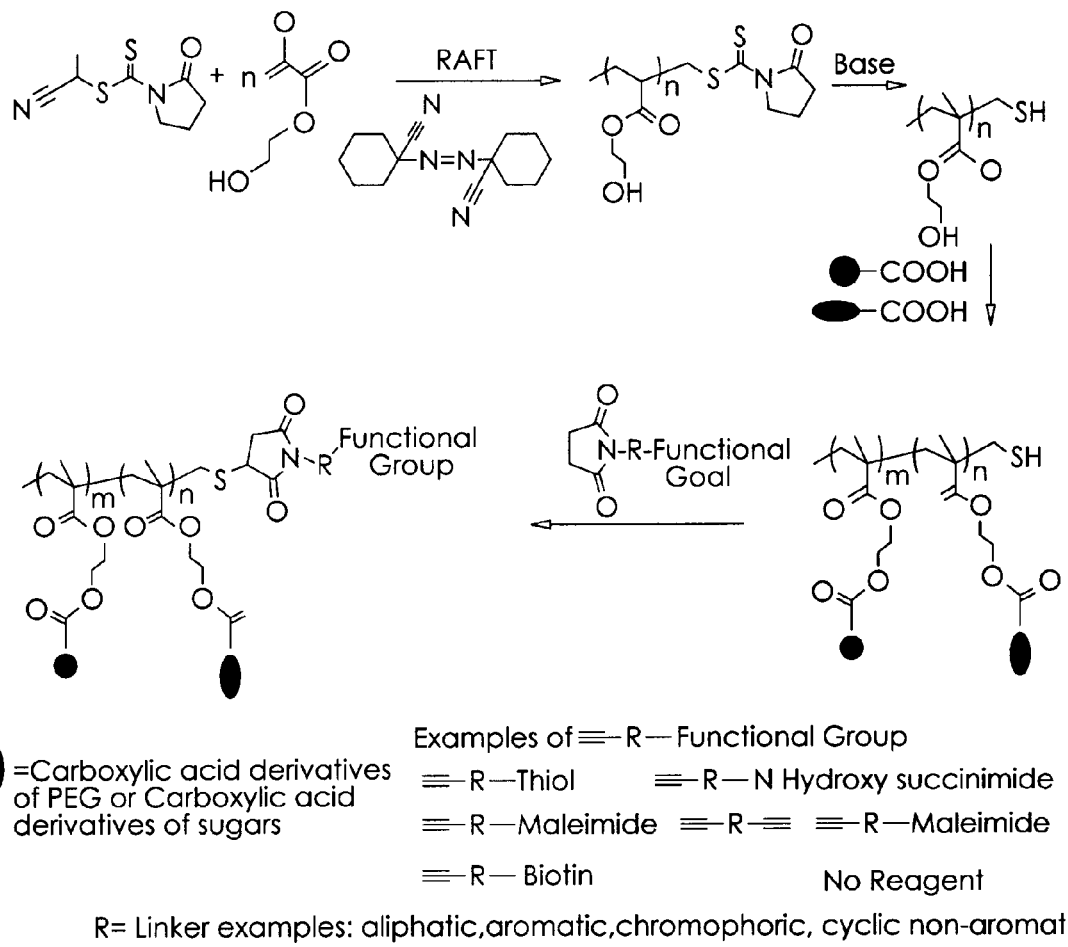
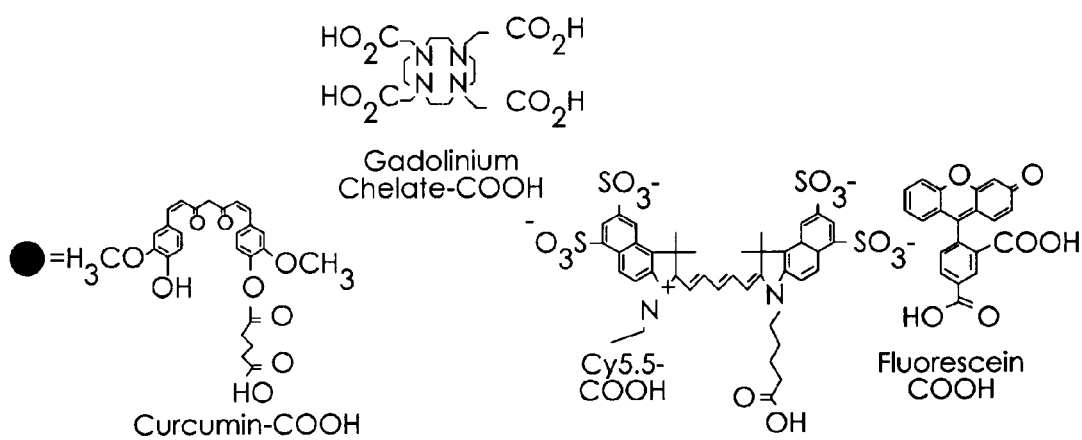
FIG. 23

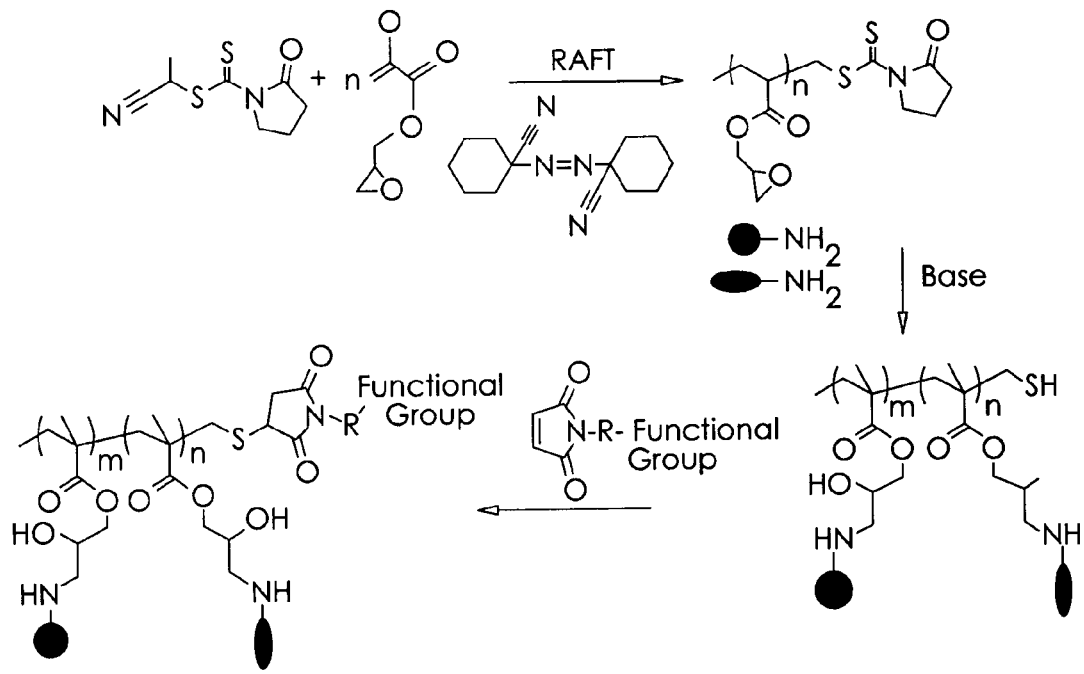

● =Examples: Glucose amine, Galactose amine, oligoethylene glycol amine

Examples of ≡–R—Functional Group
≡–R—Thiol    ≡–R—N Hydroxy succinimide
≡–R—Maleimide  ≡–R–≡  ≡–R—Maleimide
≡–R— Biotin        No Reagent R= Linker examples: aliphatic, aromatic, chromophoric, cyclic non-aromatic ● Examples:

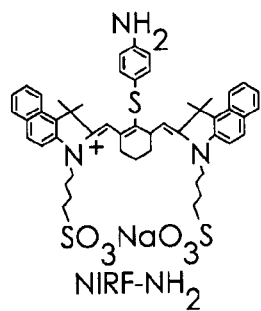
NIRF-NH$_2$

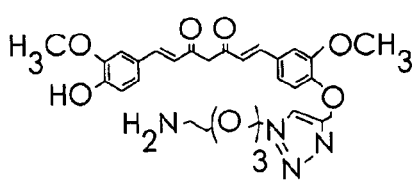

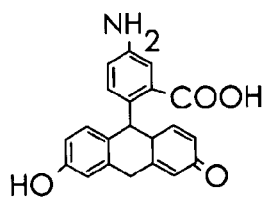

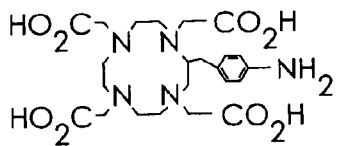

Amine derivtaives of other dyes such as Rhodamine, Bodipy, NIRF Dyes
Amine derivatives of drugs such as doxirubicin, taxol
H$_2$NGLFG-Curc=Peptide linker modified curucmin

FIG. 24

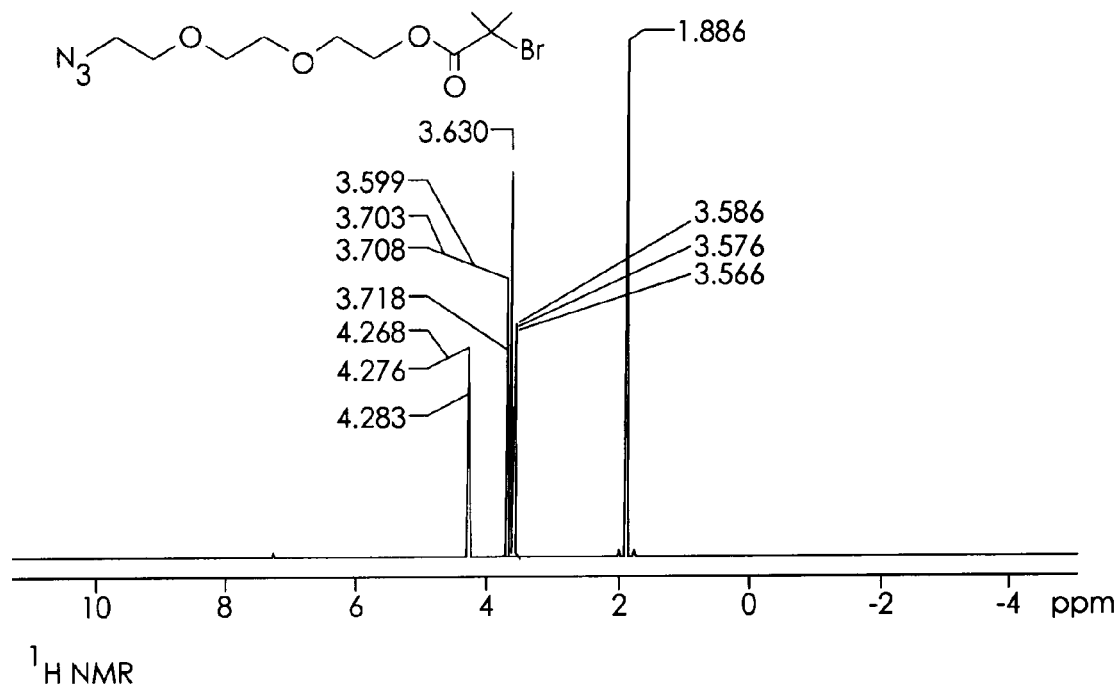
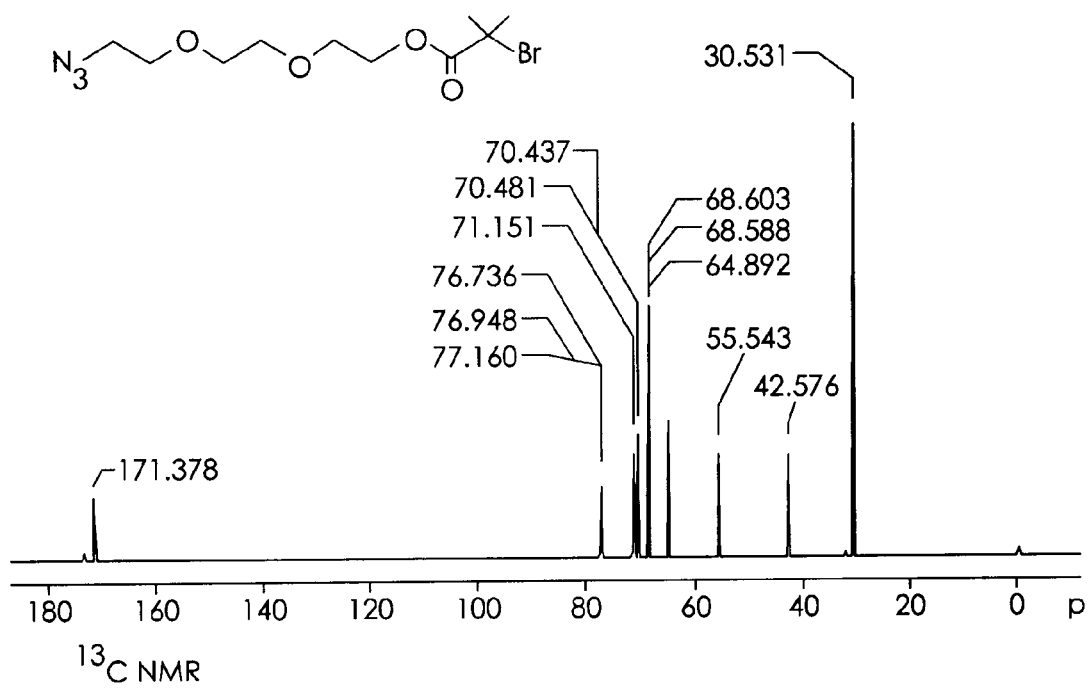
FIG. 26

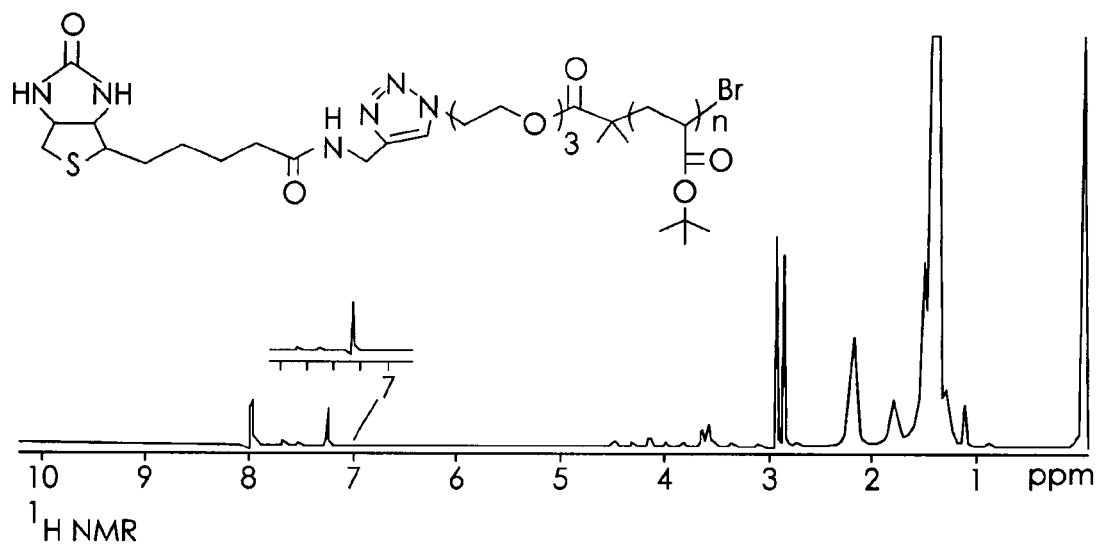
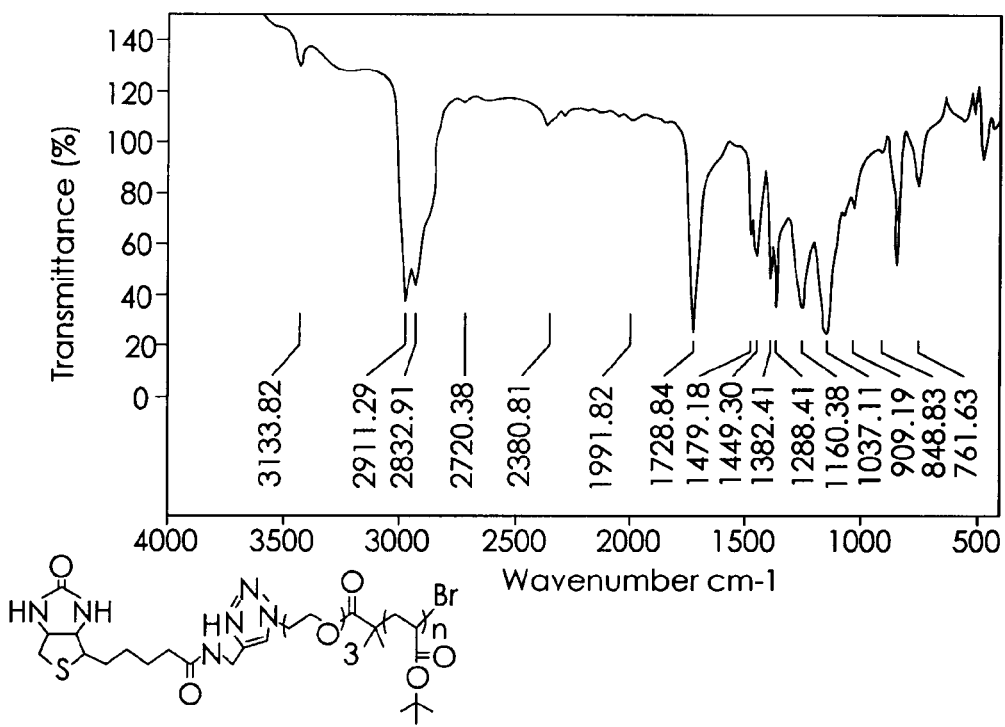
FIG. 31

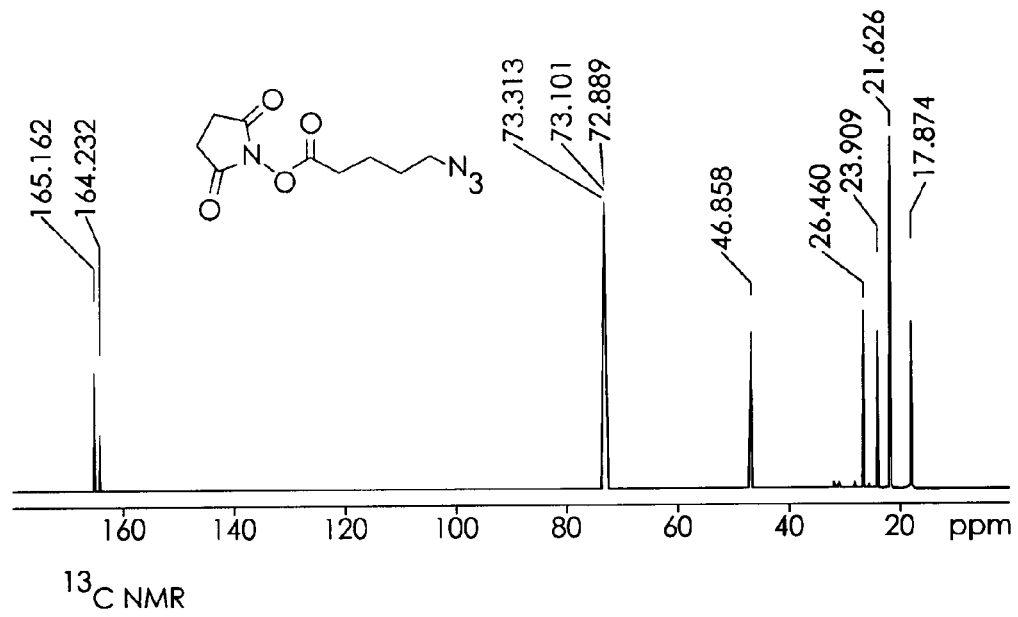
$^{13}$C NMR
FIG. 50
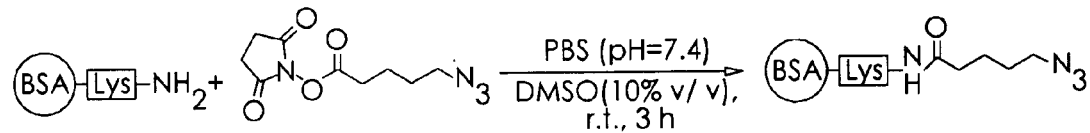
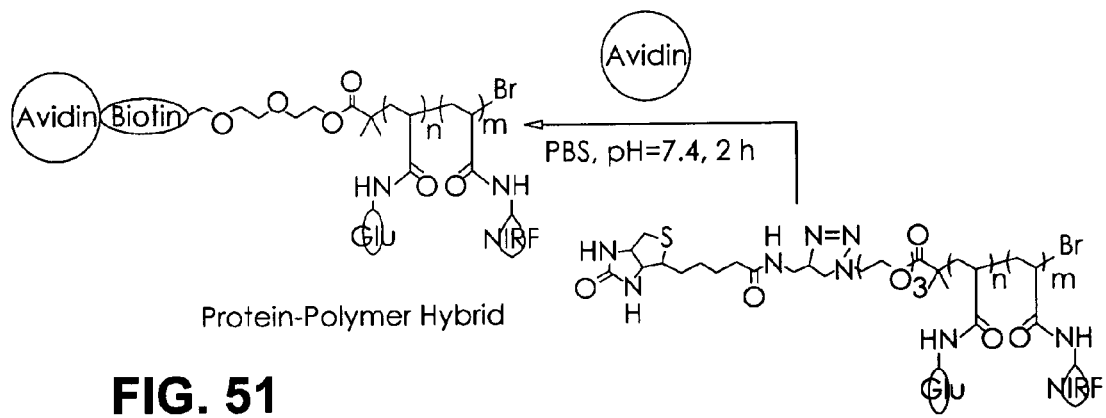
FIG. 51

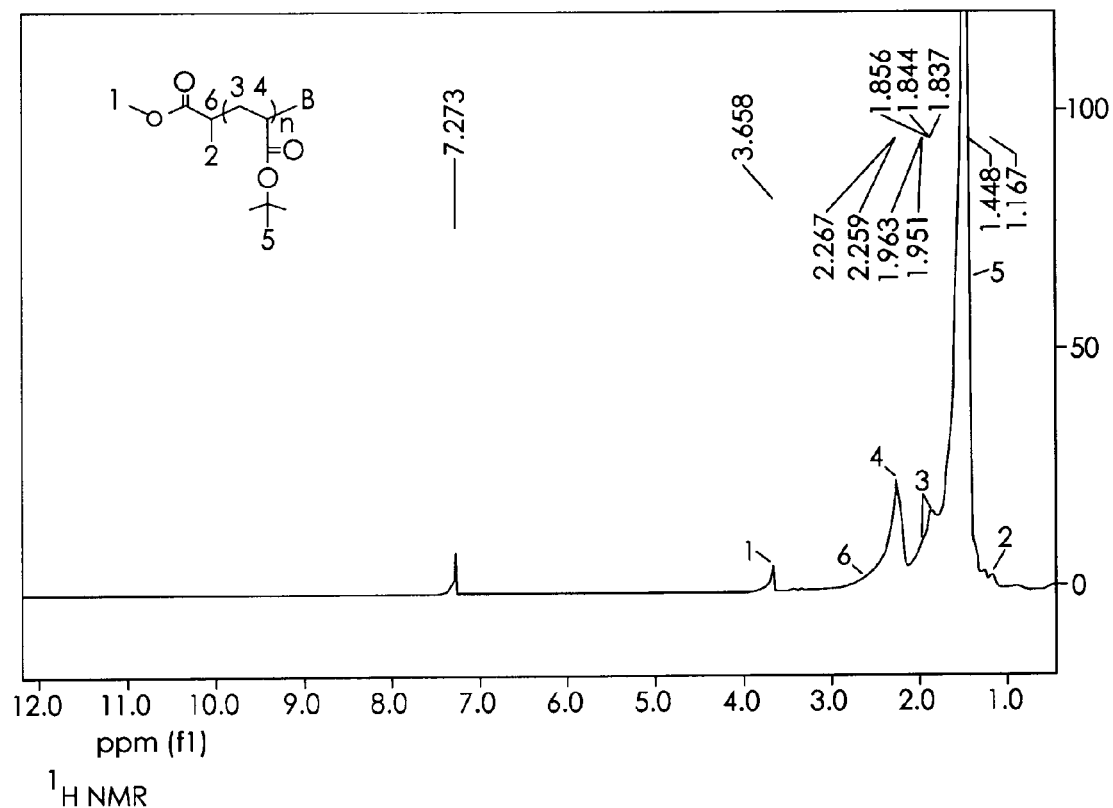
¹H NMR
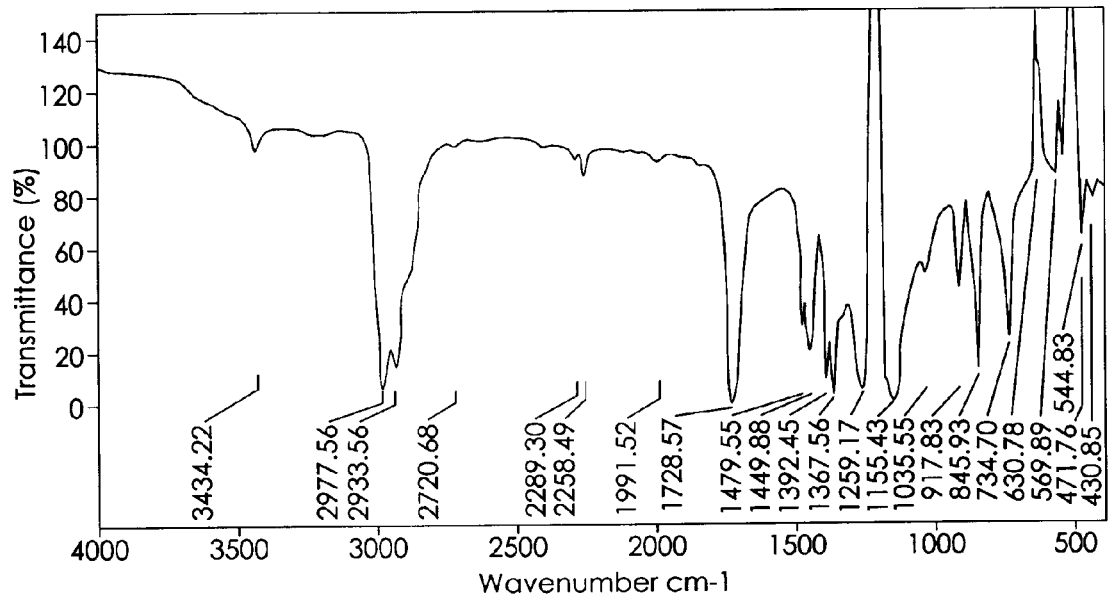
FTIR
FIG. 53

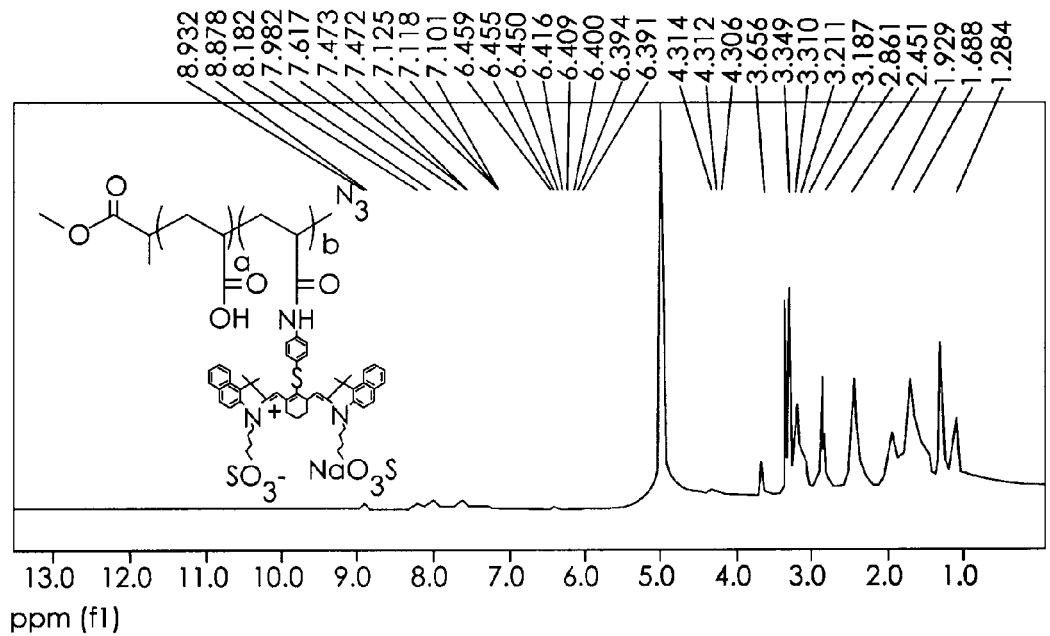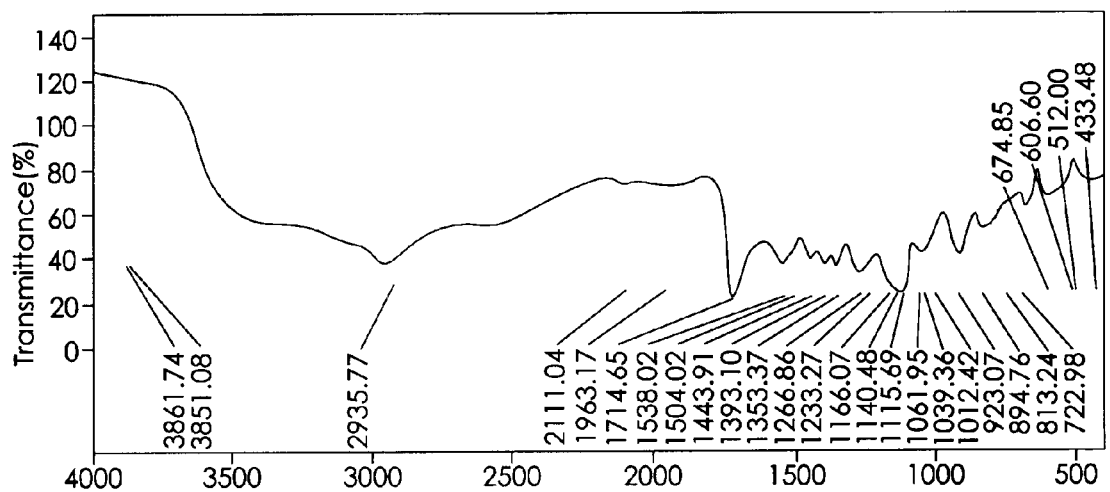
FIG. 56

LIVING COPOLYMER-PROTEIN/PEPTIDE HYBRIDS FOR BIOMEDICAL APPLICATIONS

CROSS-REFERENCE TO RELATED APPLICATION

This application claims the benefit of U.S. Provisional Application No. 61/054,077, filed on May 16, 2008, which is incorporated herein by reference.

BACKGROUND OF THE INVENTION

The synthesis of well defined polymer-protein/peptide hybrids is a rich and newly emerging field of research. These hybrid materials have potential applications in medical, biopharmaceutical and other life science areas [1-5]. Until very recently, the synthesis of polymer protein hybrids has been largely restricted to conjugates in which the synthetic polymer component is either poly(ethylene glycol) (PEG) or poly (N-isopropyl acrylamide). PEGylation increases the proteolytic stability, reduces the immunogenicity and enhances the plasma half life of proteins [1]. Some PEGylated proteins are approved drugs, for example, PEGASYS™ (PEGylated interferon α-2α) marketed by Roche is used to treat hepatitis C, a liver disease caused by the hepatitis C virus.

The synthesis of copolymer-protein hybrid materials has been so far restricted to a few acrylate/methacrylate monomers due to; (a) the difference in solubility between monomers: for instance, the preparation of a copolymer containing a monosaccharide derived acrylate (hydrophilic) and taxol acrylate (hydrophobic) would be very challenging (b) widely different reactivity between monomers (c) the lack of reactivity of many biologically relevant molecules, for example the acrylate of the anti-cancer and Anti Alzheimer's drug candidate curcumin could be synthesized but cannot be polymerized via free radical polymerization methods because the molecule is a radical scavenger.

SUMMARY OF THE INVENTION

A water soluble polymer having the formula:

$$Y\text{-}(L^1)_{n1}\text{-}(C(O))_{n2}\text{---}(R^1)_{n3}\text{---}R^2 \quad \text{I}$$

wherein:
Y represents a coupling group suitable for coupling the polymer to a protein comprising a complementary coupling group;
$L^1$ represents a linking moiety that results from the polymerization process:
n1 represents 0 or 1;
n2 represents 0 or 1;
$R^1$ independently represents:

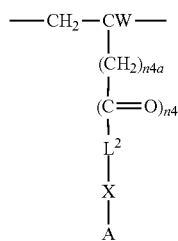

W independently represents —H, —$CH_3$, —COOH, or —$CH_2COOH$;

n4a independently represents 0 or 1
n4 independently represents 0 or 1;
$L^2$ independently represents a linker having the formula: -$(J)_{n5}$-$(R)_{n6}$—
wherein:
J represents —O— or —NH—;
R represents:
(i) $C_1$-$C_{12}$ alkyl optionally substituted with one or more hydroxyl or oxo substituents, and wherein one or more carbon atoms in the alkyl chain is optionally substituted with a heteroatom selected from the group consisting of —O—, —S—, and —NH—; (ii) phenyl or biphenyl, (iii) a carbocyclic non-aromatic ring having 5-7 carbon atoms; (iv) an aromatic heterocyclic ring having five or six atoms wherein at least one of the ring carbon atoms is substituted by a heteroatom selected from the group consisting of O, S, or NH, and (v) a non-aromatic heterocyclic ring having 5-7 carbon atoms wherein at least one of the ring carbon atoms is substituted by a heteroatom selected from the group consisting of O, S, or NH;
n5 independently represents 0 or 1;
n6 independently represents 0-6;
X independently represents a coupled group that results from reacting a coupling group and a complementary coupling group;
A represents $(A^1)_n$ and $(A^2)_m$;
$A^1$ independently represents a water soluble, immunogenicity reducing moiety;
$A^2$ independently represents an active moiety;
n and m independently represent 2 to about 500;
n3 represents n+m; and
$R^2$ represents H, an a straight chain or branched alkyl group having 1-6 carbon atoms, Cl or Br,
wherein the polymer is water soluble.

DESCRIPTION OF DRAWINGS

FIG. 7 (Scheme 1) shows a representation of polymer-peptide/protein hybrids in which the polymer component is derived by attaching amine derivatives of dyes/drugs to polymers bearing side chain carboxylic acid groups.

FIG. 8 (Scheme 2) shows the synthesis of polymer protein hybrids in which the polymer component is derived by attaching carboxylic acid and/or N-Hydroxysuccinimide derivatives of dyes/drugs to polymers bearing amine side groups.

FIG. 9 (Scheme 3) shows antibody-copolymer hybrid conjugates.

FIG. 14 (Scheme 8) shows a synthesis of copolymers based on side chain carboxylic acid prepolymers.

FIG. 16 (Scheme 11) shows a synthesis of side chain copolymers with reactive chain ends based on RAFT.

FIG. 20 (Scheme 15) shows a synthesis of polyitaconic anhydride via ATRP.

FIG. 21 (Scheme 16) shows a synthesis of polyitaconic anhydride via RAFT.

FIG. 22 (Scheme 17) shows a synthesis of poly 2-hydroxyethyl acrylate via ATRP.

FIG. 23 (Scheme 18) shows a synthesis of poly 2-hydroxyethyl acrylate via RAFT.

FIG. 24 (Scheme 19) shows a synthesis of polyglycidyl methacrylate via RAFT.

FIGS. 25 and 26 show $^1$H NMR and $^{13}$C NMR.

FIGS. 30, 46, 48, and 50 show $^{13}$C NMR.

FIGS. 31, 53, and 56 show $^1$H NMR and FTIR.

FIG. 51 (top) shows reaction scheme for Example 15. FIG. 51 (bottom) shows reaction scheme for Example 16.

FIG. 67 (bottom) shows a reaction scheme for Example 31.

DETAILED DESCRIPTION

Figure 1A:
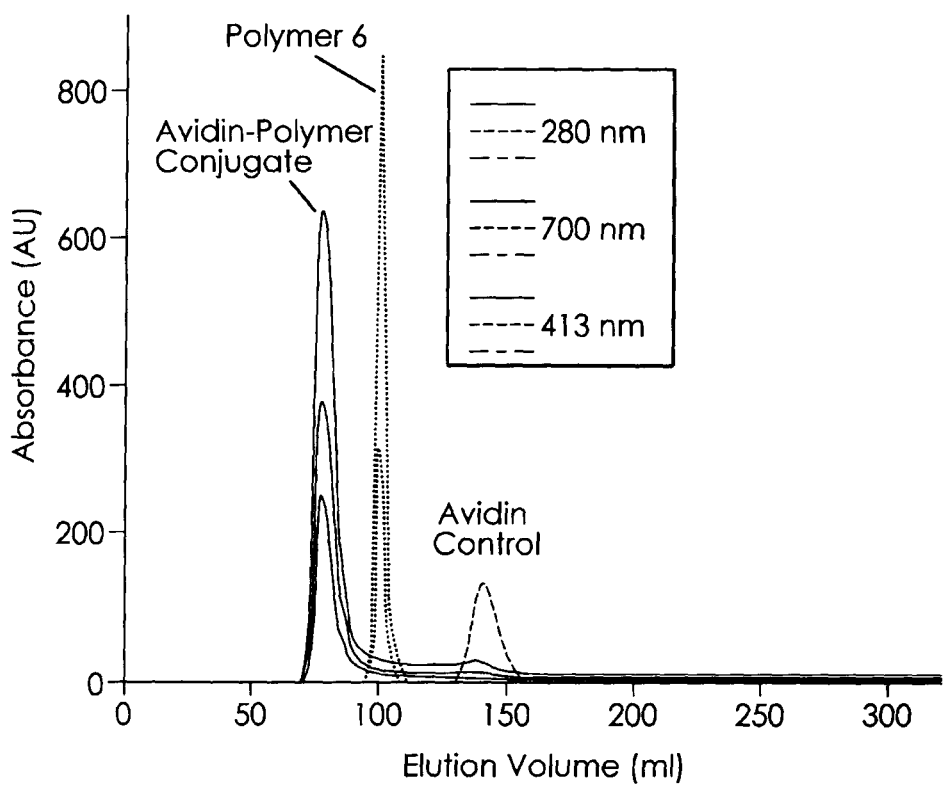
FIG. 1A is a size-exclusion FPLC (Hiprep 26/60™ Sephacryl™ S-200 HR column) of avidin (dashed line), copolymer 6 (dotted line), and conjugate 7 (solid line).

The invention relates to a water-soluble polymer having formula I:

$$Y\text{-}(L^1)_{n1}\text{-}(C(O))_{n2}\text{—}(R^1)_{n3}\text{—}R^2$$

In the description of formula I below, several variables independently designate molecular groups, e.g., $R^1$, W, $L^2$, X, $A^1$, and $A^2$; or numbers, e.g., n4, n4a, n5, n6, n, and m that may occur more than once in the formula. All such molecular groups and/or numbers may be the same throughout the formula, or one or more than one of the molecular groups and/or numbers, including all of the molecular groups and/or numbers, in the formula may be different.

In this specification, Y represents a coupling group. A coupling group is any group that reacts under mild conditions, e.g., less than 100° C. at ambient temperatures, with a complementary coupling group, called Z. The reaction of a coupling group Y and complementary coupling group Z forms a coupled group, called X in this specification.

Coupling groups Y and complementary coupling groups Z are well known in the art, and are summarized in a treatise by Hermanson entitled Bioconjugate Techniques. A majority of the coupling groups corresponding to Y and the complementary coupling groups corresponding to Z, as well as the resulting coupled groups corresponding to X disclosed in Hermanson's Bioconjugate Techniques, are incorporated herein by reference. Some examples are provided in the table below, as well as in the schemes. In the table, R and R' are distinguished. Elsewhere in the specification, R and R' are not distinguished.

For example, the coupling group Y on the polymer above may be coupled with a complementary coupling group Z on a protein or peptide to form a polymer-protein/peptide hybrid of the invention. The protein or peptide is represented by E in the specification, or a large solid ball in the schemes.

TABLE 1

Examples of coupling groups (Y), complementary coupling group Z, and coupled groups (X)

| Entry | Structures of X | Structures of Y | Structures of Z |
|---|---|---|---|
| 1. | 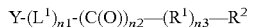 | —N$_3$ | —≡ |
| 2. | 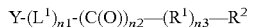 | —≡ | —N$_3$ |

TABLE 1-continued

Examples of coupling groups (Y), complementary coupling group Z, and coupled groups (X)

| Entry | Structures of X | Structures of Y | Structures of Z |
|---|---|---|---|
| 3. | 1,2,3-triazole (1,4-disubstituted) with R at C4 and R at N1 | —R—≡ | —R'—N₃ |
| 4. | 1,2,3-triazole (1,4-disubstituted) with R at C4 and R at N1 | —R—N₃ | —R'—≡ |
| 5. | —NH—R—[triazole]—CH₃ | N-hydroxysuccinimide ester linked via O—R to triazole—CH₃ | —NH₂ |
| 6. | —NH—R—[triazole]—CH₃ | —NH₂ | N-hydroxysuccinimide ester linked via O—R to triazole—CH₃ |
| 7. | R—S—[succinimide]—N—R—[triazole]—CH₃ | maleimide—N—R—[triazole]—CH₃ | —R—SH |
| 8. | R—S—[succinimide]—N—R'—[triazole]—CH₃ | —R—SH | maleimide—N—R'—[triazole]—CH₃ |
| 9. | —NH—C(O)—cyclohexyl—N—[succinimide]—S—R | —NH—C(O)—cyclohexyl—N—maleimide | —R—SH |
| 10. | —NH—C(O)—cyclohexyl—N—[succinimide]—S—R | —R—SH | —NH—C(O)—cyclohexyl—N—maleimide |
| 11. | —R'—[triazole]—[triazole]—CH₃ | ≡—R—[triazole]—CH₃ | —R'—N3 |

TABLE 1-continued

Examples of coupling groups (Y), complementary coupling group Z, and coupled groups (X)

| Entry | Structures of X | Structures of Y | Structures of Z |
|---|---|---|---|
| 12. | [bis-triazole structure] | —R—N3 | [alkyne-triazole structure] |
| 13. | [triazole-S-succinimide-N-R'] | [HS-R-triazole] | [maleimide-N-R'] |
| 14. | [triazole-S-succinimide-N-R] | [maleimide-N-R] | [HS-R'-triazole] |
| 15. | Avidin-Biotin—NH—[triazole] | [Biotin-amide-triazole structure] | Avidin- |
| 16. | —R—NH—C(O)—(CH$_2$)$_n$—N(triazole)—R'— | —R—NH—C(O)—(CH$_2$)$_n$—N$_3$ | —R'—≡ |
| 17. | [R'-S-succinimide-N-R-NH] | [maleimide-N-R-NH] | —R'—SH |
| 18. | [R-S-succinimide-N-R'-NH] | —R—SH | [maleimide-N-R'-NH] |
| 19. | [R'-HN-succinimide-S-Me] | [bis-succinimide-O linker with S-Me] | —R'—NH$_2$ |
| 20. | [R-HN-R'-succinimide-S-Me] | —R—NH$_2$ | [bis-succinimide-O-R' with S-Me] |

TABLE 1-continued

Examples of coupling groups (Y), complementary coupling group Z, and coupled groups (X)

| Entry | Structures of X | Structures of Y | Structures of Z |
|---|---|---|---|
| 21. | —R—NH—R'—N(succinimide-SMe) | N-oxysuccinimide-O—R— | $H_2N$—R'—N(succinimide-SMe) |
| 22. | —R—CH$_2$—NH—R'— | R—C(=O)H | $H_2N$—R'— |
| 23. | —R'—CH$_2$—NH—R— | $H_2N$—R— | R'—C(=O)H |
| 24. | —R—S—S—R'— | —R—SH | —R'—SH |
| 25. | —R—HN—R'— | N-oxysuccinimide-O—R— | $H_2N$—R'— |
| 26. | —R'—HN—R— | $H_2N$—R— | N-oxysuccinimide-O—R'— |
| 27. | —NH—R'—S—S—R— | —R—SH | —NH—R'—S—S-(2-pyridyl) |
| 28. | —NH—R—S—S—R'— | —NH—R—S—S-(2-pyridyl) | —R'—SH |
| 29. | —NH—R—S—R'— | —NH—R—I | —R'—SH |
| 30. | —NH—R'—S—R— | —R—SH | —NH—R'—I |
| 31. | R—CH=N—NH—R'— | R—C(=O)H | $H_2N$—NH—R'— |
| 32. | R'—CH=N—NH—R— | $H_2N$—NH—R— | R'—C(=O)H |
| 33. | —R—C$_6$H$_4$—NH—NH—R'— | —R—C$_6$H$_4$—N$_2^+$ | $H_2N$—R'— |
| 34. | —R'—C$_6$H$_4$—NH—NH—R— | $H_2N$—R— | —R'—C$_6$H$_4$—N$_2^+$ |
| 35. | —R—NH—C(=S)—NH—R'— | $H_2N$—R— | —R'—N=C=S |

TABLE 1-continued

Examples of coupling groups (Y), complementary coupling group Z, and coupled groups (X)

| Entry | Structures of X | Structures of Y | Structures of Z |
|---|---|---|---|
| 36. | —R'—NH—C(=S)—NH—R— | —R—N=C=S | $H_2N$—R'— |
| 37. | —R'—NH—C(=O)—NH—R— | —R—N=C=O | $H_2N$—R'— |
| 38. | —R—NH—C(=S)—NH—R'— | $H_2N$—R— | —R'—N=C=O |
| 39. | —R'—NH—C(=O)—R— | HO—C(=O)—R— | $H_2N$—R'— |
| 40. | —R—NH—C(=O)—R'— | $H_2N$—R— | HO—C(=O)—R'— |
| 41. | —R—C(=O)—NH—CH$_2$—C(=O)—NH—R'— (with HN bridging) | —R—(oxazolinone) | $H_2N$—R'— |

In formula I, $L^1$ represents a linking moiety that results from the chain initiating step of the polymerization process. For example, in Atom Transfer Radical Polymerization (ATRP) polymerization, $L^1$ is preferably —(CH$_2$CH$_2$O—)$_p$—C(O)—C(CH$_3$)$_2$— or —(OCH$_2$CH$_2$—)$_p$—C(O)—C(CH$_3$)$_2$— wherein p is a minimum of 1, 2, or 3, and a maximum of 20, 15, or 12 wherein a range may be formulated from any minimum value combined with any maximum value, and the value may be any number from 1-20, for example 3, 5, 8, 12, etc. Preferably, p is 2-4, more preferably 3.

In Reversible Addition Fragmentation Transfer (RAFT) polymerization, $L^1$ is preferably

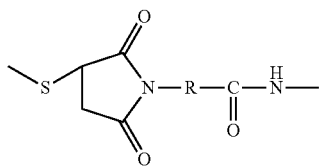

In the above formula, and in this specification unless indicated otherwise, R represents (i) a $C_1$-$C_{12}$ n-alkylene (i.e., alpha-omega alkylene) chain. Optionally one or more carbon atoms in the alkyl chain is replaced by a heteroatom selected from the group consisting of —O—, —S—, and —NH—, except that each such heteroatom is separated from other heteroatoms by at least two carbon atoms. Also optionally, the carbon atoms in the alkyl chain may be substituted with one or more substituents selected from the group consisting of: hydroxyl or oxo; (ii) phenyl or biphenyl, (iii) a carbocyclic non-aromatic ring having 5-7 carbon atoms; (iv) an aromatic heterocyclic ring having five or six atoms wherein at least one of the carbon atoms is substituted by a heteroatom selected from the group consisting of O, S, or NH; and (v) a non-aromatic heterocyclic ring having 5-7 carbon atoms wherein at least one of the carbon atoms is substituted by a heteroatom selected from the group consisting of O, S, or NH.

Most of the R groups are components of commercially available reagents. For specific examples, see Bioconjugate Techniques by G. T. Hermanson. Any R group that is disclosed in Hermanson but not included in the definition of R above is incorporated herein by reference.

Some examples of $C_1$-$C_{12}$ n-alkylene groups are any —(CH$_2$)$_r$— group wherein r represents 1-12, such as, for example, ethylene, n-butylene, n-hexylene, n-octylene, n-decylene, and n-dodecylene. Examples of n-alkylene groups that have carbon atoms replaced by heteroatoms include oligoethylene glycol and oligoethylenediamine.

Examples of cyclic, non-aromatic 5-7 member ring groups include cyclopentyl, cyclohexyl, and cycloheptyl. The preferred cyclic, non-aromatic 5-7 member ring group is cyclohexyl.

Examples of aromatic heterocyclic rings having 5 or 6 atoms wherein at least one, but not all, of the ring atoms is substituted by a heteroatom include furanyl, isothiazolyl, pyranyl, pyridinyl, triazolyl, pyridyl, pyrrolyl, thiazolyl, tetrazolyl, pyrazolyl, pyrimidinyl, and thiadiazolyl. The preferred aromatic heterocyclic 5 or 6 member ring group is triazolyl.

Examples of non-aromatic heterocyclic 5 to 7 member ring groups include pyrrolidinyl; tetrahydrofuranyl; 1,2-dioxanyl; 1,3-dioxanyl; 1,4-dioxanyl; piperidinyl; piperazinyl; and morpholinyl.

In a preferred embodiment, R is a cyclohexyl group and $L^1$ is represented by

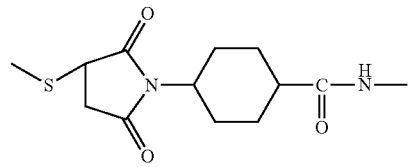

The letter n1 represents 0 or 1. The letter n2 also represents 0 or 1.

$R^1$ independently represents:

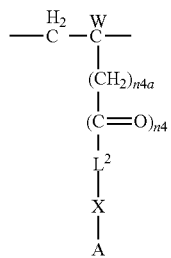

W independently represents —H, —CH$_3$, —COOH, or —CH$_2$COOH. The letter n4a independently represents 0 or 1. The letter n4 independently represents 0 or 1.

In one embodiment, the polymer is acrylate or methacrylate, and W is —H or —CH$_3$, respectively. In another embodiment, the soluble polymer is an itaconic anhydride polymer wherein the groups represented by W are a mixture of —COOH or —CH$_2$—COOH, and n4a is a mixture of 0 and 1.

$L^2$ independently represents a linker having the formula -(J)$_{n5}$-(R)$_{n6}$—. The letter J represents —O— or —NH—. The letter n5 independently represents 0 or 1. The letter n6 independently represents 0 to 6. In a preferred embodiment, if J represents O and n6 represents 0, then n5 also represents 0.

R in $L^2$ is as described above. In a preferred embodiment, R in $L^2$ represents —(CH$_2$CH$_2$O—)$_p$— or —(OCH$_2$CH$_2$—)$_p$—, where p is a minimum of 1, 2, or 3, and a maximum of 20, 15, or 12 wherein a range may be formulated from any minimum value combined with any maximum value, e.g., 3-12, and the value may be any number from 1-20, for example 3, 5, 8, 12, etc.

In a preferred embodiment, $L^2$ is OCH$_2$CH(OH)CH$_2$.

As discussed above, X independently represents a coupled group that results from reacting a coupling group (Y) and a complementary coupling group (Z).

A is represented by $(A^1)_n$ and $(A^2)_m$. $A^1$ independently represents a water soluble, immunogenicity reducing moiety. In the schemes, $A^1$ is represented by either a small, solid oval or a lightly-shaded, solid tear-drop shape.

Examples of water soluble immunogenicity reducing moieties include, but are not limited to, carboxylic acid derivatives of polyethylene glycol (PEG), carboxylic acid derivatives of sugars, glucose amine, galactose amine, oligoethylene glycol amine, oligoethyleneoxy, and mono-, di-, and tri-saccharides.

In a preferred embodiment, $A^1$ represents a saccharide such as a monosaccharide, a disaccharide, or trisaccharide.

Some examples of monosaccharides include glucose, fructose, ribose, galactose, xylose, glyceraldehyde, arabinose, allose, altrose, mannose, gulose, idose, and talose. Some examples of disaccharides include sucrose, lactose, maltose, trehalose, and cellobiose. Some examples of trisaccharides include nigerotriose, maltotriose, melezitose, maltotriulose, raffinose, and kestose.

In a preferred embodiment, $A^1$ represents (CH$_2$CH$_2$J)$_p$ wherein J represents O or NH, and p is a minimum of 1, 2, or 3, and a maximum of 20, 15, or 12 wherein a range may be formulated from any minimum value combined with any maximum value, e.g., 2-12, and the value may be any number from 1-20, for example 3, 5, 8, 12, etc.

$A^2$ independently represents an active moiety. In one embodiment, $A^2$ is a small molecule. Small molecules include organic compounds, organometallic compounds, salts of organic and organometallic compounds, saccharides, amino acids, and nucleotides. Small molecules typically have molecular weights less than approximately 450 Daltons. Small molecules include compounds that are found in nature as well as synthetic compounds.

Alternatively, $A^2$ is a peptide. The maximum number of amino acids present in the peptides of the invention is twelve. The minimum number of amino acids present in the peptides of the invention is one.

Some examples of useful small molecules and peptides are chromophores, radioactive labels, biologically active molecules or MRI imaging agents. Chromophores, radioactive labels, and biologically active molecules are well known in the art.

Chromophores include, for example, fluorescent, chemiluminescent, and bioluminescent molecules, as well as dyes. Examples of specific chromophores include, for example, rhodamine, Bodipy, NIRF dyes, fluorescein, Texas red, phycoerythrin, umbelliferone, and luminol. More examples are listed in the schemes.

Some examples of biologically active molecules are pharmaceutically active molecules. Some examples of pharmaceutically active molecules include, but are not limited to, curcumin, taxol, calachamycin, doxorubicin, prednisolone, dexamethasone, aspirin, acetaminophen, ibuprofen, isosorbide dinitrate, nicotinic acid, tetracycline, ampicillin, dexbrompheniramine, chlorpheniramine, albuterol, pseudoephedrine, loratadine theophylline, ascorbic acid, tocopherol, pyridoxine, metoclopramide, magnesium hydroxide, verapamil, procainamide hydrochloride, propranolol, captopril, ergotamine, flurazepam, diazepam, insulin, furosemide, hydrochlorothiazide, guaiphenesin, dextromethorphan, and benzocaine. In a preferred embodiment, the pharmaceutically active molecule is curcumin, taxol, calachamycin, or doxorubicin.

The biologically active molecule may also be a vitamin. Examples of vitamins include, but are not limited to, vitamin A, vitamin C, vitamin D, vitamin E, thiamin, riboflavin, niacin, vitamin B$_6$, folic acid, folate, vitamin B$_{12}$, calcium, iron, and zinc. In a preferred embodiment, the vitamin is a folate.

In another embodiment, $A^2$ is an MRI imaging agent. Such agents are well known in the art. An example of an MRI imaging agent is 1,4,7,10-tetraazacyclododecane-N,N',N'',N'''-tetraacetic acid/DOTA chelated with gadolinium.

In the schemes, $A^2$ is represented by either a small, solid ball or a darkly-shaded, solid tear-drop shape. Further examples of specific active moieties are shown in the schemes.

In $(A^1)_n$ and $(A^2)_m$, the letters n and m independently represent a minimum of 2, 15, or 20 and a maximum of 500, 200, or 100 wherein a range may be formulated from any minimum value combined with any maximum value, preferably about 20 to about 60, and more preferably about 30 to about 50, and the value may be any number from 2-500.

The letter n3 in formula I represents n+m.

$R^2$ in formula I represents H, a straight chain or branched alkyl group having 1-6 carbon atoms, Cl, or Br. Examples of straight chain alkyl groups having 1-6 carbon atoms are methyl, ethyl, propyl, butyl, pentyl and hexyl. Examples of branched alkyl groups having 1-6 carbon atoms are t-butyl, 2,3-dimethylbutyl, and 2-methylpentyl.

In one embodiment, the soluble polymer is a poly 2-hydroxyethyl acrylate or methacrylate that can be made using the ATRP method, wherein n4 is 1, J is O, n5 is 1, n6 is 2, and L' is —(CH$_2$CH$_2$O—)$_p$—C(O)—C(CH$_3$)$_2$—, p is 2-4, preferably 3, and $R^2$ is Br.

In yet another embodiment, the soluble polymer is a polyglycidyl acrylate or methacrylate that can be made using the RAFT method, wherein W is H or $CH_3$, n4 is 1, and $L^2$ is —$OCH_2CH(OH)CH_2$.

In a further embodiment of the invention, Y is replaced by E-X, wherein E represents a protein or a peptide. In this specification, a protein has more than twelve amino acid residues and a peptide has up to twelve amino acids. E may represent, for example, a chromophore, a radioactive label, a biologically active molecule, or an MRI imaging agent.

In a preferred embodiment, E is a targeting protein or a peptide. Targeting proteins and peptides bind specifically to a target molecule. Some examples of targeting molecules include antibodies, avidin, or streptavidin. Some examples of peptides include HIV TAT and RGD sequences. E may also be an enzyme. Some examples of enzymes include horseradish peroxidase, beta-galactosidase, and luciferase.

In this specification, an antibody is defined broadly as a protein that binds specifically to an epitope. Antibodies that bind specifically to an epitope may comprise an antibody hypervariable region. The antibody may further comprise an entire antibody variable region. The antibody may still further comprise an antibody constant region. Antibodies include, for example, a whole antibody, an antibody fragment, a chimerized antibody or a humanized antibody. The antibody may be polyclonal or monoclonal.

For example, the antibody may be a primary, secondary, or monoclonal antibody. The antibody may also be genetically or chemically modified. For use in humans, the antibody is preferably chimerized or humanized.

Suitable variable and hypervariable regions of non-human antibodies may be derived from antibodies produced by any non-human mammal in which monoclonal antibodies are made. Suitable examples of mammals other than humans include, for example, rabbits, rats, mice, horses, goats, or primates. Preferably, the antibodies are human antibodies. The antibodies may be produced in a transgenic mouse. An example of such a mouse is the so-called XenoMouse™ (Abgenix, Freemont, Calif.) described by Green, L. L., "Antibody Engineering Via Genetic Engineering of the Mouse: XenoMouse Stains are a Vehicle for the *Facile* Generation of Therapeutic Human Monoclonal Antibodies," J. Immunol. Methods," 10; 231(1-2):11-23(1999).

Antibodies fragments have binding characteristics that are the same as, or are comparable to, those of the whole antibody. Suitable fragments of the antibody include any fragment that comprises a sufficient portion of the hypervariable (i.e. complementary determining) region to bind specifically, and with sufficient affinity, to the epitope.

The preferred fragments are single chain antibodies. Single chain antibodies are polypeptides that comprise at least the variable region of the heavy chain of the antibody and the variable region of the light chain, with or without an interconnecting linker.

A chimerized antibody comprises the variable region of a non-human antibody and the constant region of a human antibody. A humanized antibody comprises the hypervariable region (CDRs) of a non-human antibody. The variable region other than the hypervariable region, e.g. the framework variable region, and the constant region of a humanized antibody are those of a human antibody.

The antibodies and functional equivalents may be members of any class of immunoglobins, such as: IgG, IgM, IgA, IgD or IgE, and the subclass thereof. The functional equivalents may also be equivalents of combinations of any of the above classes and subclasses.

In another embodiment, E is a bionanoparticle. The bionanoparticle may be, for example, a virus, ferritin, or apoferritin. Preferably, the bionanoparticle is a virus, and the virus is tobacco mosaic virus.

The virus may be genetically or chemically modified. The virus may also be an empty capsid.

Some further protein examples of E are Protein A, Protein G, Protein L, BSA, or ovalbumen. E may also be hepatitis B surface antigen.

Preferably, E is a therapeutic protein. Therapeutic proteins include, for example, erythropoietin, human growth hormone, and insulin.

Some further embodiments of the invention are shown in schemes 1-19.

The polymers of the invention are generally acrylate polymers. The polymer acrylates described herein include both polymers of acrylic acid, methacrylic acid, and itaconic acid, and their derivatives.

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g. Y, $L^1$, $R^1$, $R^2$, W, n1, n2, n3, etc.). Each group contains multiple members. For example, W represents —H, —$CH_3$, —COOH, or —$CH_2COOH$. Each member may be combined with each other member to form additional sub-groups, e.g., —H and —$CH_3$, —H and —COOH, or —$CH_3$ and —$CH_2COOH$.

The instant invention further contemplates embodiments in which each element listed under one group may be combined with each and every element listed under any other group. For example, n1 and n2 are identified above as independently representing 0 to 1. $L^1$ is identified above as representing a linking moiety that results from the chain initiation step of the polymerization process, for example, $L^1$ can be —($CH_2CH_2O$—)$_p$—C(O)—C($CH_3$)$_2$— or —($OCH_2CH_2$—)$_p$—C(O)—C($CH_3$)$_2$— wherein p represents 1-20. Each element of n1 and n2 (0 or 1) can be combined with each and every element of $L^1$ and p (—($CH_2CH_2O$—)$_p$—C(O)—C($CH_3$)$_2$— or —($OCH_2CH_2$—)$_p$—C(O)—C($CH_3$)$_2$— wherein p represents 1-20). For example, in one embodiment, n1 may be 0 and n2 may be 1. Alternatively, n1 may be 1, n2 may be 1, and $L^1$ may be —($CH_2CH_2O$—)$_3$—C(O)—C($CH_3$)$_2$—, where p is 3. Similarly, a another group is $R^2$, in which the elements are defined as H, a straight chain or branched alkyl group having 1-6 carbon atoms, Cl, or Br. Each of the above embodiments may be combined with each and every element of $R^2$. For example, in the embodiment wherein n1 is 1, n2 is 1, and $L^1$ is ($OCH_2CH_2$—)$_3$—C(O)—C($CH_3$)$_2$, where p is 3, $R^2$ may be Cl (or any other chemical moiety within the element of $R^2$).

With each group, it is specifically contemplated that any one of more members can be excluded. For example, if W is defined as —H, —CH$_3$, —COOH, or —CH$_2$COOH, it is also contemplated that W is defined as —CH$_3$ or —CH$_2$COOH.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

A list following the word "comprising" is inclusive or open-ended, i.e., the list may or may not include additional unrecited elements. A list following the words "consisting of" is exclusive or closed ended, i.e., the list excludes any element not specified in the list.

All numbers in the specification are approximate unless indicated otherwise.

Preparation of Polymer-Protein/Peptide Hybrids

A general synthetic methodology to produce copolymer-protein hybrids where polymers with a multiple number of copies of imaging agent/therapeutic agent and hydrophilic groups displayed in a brush polymer architecture with reactive chain end are conjugated (via the reactive chain end) to proteins are claimed in this patent application (see Scheme 1-5 for examples of embodiments of this invention claimed). We have synthesized copolymer-protein or copolymer-peptide hybrids by attaching the reactive chain ends of the polymers to peptides or proteins. In these novel hybrids a large number of imaging agent/drug units are attached per protein basis thereby producing biomaterials with potentially amplified detection/therapeutic capabilities. In one embodiment the detection/delivery and biological specificity of the bioconjugates can be exquisitely controlled by attaching antibodies to the polymers. It can be achieved via direct covalent bonding to an antibody or through the intermediacy of a biomolecular adapter such as streptavidin that can strongly react with biotinylated antibodies and polymers with biotin chain end simultaneously (see Schemes 3-5). Using current technologies, the number of copies of imaging agents/drugs that can be chemically conjugated to proteins (e.g. antibodies) is very limited. For instance, in the case of Mylotarg® (a calicheamicin-antibody conjugate) the drug to antibody ratio is 2:1. A fundamental limitation in the detection and therapeutic efficiency of imaging agent/drug labeled proteins such as antibodies arises from the fact that only a limited number of imaging agents/drugs can be attached per protein molecule, extensive modification of proteins with several copies of a drug/dye would cause deactivation of active sites of the proteins or antibodies.

Applications and breakthroughs in the field will depend critically on developing a general strategy for attaching several copies of drug molecules and imaging agents per protein without compromising the binding specificity and affinity of the proteins. We cover in this patent a general synthetic methodology to produce co-polymers in which imaging agents/ therapeutic agents and hydrophilic/biocompatible moieties are displayed in a brush polymer architecture, the polymers also possess a single reactive chain end available for bioconjugation (Scheme 1-5). The representation of the co-polymer-protein hybrids presented in Schemes 1 and 2 portray the fundamental synthetic breakthrough we have achieved: a copolymer composed of several copies of an imaging agent/ drug is attached via a single link to a protein. On a per protein molecule basis many more dyes/drugs can be targeted using this strategy.

In this patent application we cover, for example, bioconjugates of copolymers with (a) peptides (b) antibodies (including primary, secondary, monoclonal, chemically modified/ altered and genetically altered antibodies) (c) avidin, streptavidin, genetically altered, chemically altered/modified avidin/streptavidin) (d) Enzymes (e) Bionanoparticles including viruses, genetically modified viruses, chemically modified/altered viruses, empty viral capsids, other protein assemblies such as ferritin, apoferritin. (f) other proteins including Protein A, G, L, BSA, ovalbumen, antigens (such as the hepatitis B surface antigen) (g) conjugates with therapeutic proteins such as erythropoietin, human growth hormone, and insulin and their genetically altered and chemically modified variants are also covered in this patent application.

In the schemes below and unless indicated otherwise in this specification, p is a minimum of 1, 2, or 3, and a maximum of 20, 15, or 12 wherein a range may be formulated from any minimum value combined with any maximum value, e.g., 2-4, and the value may be any number from 1-20, for example 3, 5, 8, 12, etc., and n and m independently represent a minimum of 2, 15, or 20 and a maximum of 500, 200 or 100 wherein a range may be formulated from any minimum value combined with any maximum value, preferably about 20 to about 60, and more preferably about 30 to about 50, and the value may be any number from 2-500.

The development of living radical polymerization methods such as Atom Transfer Radical Polymerization (ATRP) [6] affords a convenient route to synthesize a range of acrylate polymers; by appropriate chemical manipulation, polymers with a single reactive chain end can be synthesized. Reversible Addition Fragmentation Transfer [RAFT] polymerization is another controlled polymerization technique which can be employed for a wide gamut of functional monomers [7]. The direct polymerization of some functional monomers such as acrylic acid cannot be performed via ATRP whereas it can be achieved using RAFT. In contrast to ATRP, RAFT polymerizations can be carried out without the presence of transition metal catalysts. Unlike ATRP, the examples of using RAFT polymers to produce polymer-protein hybrids are rare [8]. An extensive review by Haddleton and co-workers covers recent work describing the attachment of living synthetic polymers to peptides and proteins [2]; (a) A "grafting to" approach which involves the reaction between a preformed synthetic polymer and a protein: Poly methacryloxy ethyl glucoside with a fluorescein alkyne chain end has been synthesized and attached to the cowpea mosaic virus (CPMV) via the azide-alkyne triazole forming "click" bioconjugation reaction, there are other examples of this strategy [9,10] (b) The "grafting from" approach: where the peptide/protein acts as a macro-initiator and the polymer chain grows from the macroinitator: the use of streptavidin as a macroinitiator for the polymerization of N-isopropylacrylamide (NIPAM) and poly(ethylene glycol)methyl ether methacrylate (PEGMA) and other similar reports demonstrate this strategy [11,12]. (c) The "grafting through" method: where peptide macromonomers are polymerized, for example Val-Pro-Gly-Val-Gly (VPGVG) methacrylate was polymerized via ATRP to produce poly (VPGVG methacrylate) homopolymer [13].

The synthesis of copolymer-protein/peptide hybrid materials has been so far restricted to a few monomers such as carbohydrate, PEG acrylates/methacrylates and N-isopropyl acrylamide [2, 14]. The fact that a wide range of acrylates/ methacrylates cannot be freely used to produce copolymers via free radical polymerization arises from the difference in reactivity and solubility between monomers: for instance, the preparation of a copolymer containing a monosaccharide derived acrylate (hydrophilic) and taxol acrylate (hydrophobic) would be very challenging. The acrylate derivatives of many biologically active molecules/imaging agents such as curcumin could be synthesized but cannot be polymerized via free radical polymerization methods because the molecules are radical scavengers. It should be noted that there has recently been tremendous interest in curcumin, [(1E,6E)-1,7-bis(4-hydroxy-3-methoxyphenyl)hepta-1,6-diene 3,5-dione] the primary active ingredient in the Indian spice turmeric, because it has been shown to have antioxidant, [15], anticancer, [16], anti-inflammatory, [17] and potent anti-Alzheimer's disease activity [18]. One of the major limitations of using curcumin as a drug is its poor water and plasma solubility. A patent application [19] and recently accepted paper in Organic Letters [20] from my group describes an efficient synthetic route to reactive mono-functional curcumin derivatives; these derivatives represent one group of molecules exploited to produce water soluble copolymer-protein hybrids covered in the patent. The imaging efficacy and pharmacokinetics of many imaging agents and therapeutic drug candidates will be improved considerably if a general synthetic technology for using them to produce water soluble and/or biocompatible polymer-protein hybrids is developed. A general synthetic methodology to produce copolymers with a large number of copies of imaging agent/therapeutic agent and hydrophilic/biocompatible moieties attached in brush polymer architecture with a single reactive chain end are covered in this patent. Conjugates of these polymers with peptides/proteins are also covered in this application. The polymer-protein/peptide hybrids are synthesized by attaching the reactive chain ends of the polymers to peptides and proteins. In these novel hybrids a large number of imaging agent/drug units will be present thereby producing biomaterials with potentially amplified detection/therapeutic capabilities.

Bionanoparticles

Some of the proteins which have been employed in previous reports to synthesize polymer protein hybrids are bovine serum albumin, streptavidin, papain, hair, and bionanoparticles such as the cowpea mosaic virus [9, 21]. Among proteins, the use of bionanoparticles as natural nano-scaffolds for polymer attachment is a very recent development [9, 21-24]. Many bionanoparticles such as plant viruses have been isolated in gram quantities from infected plants and small molecules including dyes, magnetic resonance imaging agents, carbohydrates, and therapeutic drugs have been attached to these nano-blocks for potential imaging and therapeutic applications [25-28]. The direct attachment of dyes, targeting ligands such as carbohydrates or MRI agents to bionanoparticles do not represent an optimized construct for in vivo imaging because small molecule modified bionanoparticles are highly immunogenic. In order to reduce the immunogenicity of these constructs fluorescein poly(ethylene glycol)N-hydroxy succnimide has been attached to CPMV; the polymer shields the virus from the immune system in the mouse model but the virus-polymer hybrid is not targeted to any specific cell type, hence this does not yet represent an optimized construct. In an improved model poly(methacryloxy ethyl glucoside) with a fluorescein alkyne chain end has been synthesized and attached it to CPMV. The dye (drug model/imaging agent) serves as a linker to connect CPMV and the polymer, the polymer shields the virus and the dye from the immune system in the mouse model [9]. This construction is still not optimum because the number of dye/drug molecules which can be attached per bionanoparticle is limited to one dye per polymer chain connected to the virus. In the current patent living brush co-polymers with a single reactive chain end, displaying multiple copies of different components (a) imaging agents/therapeutic agents, (b) water soluble and biocompatible groups like short PEGs/carbohydrates are synthesized. These polymers are then attached to bionanoparticles via the reactive chain ends (examples Scheme 1 and 2). The optimized design proposed here increases the number of functional units (imaging agents/therapeutic units) which can be attached per bionanoparticle many fold because each attached polymer chain displays several copies of the functional unit in a brush architecture. The PEG/sugar component of the polymer serves to shield the bionanoparticle from the immune system.

Proteins: Antibodies and Avidin/Streptavidin

Ehrlich described the concept of a "magic bullet" and recognized the potential of antibodies as therapeutic agents in the early 20th century [29]. Humanized monoclonal antibodies (mAbs) have been developed for the treatment of several diseases and for preclinical imaging applications [30]. Some antibodies in the market are conjugates: Zevalin® and Bexxar® are radio conjugates. Mylotarg®, a FDA approved toxin conjugate is a recombinant humanized monoclonal antibody covalently linked with the anti-tumor drug calicheamicin and is used to treat acute myeloid leukemia [31]. The current approach to convert humanized mAbs into drugs is to attempt to conjugate them to radionucleotides or cytotoxic drugs [32]. Most initial antibody conjugate efforts employed radionucleotides; the procedure is costly and requires that drugs should be generated immediately prior to use. Toxin conjugates are a challenging chemical problem; for e.g., many anticancer drugs like taxol are not water soluble and are thus difficult to conjugate to water soluble antibodies. Using current technologies, the number of copies of cytotoxic drugs/radionucleotides that can be chemically conjugated to an antibody is very limited. For example, in the case of Mylotarg® the drug to antibody ratio is 2:1 [31]. Extensive modification of antibodies with several copies of a drug/imaging agent would cause deactivation of the antigen binding sites and the introduction of unique reactive sites in antibodies (like cysteine residues) through gene manipulation allows for the attachment of only few drug/dye molecules per antibody molecule. Dye labeled antibodies [33] are used as detection reagents for a range of biological imaging applications. Near Infrared Fluorescence (NIRF)-dye labeled antibodies have recently been used for gel imaging for example (IRDye® secondary antibodies) and for in vivo non invasive animal imaging [34]. This technology is also limited by the number of dyes one can covalently conjugate to a single antibody. Biopolymer-antibody conjugates are commercially available, the most common being enzyme antibody conjugates [33], these are used as detection reagents in western (immuno) blots, indirect immunohistochemistry and other bioassays; the antibody-enzyme conjugates retain their recognition specificity. There have also been a few reports of synthetic polymer (produced by uncontrolled free radical polymerization) antibody conjugates [35].

Avidin is a tetrameric glycoprotein purified from egg white. Streptavidin is a non glycosylated analog of avidin, recombinantly produced streptavidin is commercially available. The highly specific interaction of avidin/streptavidin with biotin has a $Ka>10^{14}$; the avidin-biotin interaction has been exploited for numerous applications in biology; conjugates of these proteins with small molecules such as dyes and biopolymers such as enzymes are commercially available and widely used for detection and bioassays [33, 36].

Applications and breakthroughs in the field will depend critically on developing general strategies for attaching several copies of drug molecules and imaging agents per antibody/avidin/streptavidin without compromising the binding specificity and affinity of the proteins. The copolymers covered in this patent application (with multiple copies of imaging agent/therapeutic agent and hydrophilic and/or biocompatible molecules attached in a brush polymer architecture with a single reactive chain end) will be attached to the antibodies/avidin/streptavidin to produce conjugates (Scheme 1-5). Each of these protein molecules targets a large number of imaging agents/drugs. Such an approach would reduce the amount of antibody/avidin/streptavidin required for imaging or targeting thereby amplifying the detection/therapeutic efficiency, reducing the price (proteins are typically more expensive than acrylate polymers) and the toxicity of conjugates. Using this strategy a broad range of drug/imaging molecules in a brush polymer format are employed to produce conjugates with potentially amplified bio-efficacy and these are covered in this patent application (Schemes 1-5). Among the dyes used for polymeric display all dyes which absorb and emit in the wavelength range 280-1400 nm are covered in this patent. Among drugs curcumin and its derivatives, doxorubicin, taxol and other drugs displayed in brush architecture polymers with reactive chai-ends to produce antibody/avidin/streptavidin conjugates are covered (see Schemes 1-5 for examples). We also cover similar conjugates with MRI agents, radionucleotides and other classes of cytotoxic drugs displayed in the formats represented by Schemes 1-5.

JOURNAL REFERENCES

Two references of note on the use of methacrylic and methacrylates for imaging purposes are listed below. Reference 1 is of particular note in that it describes a method for incorporating Fluorescein Moieties in PMMA in the main chain. Reference 2 describes a method of obtaining pendant chromophoric entities.
1. Synthesis of PMMA Labeled with Fluorescein Moieties via ATRP, Li, Geng, et. al. J of Macromolecular Science, Part A: Pure and Applied Chemistry (2008), 45(4), 328-334
2. Methacrylic polymers containing permanent dipole azobenzene chromophores spaced from the main chain, Altomare, et. al., Macromolecular Chemistry and Physics (1999), 200 (3), 601-608.

PATENT REFERENCES

U.S. Pat. No. 7,317,058, invented by Yamamoto and assigned to Nitto Denko Corporation entitled "Methacrylate Polymer and Non-linear Optical Device Material Composition" describes a optical device composition which includes a trifluoro vinyl group containing poly(methacrylate (PMA) that is cross-linkable and thermally stable after cross-linking. The composition may include a trifluorovinyl compound containing chromophore and PMA which provides non-linear optical ability to the matrix polymer system. These structures involving PMA are quite different than the current invention and do not involve bioconjugates, as well.
U.S. Pat. No. 7,052,917 invented by Ohnishi, et. al. entitled "Polymerizable Biotin Derivatives, Biotin Polymer, and Polymer Responsive to Avidin Stimulation" describes a polymer biotin combination which is sensitive to environmental conditions. Again these complexes are very different than the instant invention and do not involve chromophores directly.
U.S. Pat. No. 7,060,372 invented by Fryd, et. al. entitled "Polymers Having Attached Luminescent Metal Complexes and Devices Made with Such Polymers" describes light emitting entities that result from metal complexes attached to the polymer chain.
U.S. Pat. No. 7,101,682 invented by Ullman, et. al. entitled "Simultaneous Screening of Multiple Analytes" describes a system of analysis involving multiple ligands to detect multiple analytes. Chemi-luminescent compounds are used for the analysis. Signals are modulated depending on the number and type of analytes present. The compounds are quite different than used in this instant invention. Bioconjugates are used in this analysis.
U.S. Pat. No. 6,632,926 invented by Chen, et. al. entitled "Antibody Variants" describes conjugates used to target antigens of interest. Chromophores are used in some analyses.
U.S. Pat. No. 6,103,446 invented by Devlin, et. al. entitled "Fluorescent Chromophore Covalently Linked to an Organic Support Material" describes a solid organic support material to which are either directly or via a bridging group covalently linked to fluorescent chromophores which can be used for diagnostic purposes. These compounds are again very different than those used in this instant invention.
U.S. Pat. No. 6,001,337 invented by Keller, et. al. entitled "Cosmetic composition with Polymer Bound Benzophenone Chromophores" describes a polymer with repeating structural units that can accommodate these chromophores. Maleic anhydride polymers are one class of polymer used.

General Synthetic Design

The general design involved the synthesis of living brush polymers in which the side chain pendant groups and the polymer chain end possess orthogonal reactivity (e.g. Scheme 6 and Scheme 7). Water soluble, biocompatible moieties such as short PEG derivatives or carbohydrate derivatives and imaging/therapeutic agents are attached to the reactive polymer side chains in a one pot sequential reaction followed by purification of the resulting polymers via Sephadex chromatography (e.g. Scheme 2). Orthogonal reactivity incorporated in the design ensures that the final imaging agent/drug labeled polymers still retain a reactive chain end which can be employed for bioconjugation. The reactivity of the final imaging agent/drug labeled polymer can be varied by selective covalent modification of the chain ends with appropriate hetero-bifunctional linkers (Schemes 1 and 2). It should be noted that there has been a recent report describing the synthesis of alkyne side chain poly(alkyne) polymers [37] to which various ratios of sugar azides were attached via "click" chemistry, this approach is not general and is not amenable to scale-up because many of the intermediates involved in the synthesis of the small molecule azides are potentially explosive, [for instance see Experimental section page 10 of reference 37].

Some embodiments of the design covered in this patent are: (a) Polymers with side chain carboxyl groups (examples of monomers include tertiary butyl acrylate, tertiary butyl methacrylate, acrylic acid, methacrylic acid, glutamic acid and aspartic acid and their derivatives) with an azide, alkyne, biotin chain end (b) Polymers with side chain amine groups (examples of monomers include 2-aminoethyl methacrylate, 2 aminoethyl acrylate and their derivatives, lysine and lysine derivatives) with an azide, alkyne and biotin chain ends. (c) Polymers with amine, carboxyl or aldehyde pendant side groups with azide chain ends (d) Copolymers with (a large number of copies of imaging agent/therapeutic agent and hydrophilic and/or biocompatible groups displayed on the polymer side chain) with azide, alkyne, thiol, aldehyde, biotin, maleimide or N-Hydroxy-Succinimide and other reactive chain ends typically employed for bioconjugation. The pre-polymers with amine, carboxyl, azide side chains covered in this patent application are synthesized via atom transfer radical polymerization (ATRP) or reversible addition fragmentation transfer polymerization (RAFT), anionic/cationic living polymerization or solid phase peptide synthesis (for some examples see Schemes 6 and 7). Some of the chemistries used for covalent modification of the pendant side chain groups of the polymers are amidation reactions or the [3+2] cycloaddition azide alkyne triazole forming "click" reaction or Schiff's base reaction and reductive amination reactions.

A Typical Example

Synthesis of Polyacrylic Acid with Single Azide/Biotin Chain End Followed by Polymer Modification Reactions Tertiary butyl acrylate was polymerized using an azide incorporated initiator. The resulting polymer 1a was reacted with a novel alkyne derivative of biotin under [3+2] cycloaddition "click" conditions to produce a polymer with a single biotin chain end (Scheme 6, also see experimental section for details). The polymers with azide and biotin chain ends were deprotected to produce poly(acrylic acid) with a single biotin or azide chain end (Scheme 6 and experimental section). The polymers 1b and 1c will be further reacted with varying ratios of amine derivatives of dyes/drugs (Dye-$NH_2$/Drug-$NH_2$) followed by commercially available glucose amine (Glu-$NH_2$)/amine derivatives of carbohydrates or oligo-ethylene glycol-$NH_2$ (OGE-$NH_2$) in two sequential amidation steps to produce libraries of polymers with varying loadings of dye/drug and Glu-$NH_2$/OGE-$NH_2$ (Scheme 6 and Scheme 8, also see experimental section). The glucose/PEG component of the polymers serves to improve the water solubility and reduce the immunogenicity of the drug/dye component. The excess small molecules will be purified from the copolymers via size-exclusion Sephadex chromatography.

In an embodiment of this invention a commercially available near-infrared fluorescence (NIRF) imaging dye and glucose amine were employed to produce two series of polymers with either a single azide or a single biotin chain end (Scheme 8). The polymers were characterized via $^1$H NMR; Infrared spectra of the polymers confirm that the azide groups in the final polymers is intact (azide peak at 2100 nm); Gel Permeation Chromatography of the polymers indicates that they have low polydispersity (see experimental section for detailed description). The NIRF dye labeled polymers were attached to proteins such as avidin/streptavidin and Bovine serum albumen to demonstrate the synthetic technology covered in this patent, these hybrids have various life science applications including non invasive animal imaging (see next sections).

Another example can be afforded by an example in Scheme 8: the amine end of a novel curcumin derivative CURC-GLFG (peptide linker modified curcumin) [19, 20] coupled to poly(acrylic acid) with a single azide or biotin to produce two series of polymers are also covered in this patent application. The peptide linker serves as a biodegradable spacer, the biocompatible and biodegradable nature of the tetrapeptide linker GFLG has been previously confirmed [34]. These biocompatible water soluble polymers which display therapeutic curcumin units in a brush architecture attached to targeting peptides (which penetrate the blood brain barrier) [38,39], antibodies and bionanoparticles to produce plasma soluble biomimetic polyphenols to address a wide range of pathologies including inflammation, cancer, and Alzheimer's disease are covered in this patent. The synthetic approach presented here is general; a wide range of derivatives of therapeutic and imaging agents including amine, carboxylic acid and N-Hydroxysuccinimide derivatives of dyes, gadolinium chelators (magnetic resonance imaging probes) and drugs such as taxol can be attached to polymers (see Schemes 8 and 9 for some examples covered in this patent application). Hydrophobic dye/drugs can be coupled to 1b/1c followed by OGE-$NH_2$ because of the unique solubility of oligo-ethylene glycol amine in particular and PEGs in general (PEGs are soluble in most organic solvents and water). The reactivity of the unique azide/biotin chain ends is orthogonal to that of the carboxylic acid groups in the polymer backbone of 1b; after two amide couplings with Dye-$NH_2$/Drug-$NH_2$ and Glu-$NH_2$/OGE-$NH_2$, the azide/biotin group is still available for further orthogonal elaboration. The chemical transformation of the azide chain end by reactions with appropriate hetero-bifunctional cross-linkers to produce polymers with reactive aldehyde, thiol, maleimide, N-Hydroxy succinimide and alkyne chain ends are covered in this application, this expands the scope of bioconjugation chemistries which one can employ to synthesize the polymer protein hybrids (see Schemes 8 and 9 for examples).

The series of polymers described in Scheme 8 and Scheme 9 are some of the constructs covered in this patent application. We cover conjugates of these polymers with (a) peptides (b) antibodies including primary, secondary, monoclonal, chemically modified/altered and genetically altered antibodies) (c) avidin, streptavidin, genetically altered, chemically altered/modified avidin/streptavidin) (d) Enzymes (e) Bionanoparticles including viruses, genetically modified, chemically modified/altered viruses, empty viral capsids, other protein assemblies such as ferritin, apoferritin (f) other proteins including Protein A, G, L, BSA, ovalbumen, antigens such as the hepatitis B surface antigen. (g) Conjugates with therapeutic proteins such as Erythropoietin and human growth hormone and their genetically altered and chemically modified variants.

Reversible Addition Fragmentation Transfer Polymerization Followed by Polymer Modification Reactions Reversible addition fragmentation transfer (RAFT) polymerization is a controlled polymerization method which can be employed for a wide gamut of functional monomers [7]. The direct polymerization of functional monomers such as acrylic acid cannot be performed via ATRP whereas it can be achieved using RAFT [8]. ATRP is generally catalyzed by transition metal salts like Cu (I); in contrast RAFT polymerizations can be carried out without the presence of transition metal catalysts. There have been very few examples in literature of using RAFT polymers to produce protein polymer hybrids [2]. An example of this embodiment is afforded by poly acrylic acid with a unique alkyne chain end synthesized via RAFT in accordance with Scheme 10 using VAZO-88 as the initiator and 1-cyanoethyl 2-pyrrolidone-1-carbodithioate as the chain transfer agent. The thiocarbamate end group of the polymer will be hydrolyzed to produce a polymer with a unique thiol chain end. Further modification of the polymer with appropriate hetero-bifunctional cross-linkers, (e.g. maleimide-alkyne heterobifunctional cross-linker) will produce poly(acrylic acid) with a unique alkyne chain end. The polymer 3b can be reacted with varying ratios of amine derivatives of dyes/drugs (Dye-$NH_2$/Drug-$NH_2$) followed by commercially available glucose amine (Glu-$NH_2$)/amine derivatives of carbohydrates or oligo-ethylene glycol-$NH_2$ (OGE-NH$_2$) in two sequential amidation steps to produce libraries of polymers with varying loadings of dye/drug and Glu-NH$_2$/OGE-NH$_2$ these copolymers are covered in this application (Scheme 11). By judicious chemical modification using custom designed hetero-bifunctional linkers RAFT polymers with a single reactive SH, maleimide, N-Hydroxy succinimide, aldehyde and azide chain ends will be prepared; these constructs are covered in this application (Scheme 11). These polymers which display multiple copies of dye/drug and biocompatible PEG/Sugar units will be attached to proteins and bionanoparticles.

We cover conjugates of these polymers with (a) peptides (b) antibodies including primary, secondary, monoclonal, chemically modified/altered and genetically altered antibodies) (c) avidin, streptavidin, genetically altered, chemically altered/modified avidin/streptavidin) (d) Enzymes (e) Bionanoparticles including viruses, genetically modified, chemically modified/altered viruses, empty viral capsids, other protein assemblies such as ferritin, apoferritin (f) other proteins including Protein A, G, L, BSA, ovalbumen, antigens such as the hepatitis B surface antigen. (g) Conjugates with therapeutic proteins such as Erythropoietin and human growth hormone and their genetically altered and chemically modified variants.

Scheme 10. Synthesis of side chain carboxylic acid polymers with reactive chain end based on RAFT.

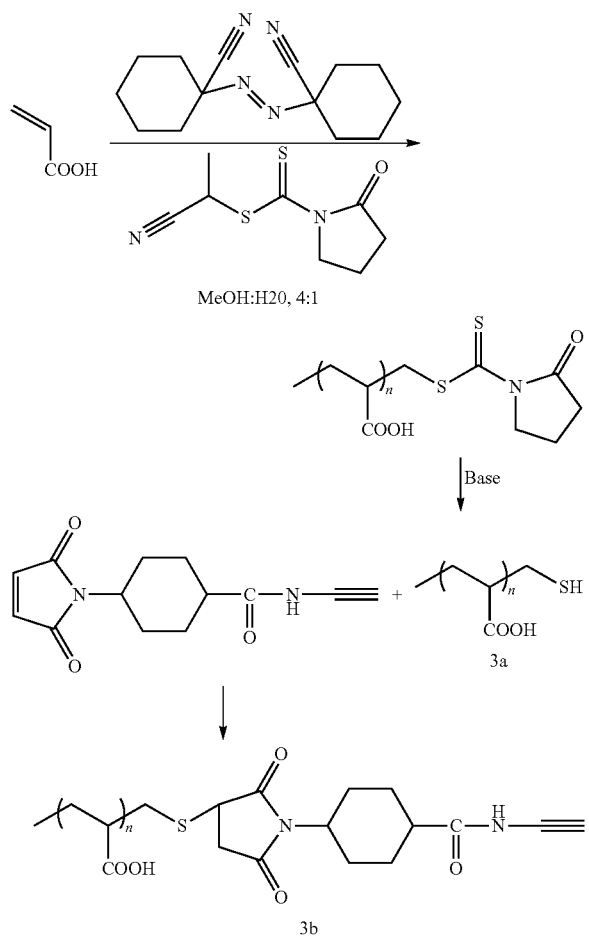

Bioconjugate Design and Purification
General Strategy

The overall design for synthesizing the conjugates covered in this application involves two strategies, (a) The formation of a covalent bond between the protein/peptide and the copolymers (b) The formation of a non covalent link between avidin/streptavidin and biotinylated copolymers, it must be noted that the interaction between avidin and biotin extremely strong with a Ka>$10^{14}$.

Some of embodiments of this design covered in this application are: (a) The chemical modification of the amine groups from the lysine residues in proteins and bionanoparticles with N-Hydroxy Succinimide-R-Alkyne or N-Hydroxy Succinimide-R-Azide hetero bifunctional linkers [9] followed by covalent attachment of brush copolymers with single reactive azide/alkyne chain end via the azide-alkyne triazole forming "click" bioconjugation reaction (Scheme 1 and 2). (b) The covalent attachment of targeting peptides displaying alkyne/azide groups with brush copolymers (Scheme 1 and 2). (c) Incubation of brush copolymers with unique biotin chain ends with avidin/streptavidin (Scheme 1 and 2). (d) The covalent attachment of copolymers with a single N-Hydroxy succinimide, aldehyde group or thiol group to the lysine residues of proteins or to lysine residues covalently modified with sulfosuccinimidyl-4-(N-maleimidomethyl)cyclohexane-1-carboxylate [22]. (e) The attachment of copolymers with a single maleimide group with the thiol groups from the cysteine residues of proteins. The representation of the copolymer-protein hybrids Scheme 1 and 2 clearly portrays the fundamental breakthrough this patent covers: a copolymer composed of several copies of a drug/imaging agent component and a PEG/Sugar component can be attached via a single link to a protein. The number of dye/imaging agents which can be attached to and targeted by proteins is multiplied many fold using this strategy (see Schemes 1-5 for some embodiments of the conjugates covered in this application).

Typical Example of a Bioconjugate

Avidin and Streptavidin-Copolymer Conjugates

We have recently synthesized a protein polymer hybrid by incubating biotin terminated poly(D-Glucosamine)-poly (NIRF) polymer with avidin (Scheme 12). The synthesis involved the polymerization of tert-butyl acrylate via ATRP [6] using an azide incorporated initiator 1 to produce poly (tert-butyl acrylate) 2 (Scheme 12). The intact nature of the azide group in the polymer was confirmed by the presence of the azide peak at 2113 cm$^{-1}$ in the IR spectrum of the polymer (see Experimental section). The resulting polymer was reacted with an alkyne derivative of biotin 3 under [3+2] azide-alkyne triazole forming "click" conditions to produce a polymer with a single biotin chain end 4 (Scheme 12). Peaks arising from the biotin moiety [40] at 4.48 ppm and 4.31 ppm were observed in the $^1$H NMR of 4, peaks at 7.68 (s), and 7.44 (s) arising from the triazole protons [41] were also observed (see Experimental section). Polymer 4 was treated with trifluoro acetic acid (TFA) to produce poly(acrylic acid) (PAA) with a single biotin chain end 5. The rationale for synthesizing PAA with a single chain end is based on the facts that (a) PAA is FDA approved and is generally regarded as safe (GRAS); (b) amine derivatives of a broad spectrum of dyes and a wide range of therapeutic agents are readily available commercially and can be employed using amidation chemistry with PAA to produce copolymers and (c) azidotriethylene glycol and the ATRP initiator with the azide group employed for the polymerizations are safe (many short chain azides are explosive). The amine derivatives, NIRF—NH$_2$ (ADS832WS) and Glu-NH$_2$ (D-(+)-glucosamine) were grafted to the PAA polymer 5 using standard amide coupling reagents 1-Ethyl-3-(3-dimethyllaminopropyl)carbodiimide hydrochloride (EDC.HCl) and N-Hydroxybenzotriazole (HOBt) in DMF to produce 6. The polymers synthesized were characterized via $^1$H NMR, Gel Permeation Chromatograph (GPC) and FT-IR spectroscopy.

Figure 1B:
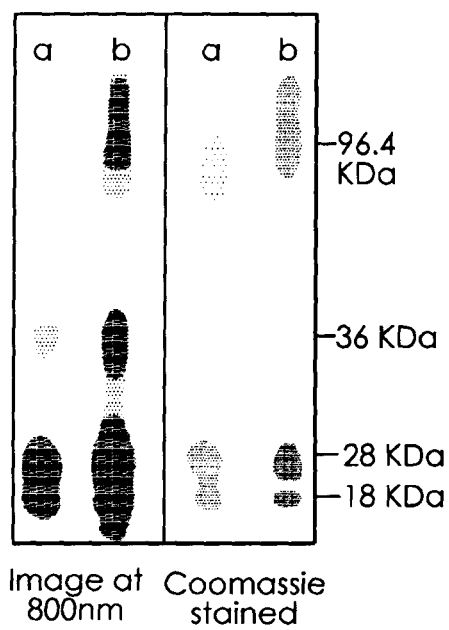
FIG. 1B is a SDS-PAGE of avidin (lane a) and conjugate 7 (lane b).

Based on the GPC results, comparing the molecular weights of 4 and 6, the percentage of the NIRF dye in the polymer 6 was determined to be ~17% per polymer chain (see Experimental section). Polymers with higher dye loading numbers and a control polymer 6a (PAA with dye alone) were also synthesized, however, those polymers were not readily soluble in water. Therefore, copolymer 6 was chosen for further studies due to its better solubility in water. It should be noted that recently, side chain poly(alkyne) polymers were synthesized and various azide molecules were attached to the polymer back-bone via "click" chemistry [37]. The approach is restricted to a few azides because many small azides are potentially explosive [37]. The copolymer-protein hybrid 7 was synthesized by incubating the copolymer 6 with avidin. The formation of a conjugate was indicated by higher molecular weight bands in SDS PAGE; the conjugate band which glowed when imaged using a NIRF imager was also visible following Coomassie staining indicating the presence of both polymer and protein at the same position (FIG. 1B). The formation of the conjugate was further confirmed via size exclusion Fast Protein Liquid Chromatography (FPLC) where the conjugate 7 eluted earlier (due to its higher molecular weight) in comparison to the synthetic polymer 6 and the control avidin sample (FIG. 1A).

Typical Example of a Covalent Bioconjugate

BSA-Copolymer Conjugates

Figure 2A:
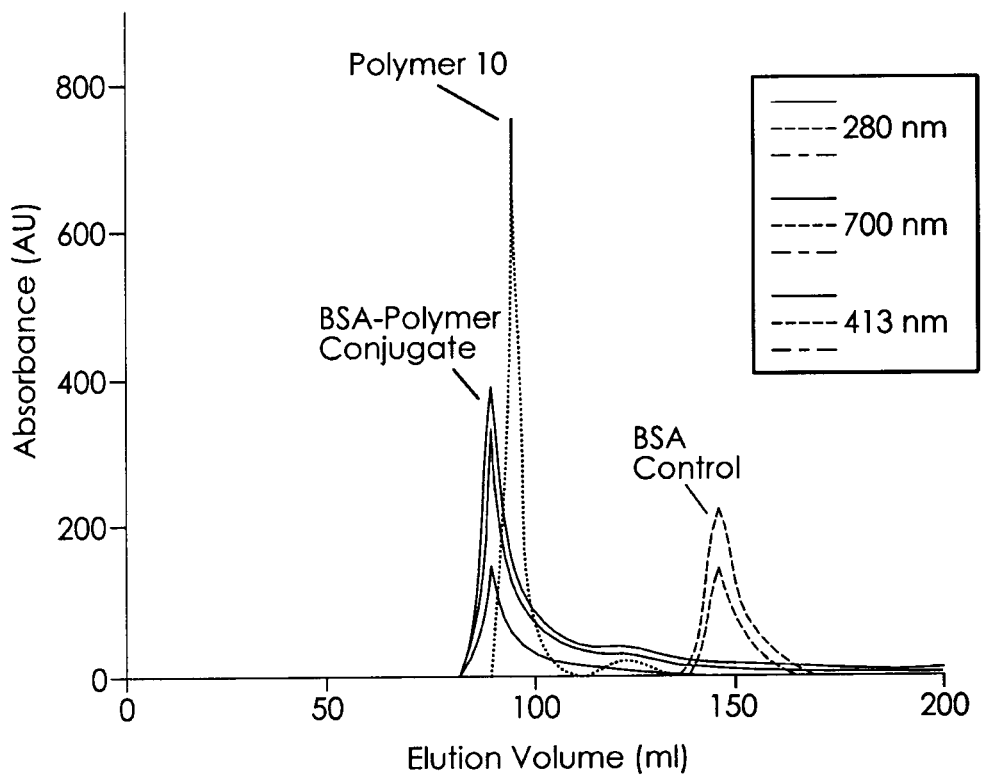
FIG. 2A is a Size-exclusion FPLC (Hiprep 26/60™ Sephacryl™ S-200 HR column) of azide modified BSA 13 (dashed line), copolymer 10 (dotted line), and conjugate 14 (solid line).
Figure 2B:
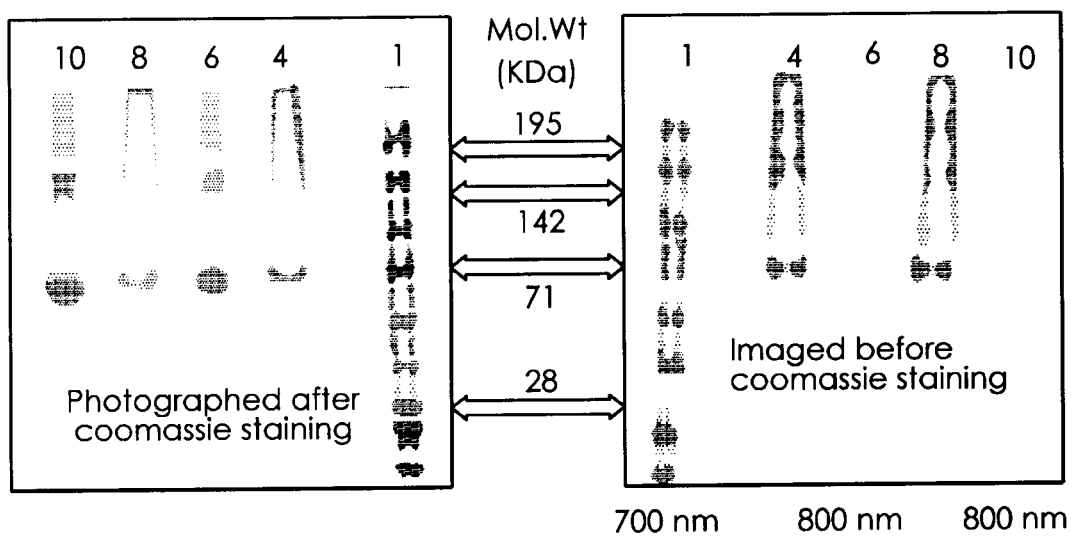
FIG. 2B is a SDS-PAGE of conjugate 14 (lane 4&8), mixture of azide modified BSA 13 & copolymer 10 without "click" reagents (lane 6) and unmodified BSA (lane 10).

In the second synthetic methodology (Scheme 13) the azide-terminated polymer 2 was treated with TFA to produce PAA with azide chain end 8. The pendant carboxylic acid side-chains of polymer 8 were grafted with NIRF—NH$_2$ and Glu-NH$_2$ via amide-coupling (EDC.HCl and HOBt) in DMF to produce poly(glucosamine)-poly(NIRF dye) copolymer 9. The polymer 9 with reactive azide chain-end was incubated with alkyne modified BSA under "click" bioconjugation conditions [9] but unfortunately without any success (lack of reaction confirmed via SDS-PAGE; data not shown). Earlier reports support the reduced/lack of reactivity of alkyne modified proteins in "click" bioconjugation reactions [42]. To circumvent the above mentioned problem copolymer 9 was reacted with a large excess of di-propargyl ether under "click" condition to convert the azide-terminated copolymer to an alkyne-terminated poly(glucosamine)-poly(NIRF dye) copolymer 10. The absence of the azide peak (~2100 cm$^{-1}$) in the FT-IR spectra confirmed the conversion of all the azide-end groups to alkyne (see Experimental section). In a separate reaction BSA was modified by reacting the surface lysine groups with a NHS-Azide hetero-bifunctional linker to produce azide labeled BSA 13. The incubation of azide-linker modified BSA 13 with alkyne terminated copolymer 10 finally produced the desired polymer-protein hybrid 14. The formation of the conjugate was confirmed via FPLC (FIG. 2A) and SDS-PAGE (FIG. 2B). The conjugate 14 eluted earlier than both the copolymer 10 and modified BSA 13 in the FPLC experiment. The unmodified BSA 11 eluted at the same volume as the modified BSA 13; hence it was not shown in the chromatogram (FIG. 2A). The SDS-PAGE gels were consistent with the FPLC results, the bands which glowed at 800 nm (lanes 4 & 8) also appeared when stained with Coomassie (but the control lanes 6 & 10 did not glow at 800 nm). This confirmed the presence of both protein and the polymer at the same ordinate in the conjugate samples. To confirm that the copolymer 10 was indeed chemically bonded to the protein, we incubated the mixture of copolymer 10 and modified BSA 13 in the same ratio but without the "click" reagents and dialyzed the mixture with a 50 KDa MWCO membrane; in this case no higher molecular weight conjugate bands were observed (lane 6).

Applications

UV and Fluorescence Study.

Figure 3A:
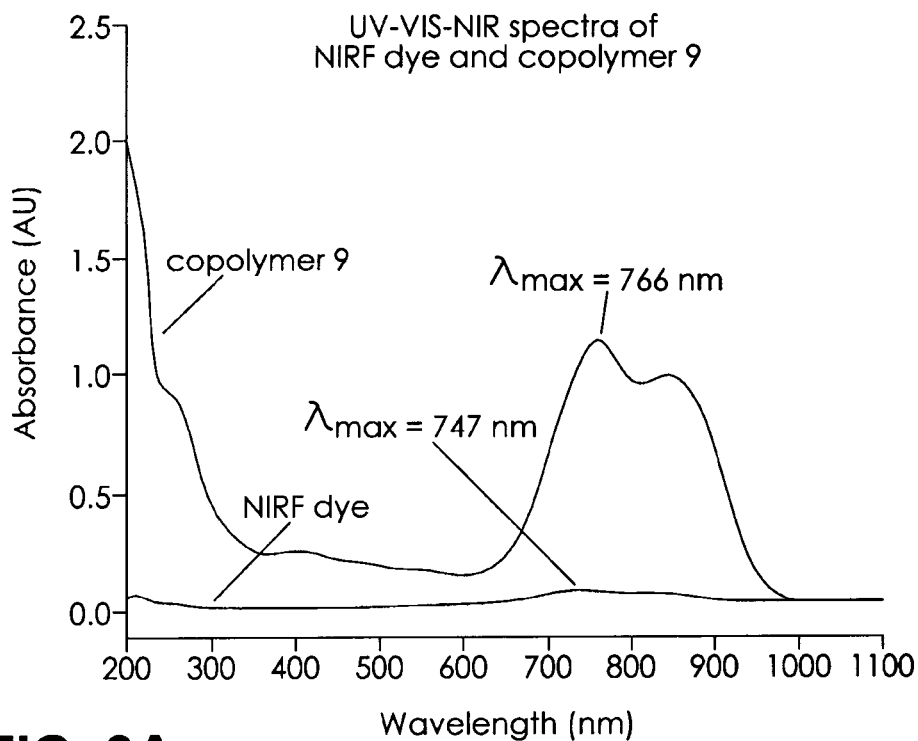
FIG. 3 is a UV/Vis/NIR absorption spectra (A) and Fluorescence emission spectra (B) of NIRF copolymer 9 (blue line), NIRF dye (red line) in water at 25° C. The effective dye concentrations in both the cases are identical (0.3 µM).
Figure 3B:
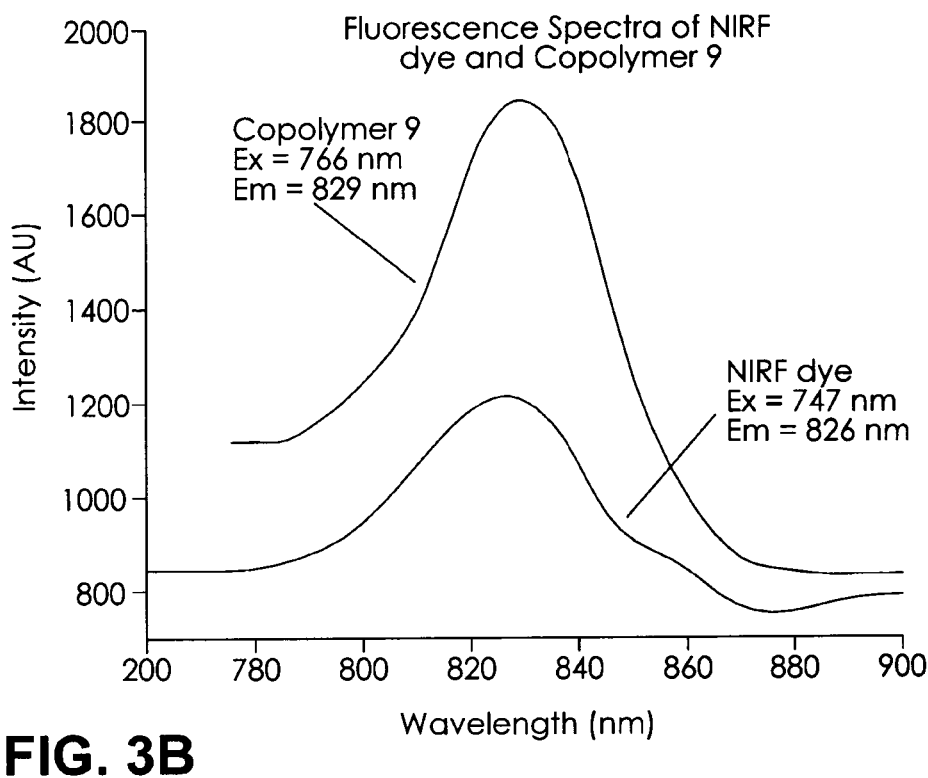

We have investigated the absorbance and the fluorescence emission profiles for the NIRF dye (ADS832WS) and the poly(glucosamine)-poly(NIRF dye) copolymer 9 (FIG. 3). The copolymer 9 had superior solubility in water compared to the dye molecule. As a result higher absorbance values were observed in the case of the polymer sample even though both the solutions contained the same effective dye concentration of 0.3 µM (FIG. 3A). A red shift of 19 nm (from 747 nm to 766 nm) in the absorbance maxima ($\lambda_{max}$) of the dye was also observed. Although the fluorescence emission intensity of copolymer 9 was higher than the dye as expected, the dye displayed larger Stokes shift (79 nm) compared to copolymer 9 (63 nm) (FIG. 3B).

Multiwell Plate Binding Assay

Figure 4:
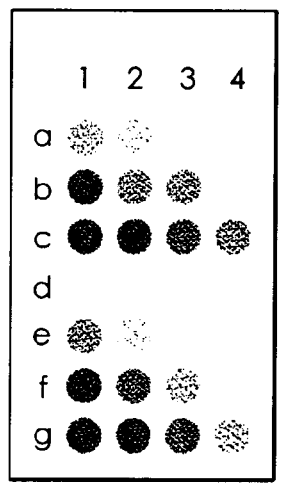
FIG. 4 is a streptavidin coated multiwell plates treated with non-biotinylated copolymer control (a&e), polymer 6a (b&f) and copolymer 6 (c&g).
Figure 5A:
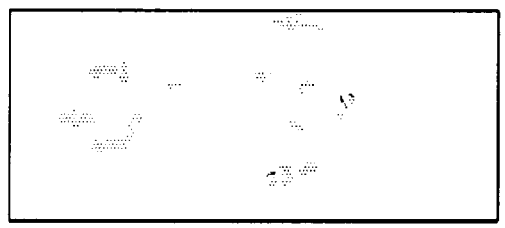
FIG. 5 A shows the control mouse without an imaging agent.
FIGS. 5B & 5C show mouse scanned 1 h and 4 hs after tail-vein injection with the NIRF dye respectively.
FIGS. 5D & 5E show mouse scanned 1 h and 4 hs after tail-vein injection with the copolymer 6 respectively. All the images were scanned using an odyssey NIRF imager at 800 nm.
Figure 5B:
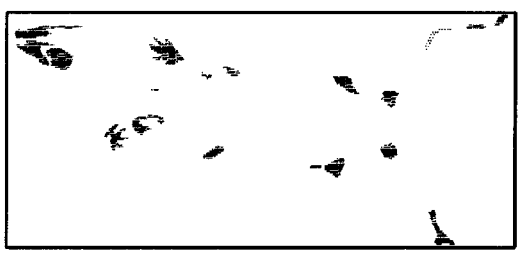
Figure 5C:
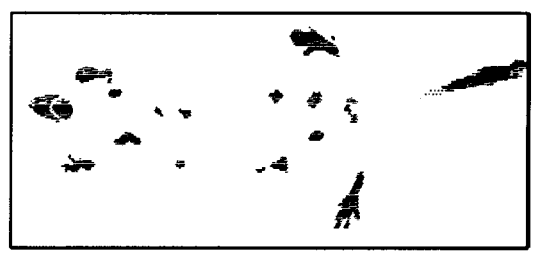
Figure 5D:
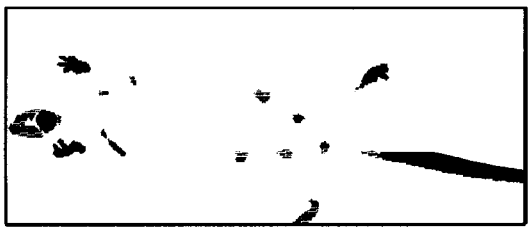
Figure 5E:
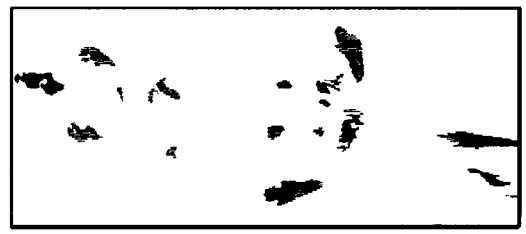

The polymer bioconjugates can be immobilized on plates and then can be used to react with complementary cell surface receptors/lectins to study receptor interactions for diagnostic purposes; the use of these constructs for such applications is covered in this patent. For example Streptavidin coated multiwell plates from Sigma were incubated with a 10 fold serial dilution of (a) control poly(D-Glucosamine)-poly (NIRF) polymer without biotin (b) biotin terminated poly(acrylic acid)-poly (NIRF) polymer and (c) biotin terminated poly(D-Glucosamine)-poly (NIRF) polymer. The dye concentration in the case of all the polymers was identical. The wells were washed multiple times with buffer to avoid non specific binding and scanned using Odyssey NIRF imaging system at 800 nm. It is evident from FIG. 4 that the control polymer without biotin does not bind to the plates (low fluorescence intensity). The biotin terminated polymers remain bound to the streptavidin coated plates as indicated by the fluorescing wells. In case of biotin terminated poly(D-Glucosamine)-poly (NIRF) polymer, the fluorescence intensity is higher than the biotin terminated poly(acrylic acid)-poly (NIRF) polymer because of the superior water/buffer solubility of the former polymer. The synthetic technology is general; as the amine of any carbohydrate can be attached to polymer 4 followed by NIRF dye attachment in accordance with Scheme 12 to produce a range of biotin terminated polymers. These polymers can be immobilized using the streptavidin coated well plates; other ligand protein interactions can be exploited for the same application. The resulting immobilized neoglycopolymers will interact with complementary cell surface receptors/lectins creating a convenient platform to study carbohydrate-receptor interactions, the use of the polymers described in Schemes 8, 9 and 11 are covered in this patent application.

Non Invasive In Vivo Imaging and Imaging of Gels

The use of the polymers and conjugates described in Schemes 1-13) for imaging gels including but not limited to SDS PAGE GELS and DNA gels for both staining and visualization applications is covered in this patent. We also cover the use of the polymers described in Schemes 1-13) for use the non invasive imaging of animals including but not limited to mice and rabbits and for both clinical imaging of humans.

We also cover the use of the polymers and conjugates described in Schemes 1-13 for the detection of pathogens including viruses, bacteria and fungi are covered in this application. We also cover the use of polymers and conjugates described in Schemes 1-13 for use in imaging tissues and tissue sections including all tissues from mammalian and non mammalian sources. We also cover in this patent application the use of the use of the polymers and conjugate described in Schemes 1-13 for imaging cells both in cell culture and immobilized cells of both mammalian and non mammalian cells. The imaging methods include but are not limited to NIRF imaging, confocal microscopy, fluorescence microscopy, MRI imaging, imaging of radioactive species, imaging using a flow cytometer, standard gel imaging using equipment such as Imagquant 300 from GE, photography, in vivo imaging using equipment such a Multispectral System FX from Kodak.

For example mice injected with the biotin terminated poly (D-Glucosamine)-poly (NIRF) polymer, could be imaged (at 800 nm using an Odyssey imaging system) more efficiently than mice injected with the small molecule NIRF—$NH_2$ dye (FIG. 5). It must be noted that the mice were not shaved, only areas in which there was no hair (mouth, feet and tail) glow. The polymer is superior for imaging mice compared to the low molecular weight dye probably because of the superior solubility of poly(glucosamine)-poly(NIRF dye) copolymer 6 in water/blood/serum compared to the dye and because it is not cleared from the blood rapidly via kidney filtration.

Cell Surface Imaging Using Retinal Epithelial Cells

Figure 6:
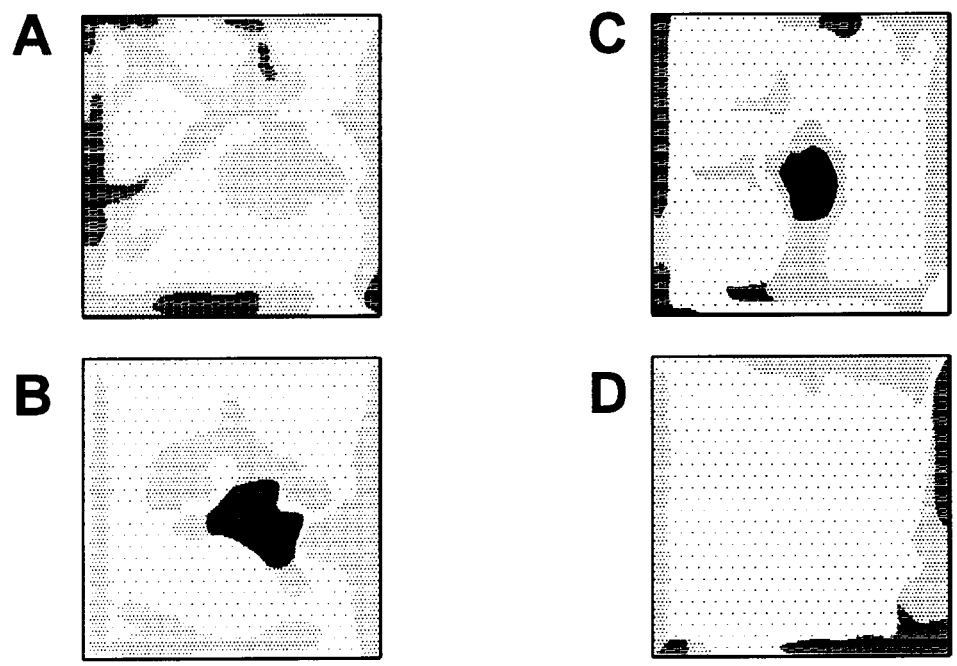
FIG. 6 shows fixed retinal pigment epithelial cells (ARPE-19) labeled using copolymer 6. Slide a was incubated with primary, secondary antibody, avidin and copolymer 6 and imaged. Primary antibody was omitted in slide b, in slide c the primary and secondary antibodies were omitted, in slide d the primary, secondary antibodies and avidin were omitted prior to the copolymer 6 treatment step.
Figure 10:
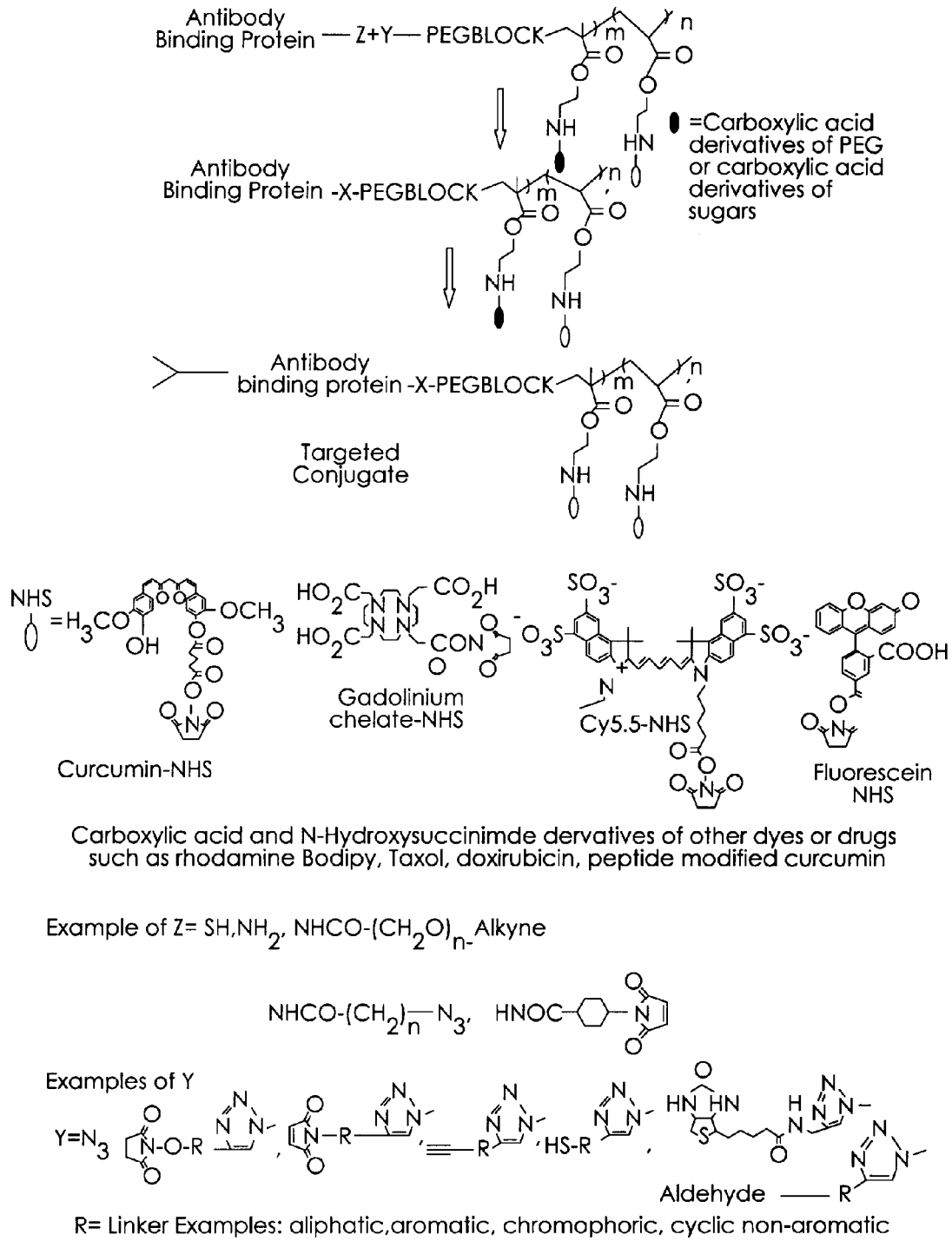
FIG. 10 (Scheme 4) shows a representation of antibody binding protein-copolymer conjugates.
Figure 11:
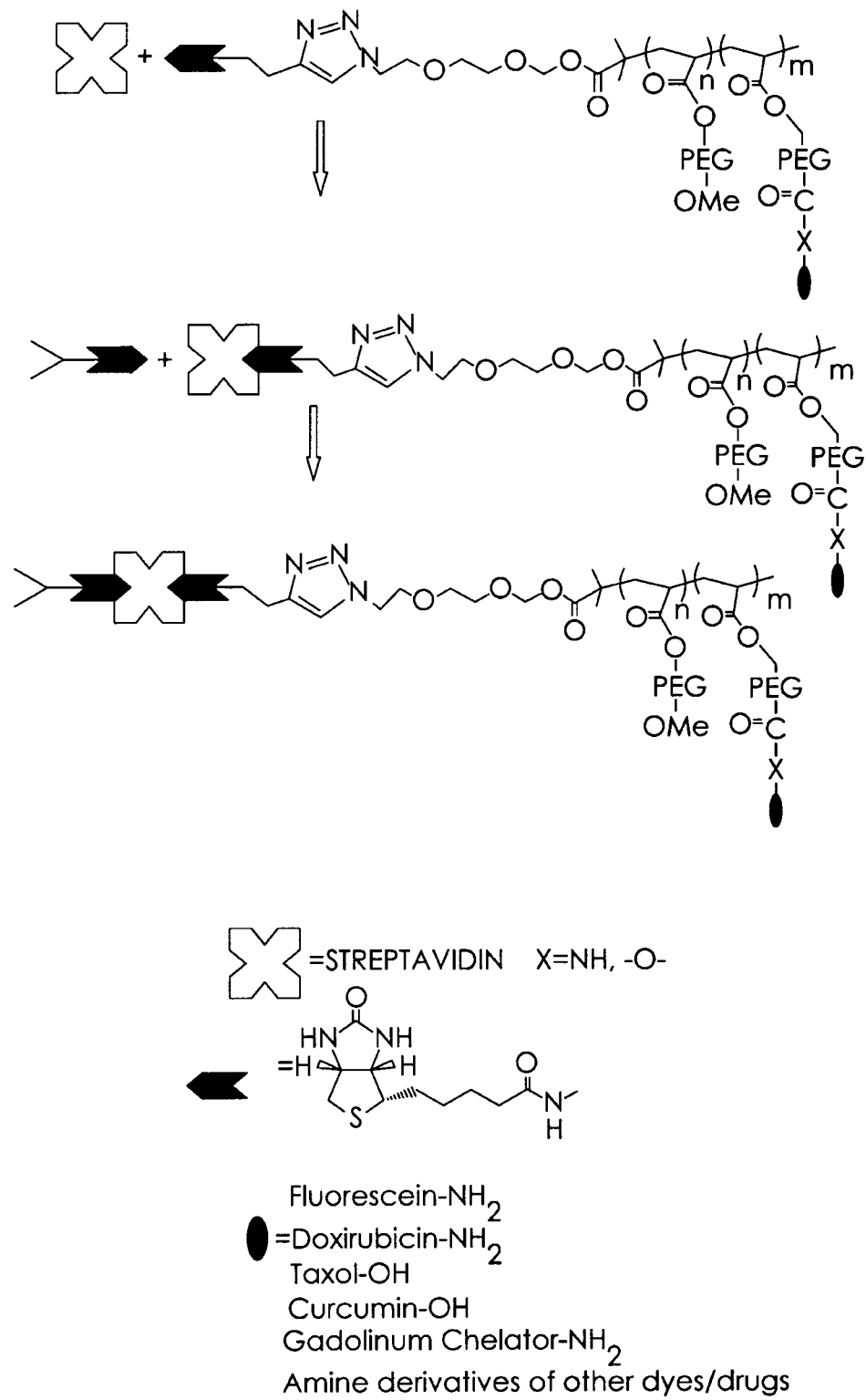
FIG. 11 (Scheme 5) shows a biotinylated antibody-avidin/streptavidin-biotinyltaed copolymer hybrids.
Figure 12:
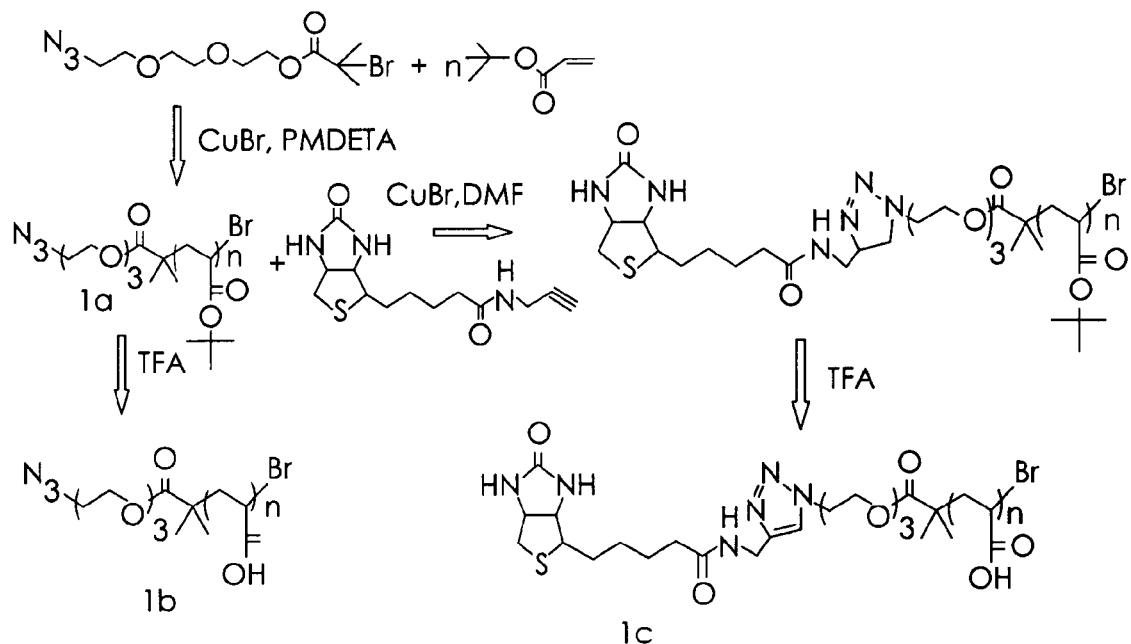
FIG. 12 (Scheme 6) shows a synthesis of poly(acrylic acid) with single reactive chain end.
Figure 13:
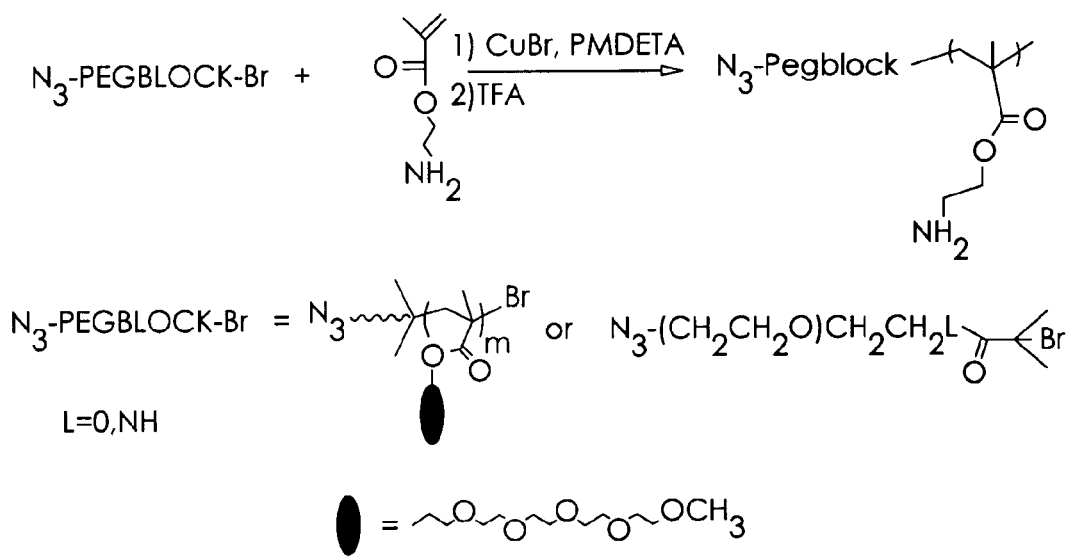
FIG. 13 (Scheme 7) shows a synthesis of polymer with amine side chains and azide chain end.
Figure 15:
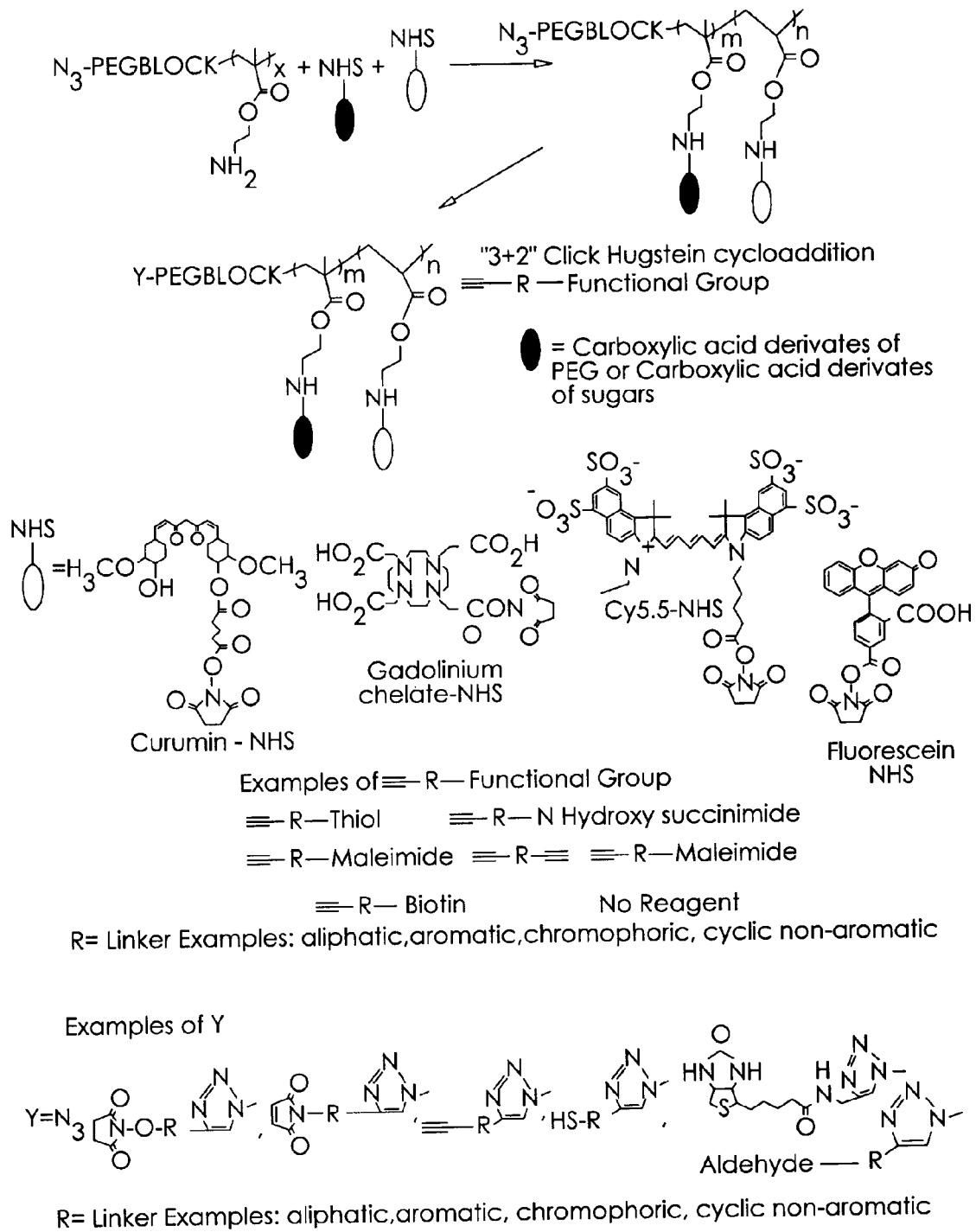
FIG. 15 (Scheme 9) shows a synthesis of copolymers based on side chain amine copolymers.
Figure 17:
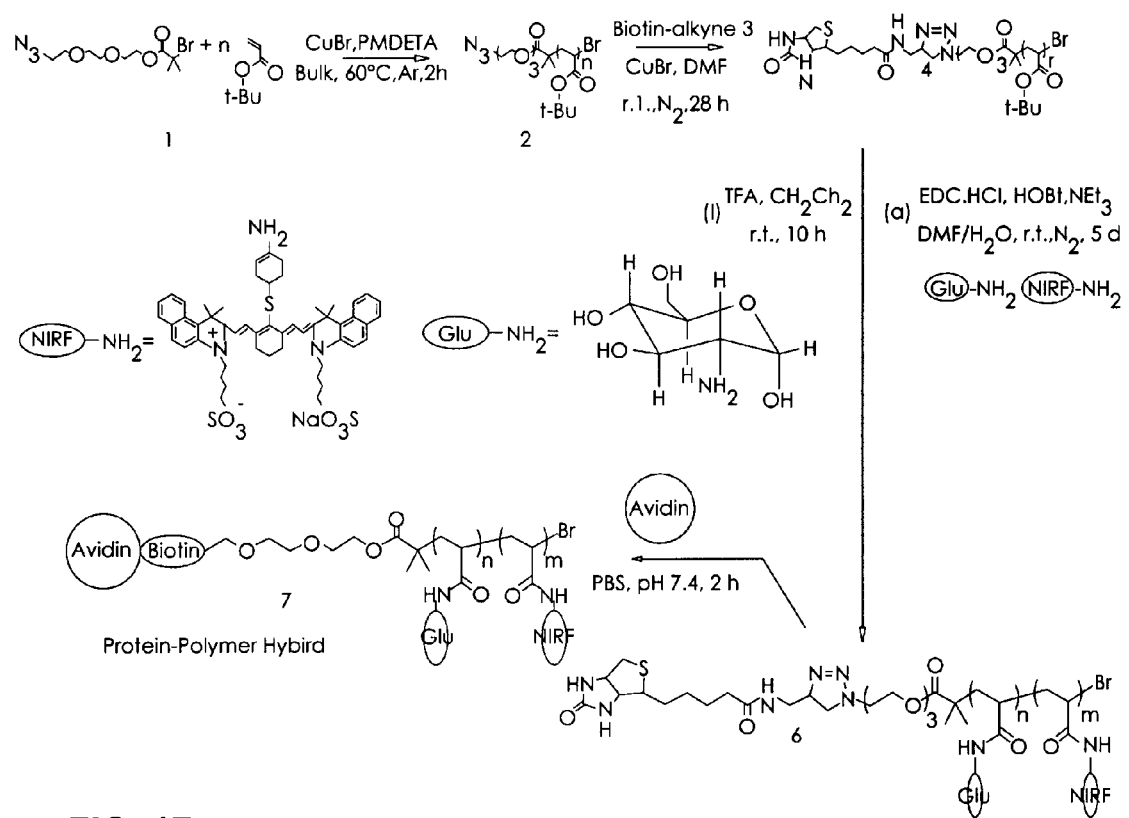
FIG. 17 (Scheme 12) shows a schematic synthesis of NIRF dye incorporated synthetic polymer-protein hybrid via biotin-avidin interaction.
Figure 18:
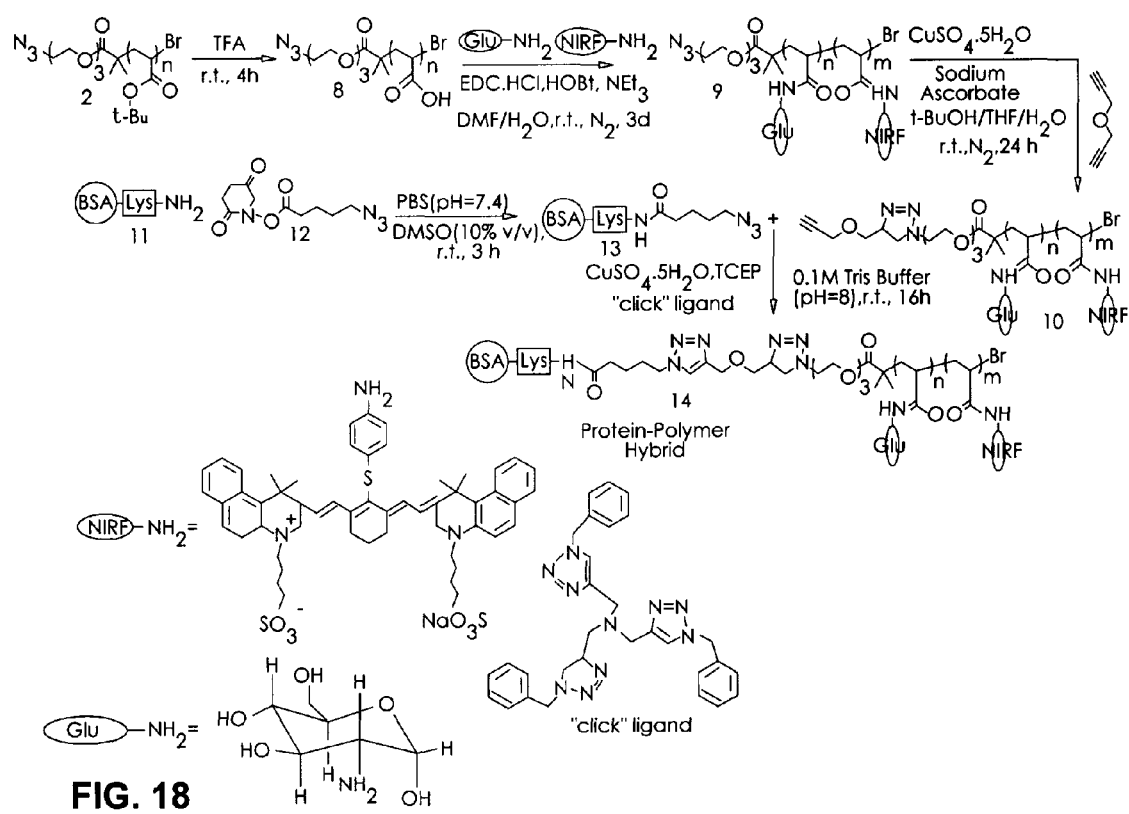
FIG. 18 (Scheme 13) shows a synthetic representation of protein-polymer hybrid via bio-orthogonal "click" reaction with NIRF dye incorporated living copolymer and BSA.
Figure 19:
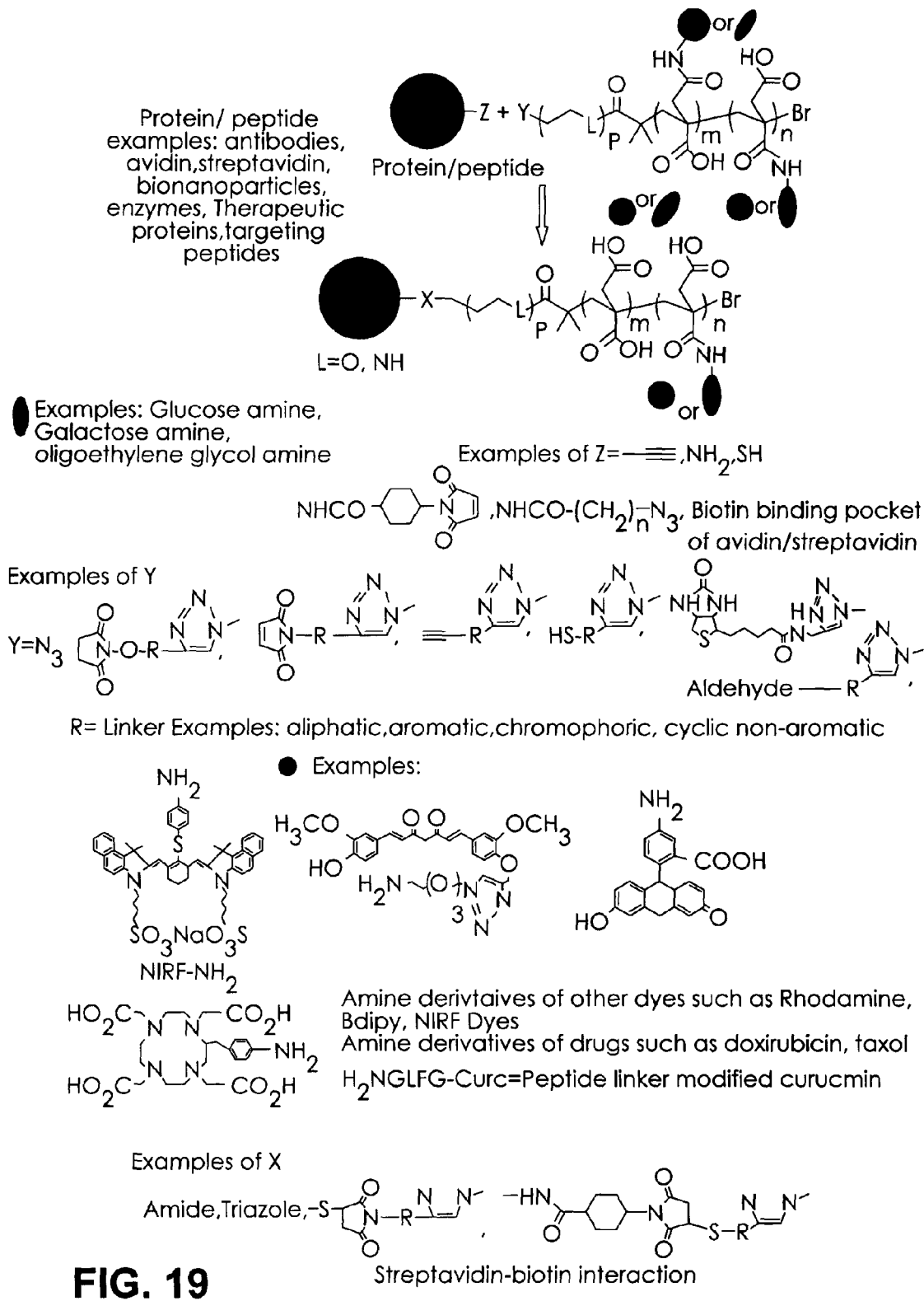
FIG. 19 (Scheme 14) shows a synthesis of itaconic anhydride copolymer-protein conjugate.

An example of the utility of these polymers in visualizing cells is provided by using the biotin terminated poly(D-Glucosamine)-poly (NIRF) polymer (Scheme 8) in imaging retinal pigment epithelial cells. The cells (FIG. 6a) were fixed and treated with primary antibody (2B-α5 Rabbit polyclonal IgG) which binds cell surface proteins; this was followed by incubation with a biotinylated secondary antibody and then avidin. Avidin has four binding sites for biotin; we expected that after attachment to the biotinylated secondary antibody there would still be vacant biotin binding sites available for the NIRF polymer with biotin chain end. After each incubation step the cells were washed thoroughly to minimize non specific binding. The cells were then incubated with polymer and then washed with buffer to prevent non specific binding and the final polymer treated sample was imaged using an odyssey NIRF imager at 800 nm (FIG. 6). Slides b, c and d serve as controls: in slide b the primary antibody was omitted, in slide c the primary and secondary antibody were omitted, in slide d the primary, secondary antibody and avidin were omitted prior to the polymer treatment step. The results show that only the slide which was incubated with primary, secondary antibodies, avidin, and the polymer (slide a) showed maximum fluorescence, while slides (b, c and d) show very little fluorescence (an odyssey NIRF imaging system was used to image the cells). The results show that these polymers and the other polymers and conjugate described in Schemes 1-13 and covered in this patent application are attractive in vitro cell imaging.

The availability of polyclonal antibodies with exquisite specificity to a wide range of analytes has lead to the development of a large number of reagents for immunoassays, targeting and detection [33]. Only a limited number of dyes/other small molecules can be attached per antibody without blocking the antigen binding sites. The attachment of the Copolymers outlined in Schemes 8, 9, 11 with unique NHS ester group/aldehyde group/azide/thiol/alkyne to both primary and secondary antibodies is covered in this patent. The technology developed is very general a wide range of antibody polymer hybrids with amplified detection/therapeutic efficiency outlined in Schemes 1,2,3,4 are covered in this patent application. The amplification arises from the fact that each polymer has several copies of dye/drug molecules attached; on a per antibody basis many more dyes/drugs can be targeted.

TABLE 2

CHEMICAL STRUCTURES OF COMMERCIALLY AVAILABLE LINKERS AND MONOMERS 1. itaconic anhydride

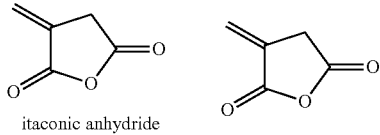

itaconic anhydride 2. glycidyl methacrylate (any methhacrylate with a side chain epoxy group)

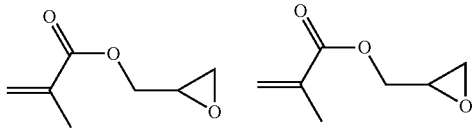

glycidyl methacrylate 3. 2-hydroxyethyl acrylate

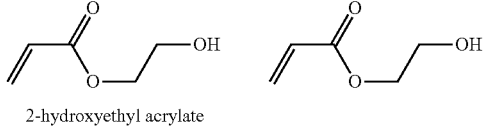

2-hydroxyethyl acrylate

TABLE 2-continued
CHEMICAL STRUCTURES OF COMMERCIALLY AVAILABLE LINKERS AND MONOMERS
EDC,
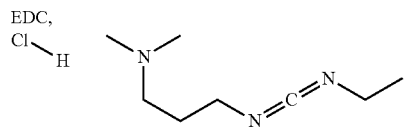
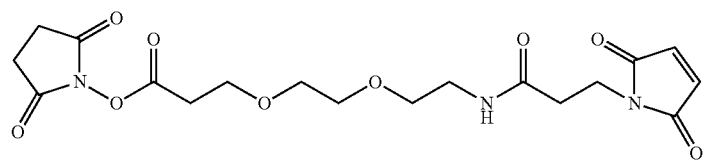 [SMILES: O=C(CCN1C(=O)C=CC1=O)NCCOCCOCCC(=O)ON1C(=O)CCC1=O]
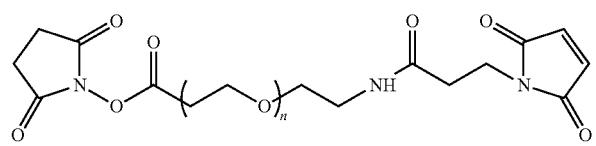
n = 2, 4, 6, 8, 12, 24, ...
Amine-to-sulfhydryl crosslinkers with polyethylene glycol (PEG) spacer arms.
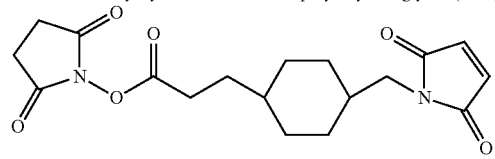
SMBP
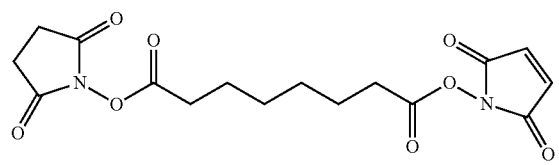
DSS
(AMAS)
α-Maleimidoacetic acid-NHS
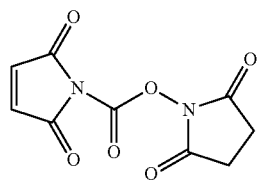 [SMILES: O=C1CCC(=O)N1OC(=O)N1C(=O)C=CC1=O]
2-Maleimidoethyl amine
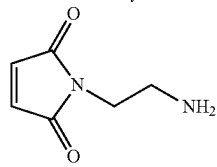
Maleimido acid NHS
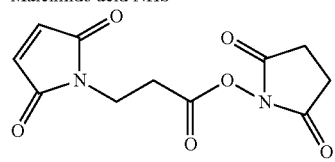

TABLE 2-continued

CHEMICAL STRUCTURES OF COMMERCIALLY AVAILABLE LINKERS AND MONOMERS

3-Maleimidopropionic acid-PFP ester

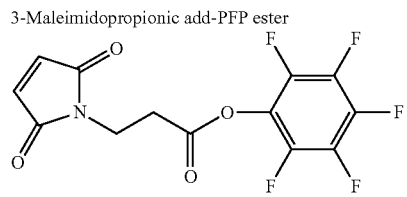

LC-EMCS;
6-[N-(6-Maleimidocaproyl)]caproic acid NHS

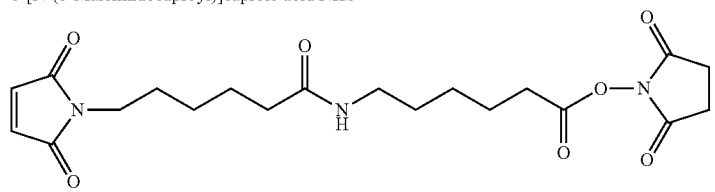

(sulfo-EMCS);
6-Maleimidocaproic acid sulfo-NHS

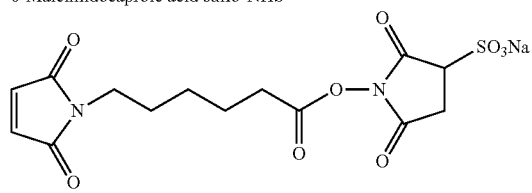

(Mal-cap-NPSA);
6-Maleimidocaproic acid (2-nitro-4-sulfo) phenyl ester sodium salt

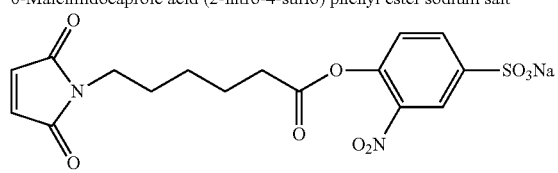

(sulfo-KMUS);
11-Maleimidoundecanoic acid sulfo-NHS

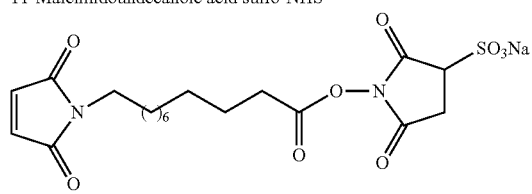

(SMPH);
Succinimidyl 6-[(3-maleimido)propionamido]-hexanoate

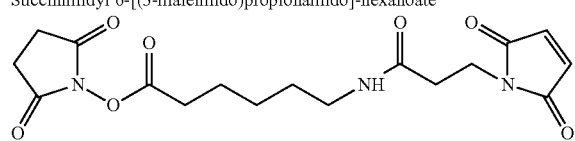

LC-SMPH

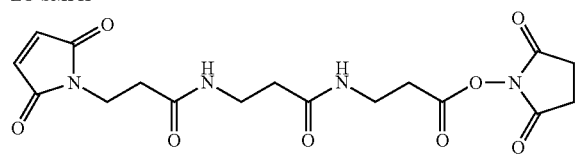

TABLE 2-continued
CHEMICAL STRUCTURES OF COMMERCIALLY AVAILABLE
LINKERS AND MONOMERS
Maleimido alkyl-acid hydrazide
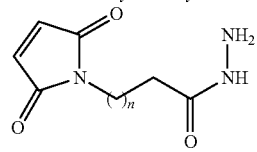
n = 1, 4, 9
Maleimido alkyl-acid
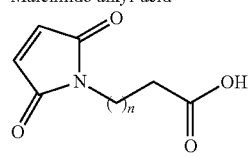
n = 1, 2, 4, 9, ...
SMCC
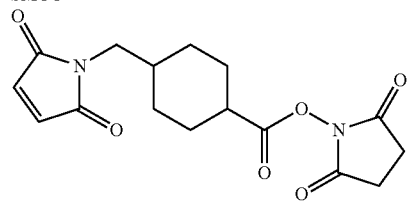
sulfo-SMCC
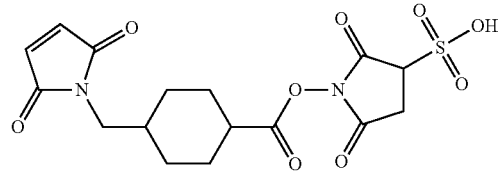 [SMILES: O=C(ON1C(=O)CC(S(=O)(=O)O)C1=O)C1CCC(CN2C(=O)C=CC2=O)CC1]
SMCC hydrazide
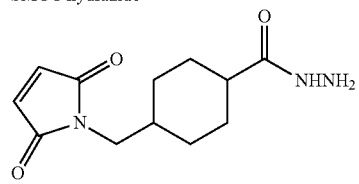
LC-SMCC
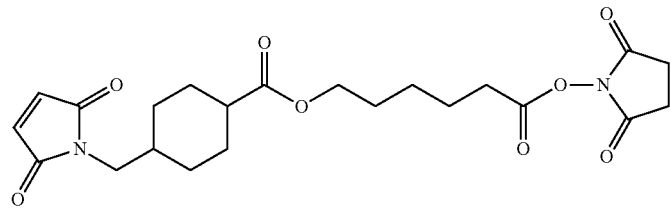 [SMILES: O=C(CCCCCOC(=O)C1CCC(CN2C(=O)C=CC2=O)CC1)ON1C(=O)CCC1=O]
(MBS-1)
m-Maleimidobenzoyl N-hydroxysuccinimide
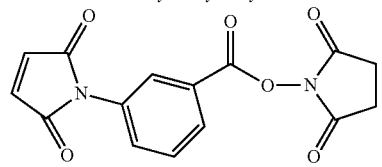

TABLE 2-continued

CHEMICAL STRUCTURES OF COMMERCIALLY AVAILABLE LINKERS AND MONOMERS sulfo-MBS-1

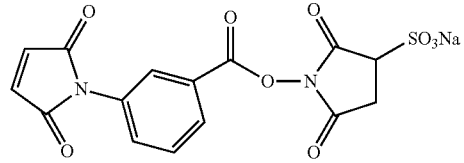

(MBS-2);
p-Maleimidobenzoyl N-hydroxysuccinimide

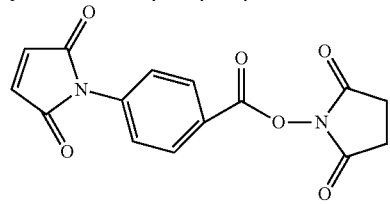

(SVSB)
Succinitnidyl-(4-vinylsulfonyl)benzoate

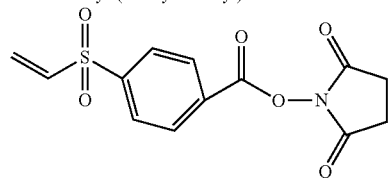

(SIAB);
N-succinimidyl-(4-iodoacetyl) aminobenzoate

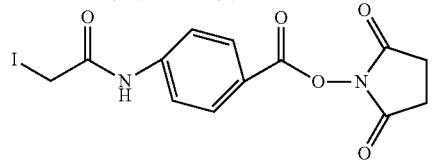 [SMILES: O=C(CI)Nc1ccc(C(=O)ON2C(=O)CCC2=O)cc1]

sulfo-SIAB

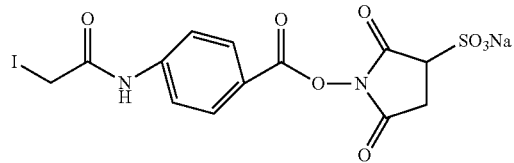

(PMPI);
p-Maleimidophenylisocyanate

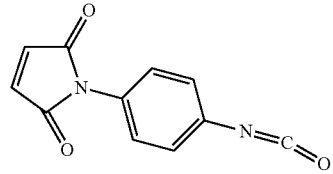 [SMILES: O=C=Nc1ccc(N2C(=O)C=CC2=O)cc1]

(SATA);
n = 1, N-succinimidyl S-acetylthioacetate
(SATP);
n = 2, N-succinimidyl S-acetylthiopropionate

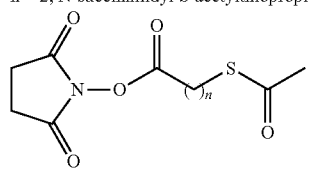

TABLE 2-continued

CHEMICAL STRUCTURES OF COMMERCIALLY AVAILABLE
LINKERS AND MONOMERS (SBAP);
Succinimidyl 3-(bromoacetamido)propionate

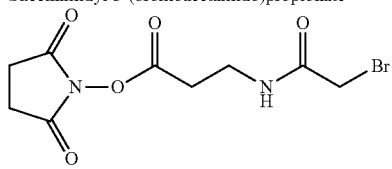

(SIA);
R = I, Succinimidyl iodoacetate
(SBA);
R = 2, Succinimidyl bromoacetate

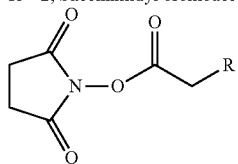

(SMPB)
Succinimidyl 4-(p-maleimidophenyl)butyrate

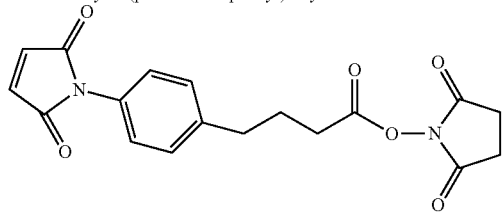

(SFB);
Succinimidyl-p-formyl-benzoate

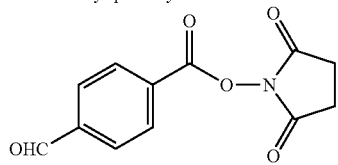

(PDA);
Pyridine dithioethylamine hydrochloride

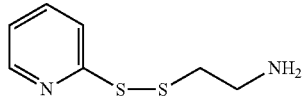 [SMILES: NCCSSc1ccccn1]

4-(N-Maleimido)benzophenone

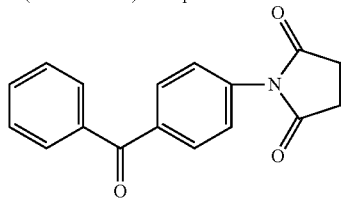

4-(N-succinimidylcarboxy)benzophenone

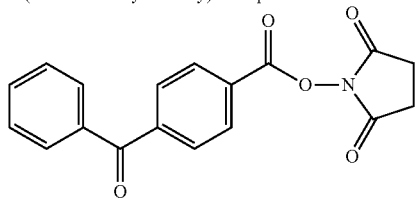

TABLE 2-continued

CHEMICAL STRUCTURES OF COMMERCIALLY AVAILABLE
LINKERS AND MONOMERS 4-(N-iodoacetyl)benzophenone

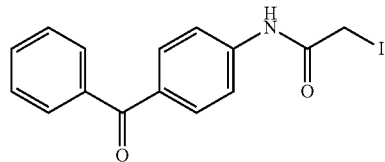 [SMILES: O=C(CI)Nc1ccc(C(=O)c2ccccc2)cc1]

SPDP; 99+ %
(N-Succinimidyl 3-[2-pyridyldithio]propionate)

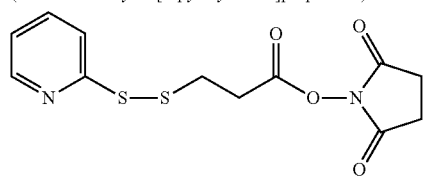

SPDP hydrazide; (PDPH) 99%
(3[2-Pyridyldithio]propionyl hydrazide)

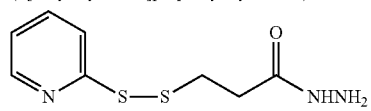

LC-SPDP;
(Succinimidyl 6[3-(2-pyridyldithio)propionamido]hexanoate)

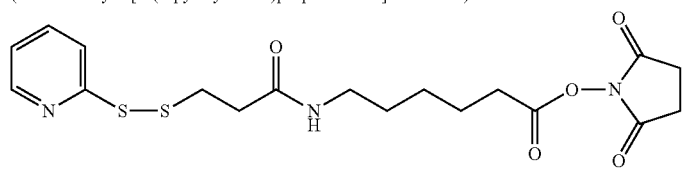

sulfo-LC-SPDP;
(sulfo-Succinimidyl 6-[3-(2-pyridyldithio)propionamido]hexanoate)

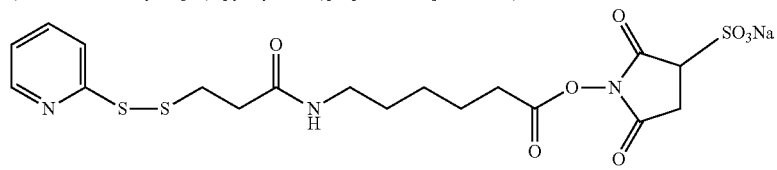

Succinimidyl-4-[2-(tert-butoxycarbonyl)hydrazino]benzoate

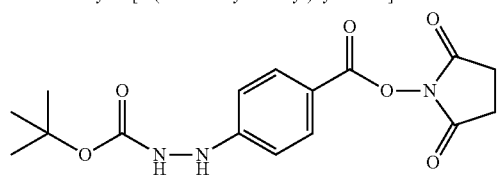

Succinimidyl-4-[2-(tert-butoxycarbonyl)hydrazino]acetate

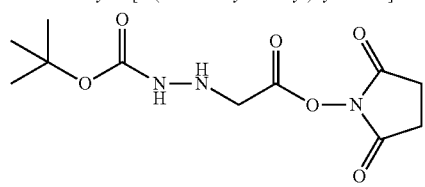

TABLE 2-continued

CHEMICAL STRUCTURES OF COMMERCIALLY AVAILABLE
LINKERS AND MONOMERS

S-Acetylmercaptosuccinic anhydride

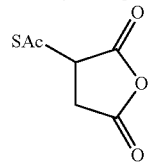

(TFCS);
R = CF$_3$, 6-(N-trifluoroacetyl)caproic acid NHS
(SIAX);
R = I, Succinimidyl-6-(iodoacetyl)aminocaproate
R =

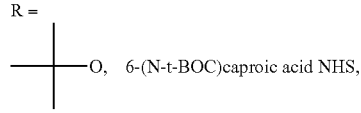

O, 6-(N-t-BOC)caproic acid NHS,

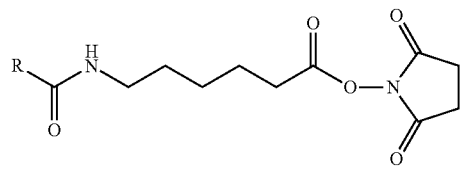

(MSA);
Methyl N-succinimidyl adipate

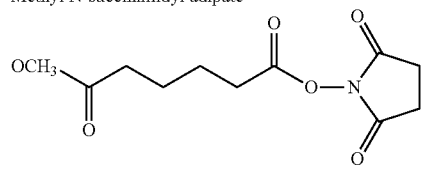

Examples

1. Synthesis of 2-(2-(2-Azidoethoxy)ethoxy)ethanol

Protocol followed from: Sengupta, S., Raja, K. S., Kaltgrad, E., Strable, E. and Finn, M. G. (2005) Virus-glycopolymer conjugates by copper(I) catalysis of atom transfer radical polymerization and azide-alkyne cycloaddition. *Chem. Comm.* 34, 4315-4317.

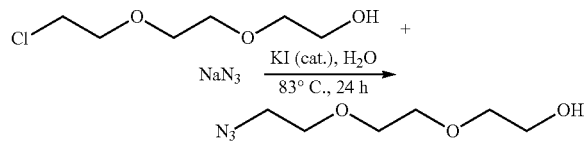

A mixture of 2-(2-(2-chloroethoxy)ethoxy)ethanol (7.04 g, 41.72 mmol), sodium azide (13.65 g, 209.94 mmol) and potassium iodide (1.87 g, 11.25 mmol) in water (72 mL) was stirred at 83° C. for 24 h. The reaction mixture was extracted with ether, and the organic layer was washed with brine and then dried over anhydrous Na$_2$SO$_4$. The solvent was evaporated and the product was dried under vacuum to give colourless oil. The product was purified via column chromatography, CH$_2$Cl$_2$:MeOH, 95:5 was used as the eluent. Yield: 62%. $^1$H NMR (600 MHz, CDCl$_3$): δ (ppm) 2.85-2.87 (t, 2H), 3.29-3.31 (t, 2H), 3.50-3.51 (m, 2H), 3.57-3.64 (m, 6H). $^{13}$C NMR (150 MHz, CDCl$_3$): δ (ppm) 46.58, 57.58, 65.96, 66.31, 66.57, 68.55. ESI-MS m/z=198.1 (M+Na); IR (KBr, cm$^{-1}$) 2104.

Figure 25:
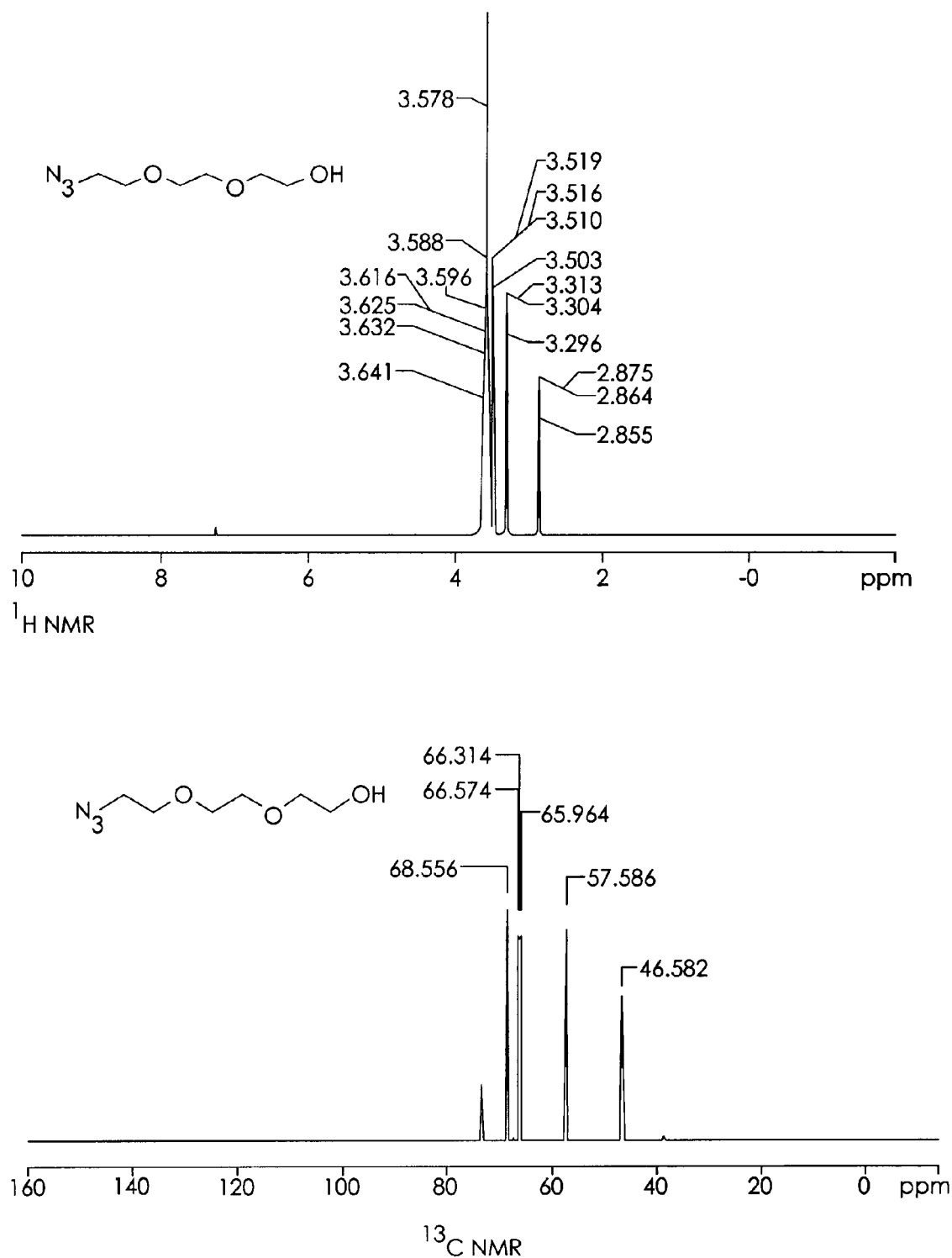

See FIG. 25 for H NMR and $^{13}$C NMR.

2. Synthesis of 2-Bromo-2-methylpropionic acid 2-[2-(2-Azidoethoxy)ethoxy]ethyl ester Protocol followed from: Sengupta, S., Raja, K. S., Kaltgrad, E., Strable, E. and Finn, M. G. (2005) Virus-glycopolymer conjugates by copper(I) catalysis of atom transfer radical polymerization and azide-alkyne cycloaddition. *Chem. Comm.* 34, 4315-4317.

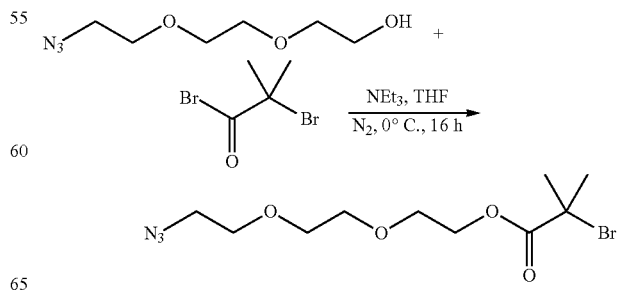

A solution of 2-bromoisobutyryl bromide (4.58 g, 19.9 mmol) and triethylamine (2.18 g, 21.5 mmol) in THF (5 mL) was cooled to 0° C. in a 2-necked round-bottomed flask. A solution of 2-[2-(2-azidoethoxy)ethoxy]ethanol (3 g, 17.1 mmol) in THF (5 mL) was added dropwise with stirring. The reaction mixture was then stirred at room temperature for 16 h, filtered, and the solvent was removed by rotatory evaporator. The crude product was added to a cooled (ice bath) 5% aqueous ($Na_2CO_3$) solution and the resulting mixture was extracted with ethyl acetate (3×50 mL). The combined organic layers were washed with brine, dried over anhydrous ($Na_2SO_4$), and evaporated to provide product as dark-yellow oil. Yield: 5 g (90%). $^1$H NMR (600 MHz, $CDCl_3$): δ (ppm) 1.88 (s, 6H), 3.56-3.58 (t, 2H), 3.63 (s, 4H), 3.69-3.70 (t, 4H), 4.26-4.28 (t, 2H). $^{13}$C NMR (150 MHz, $CDCl_3$): δ (ppm) 30.53, 42.57, 55.54, 64.89, 68.58, 68.60, 70.43, 70.48, 71.15, 171.37.

See FIG. 26 for $^1$H NMR and $^{13}$C NMR.

3. Synthesis of Azide terminated Poly(tert-butyl acrylate)

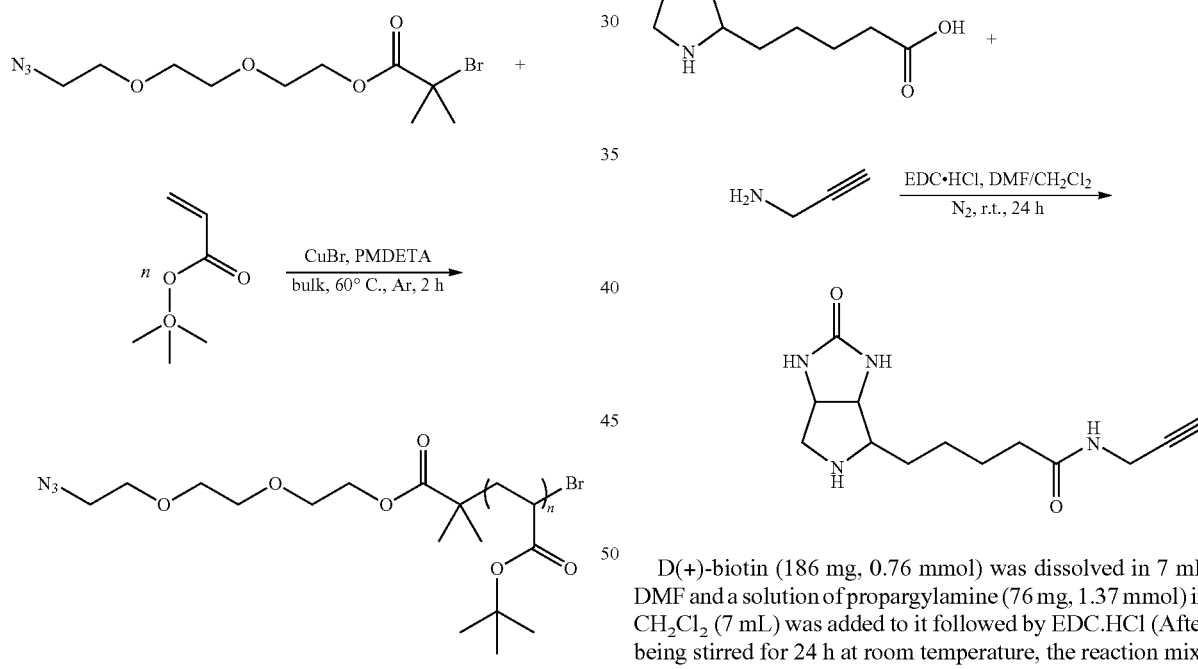

A 100 mL flask fitted with a stopcock was flame-dried under vacuum and allowed to cool at ambient temperature under $Ar_2$. The flask was charged with CuBr (115 mg, 0.8 mmol). Under positive pressure of $Ar_2$, a solution of 2-Bromo-2-methylpropionic acid 2-[2-(2-Azidoethoxy) ethoxy]ethyl ester (118 mg, 0.36 mmol) dissolved in tert-butyl acrylate (4 mL, 27.55 mmol) was added via syringe, followed by the addition of 1,1,4,7,7-pentamethyldiethylenetriamine (PMDETA) (0.17 mL, 0.8 mmol). Following three freeze-pump-thaw degassing cycles, the reaction was allowed to stir for 2 hour 10 minutes at 60° C. The polymerization was quenched by submerging the flask in liquid nitrogen, the mixture was allowed to warm to ambient temperature, and diluted with tetrahydrofuran. CupriSorb® was added and stirred ca. 30 minutes for removing copper complex. After filtration, the mixture was poured into a 15% methanol, deionized water solution, white solid product was precipitated. The polymer was further purified via reprecipitation and dried under vacuum; isolated yield was 2.18 g (47%). $M_n$=8586 g/mol, $M_w/M_n$=1.21. $^1$H NMR (600 MHz, $CDCl_3$): δ (ppm) 4.19 (s, 2H), 3.55-3.75 (m, 6H), 3.39 (t, 2H), 2.18-2.30 (bm), 1.85 (s), 1.28-1.62 (bm), 1.15 (s, 6H), 0.89 (m). FTIR (film, $cm^{-1}$): 3433, 2977, 2289, 2113 (azide), 1727, 1619, 1450, 1367, 1255, 1153, 845, 752.

Figure 27:
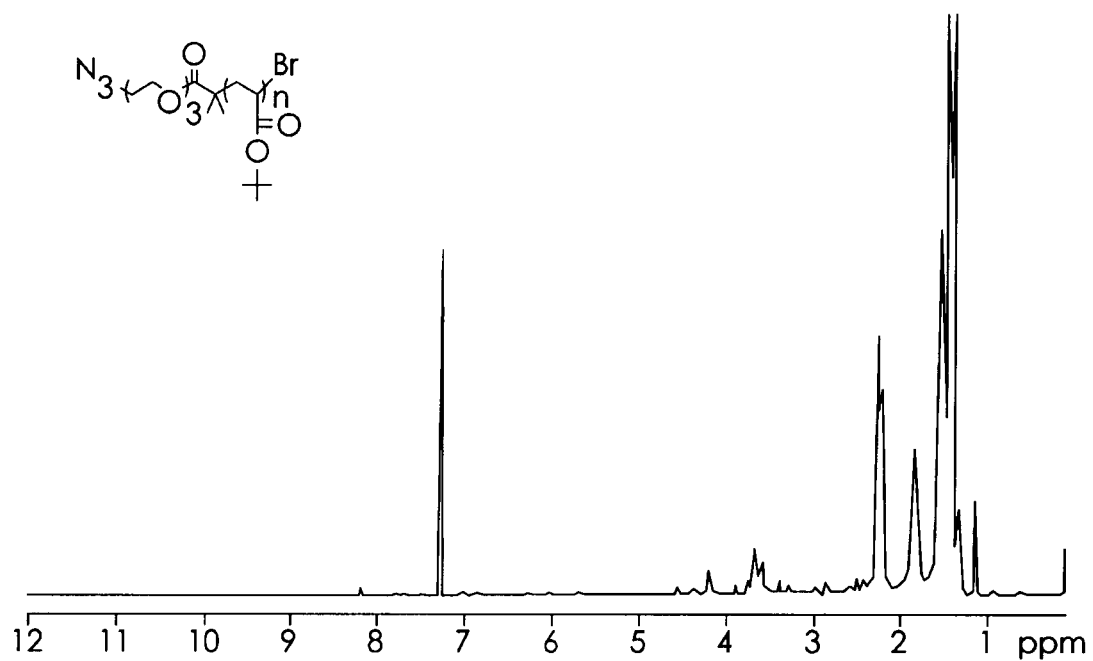
FIGS. 27, 29, 32, 34, 36, 37, 40, 43, 45, 47, 49, 54, 57, 59, 61-66, 67 (top), and 68-70 show $^1$H NMR.
Figure 28:
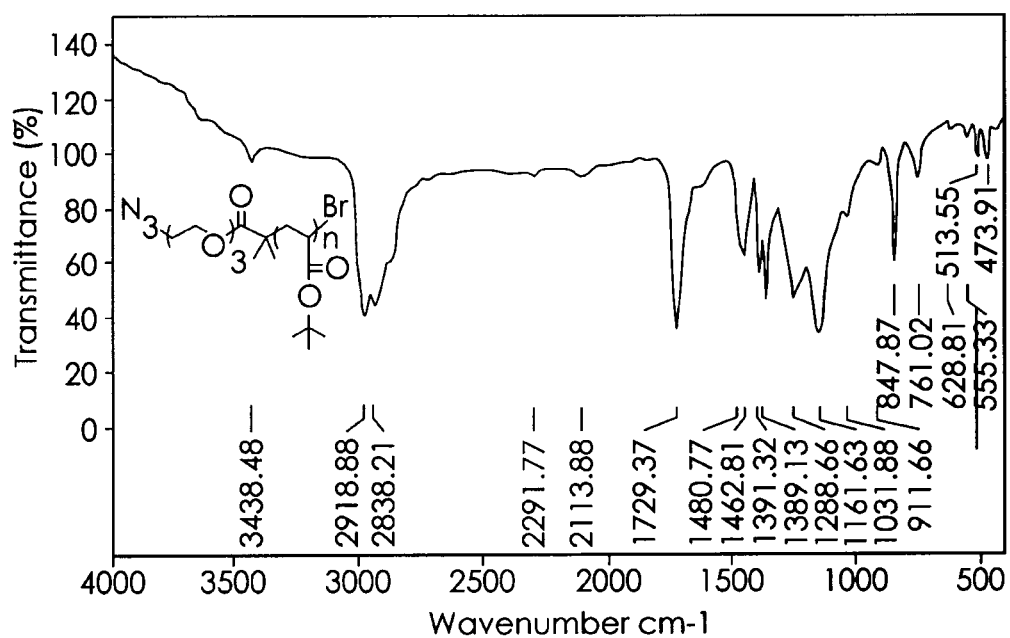
FIGS. 28, 38, 41, 44, 55, 58, and 60 show FTIR.

See FIGS. 27 and 28 for NMR and FTIR.

4. Synthesis of 5-(2-oxooctahydropyrrolo[3,4-d] imidazol-4-yl)-N-(prop-2-yl)pentanamide (Biotin-Alkyne)

D(+)-biotin (186 mg, 0.76 mmol) was dissolved in 7 mL DMF and a solution of propargylamine (76 mg, 1.37 mmol) in $CH_2Cl_2$ (7 mL) was added to it followed by EDC.HCl (After being stirred for 24 h at room temperature, the reaction mixture was concentrated in vacuum and diluted by 30 mL of $CH_2Cl_2$ and the organic layer was washed by water (10 mL×3), dried over $Na_2SO_4$ and then concentrated in vacuum. The crude product was purified by flash column chromatography (MeOH/$CH_2Cl_2$=5/95-15/85) to obtain the product 160 mg (75%). $^1$H NMR (600 MHz, $CD_3OD$): δ (ppm) 4.48-4.50 (dd, 1H), 4.29-4.31 (dd, 1H), 3.94 (d, 2H), 3.19-3.22 (dt, 1H), 2.91-2.94 (dd, 1H), 2.69-2.41 (d, 2H), 2.58-2.59 (t, 1H), 2.20-2.23 (t, 2H), 1.58-1.74 (m, 4H), 1.42-1.46 (q, 2H); $^{13}$C NMR (150 MHz, $CD_3OD$): δ (ppm) 173.6, 164.1, 78.7, 70.1, 61.3, 59.6, 55.0, 39.1, 34.5, 27.7, 27.4, 24.7.

Figure 29:
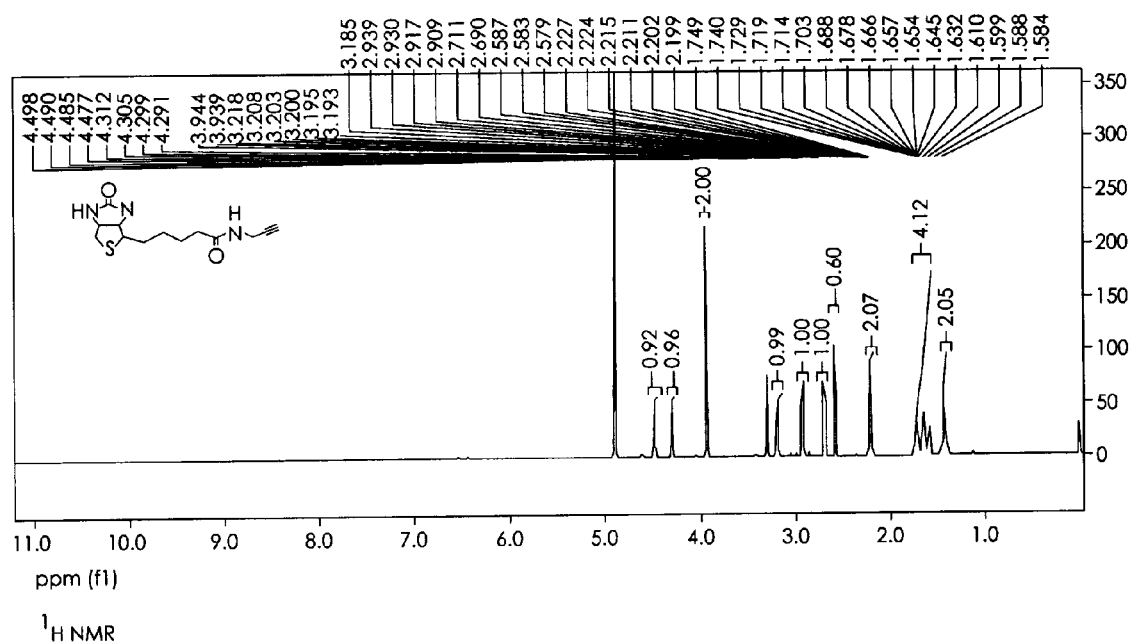
Figure 30:
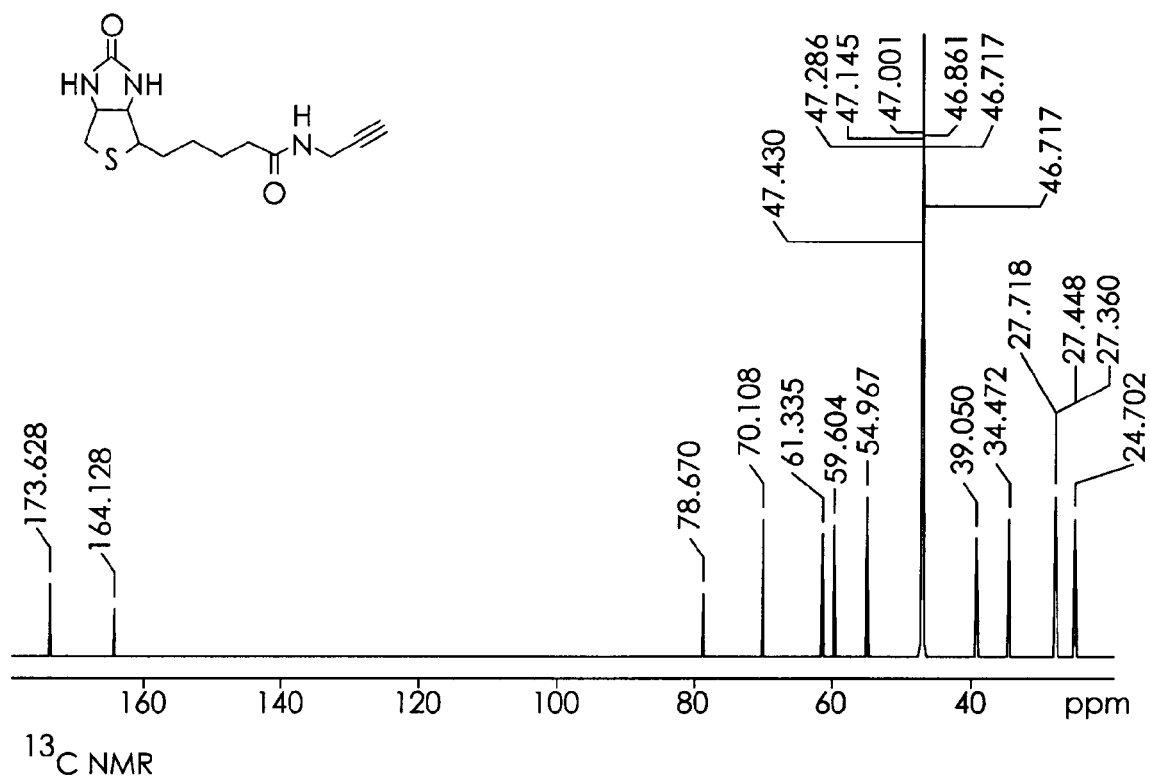

See FIGS. 29 and 30 for $^1$H NMR and $^{13}$C NMR.

5. Synthesis of Biotin Terminated poly(tert-butyl acrylate)

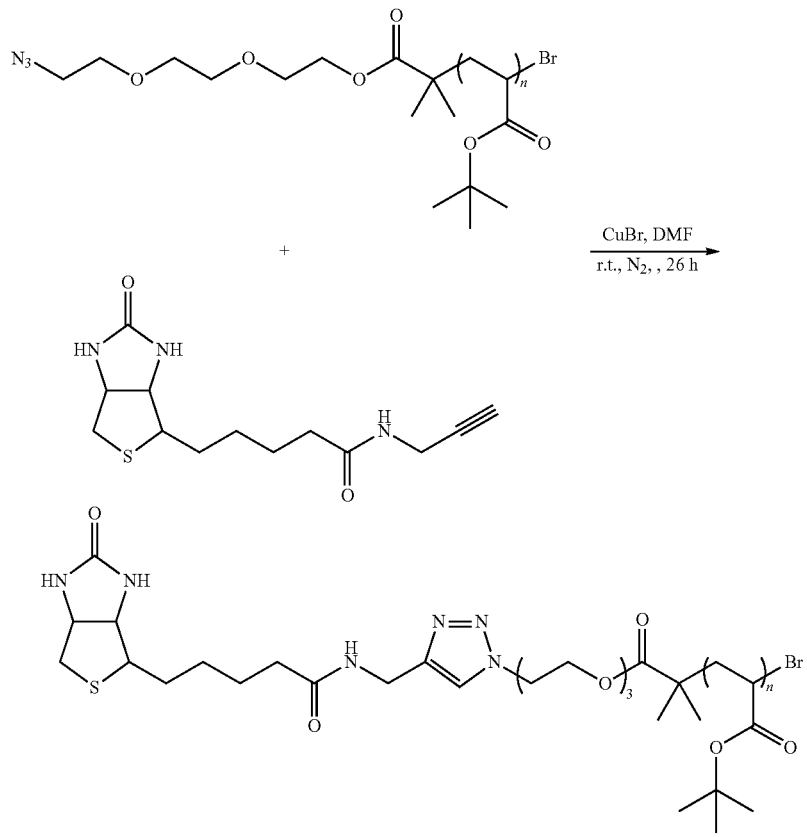

The azide-containing polymer (565 mg, 0.073 mmol of azide groups), biotin-alkyne (25 mg, 0.087 mmol), CuBr (35 mg, 0.024 mmol), and 1,1,4,7,7-pentamethyldiethylenetriamine PMDETA (5.2 µL, 0.025 mmol) were placed in a round-bottom flask. The flask was closed with rubber septum and degassed with $Ar_2$. Deoxygenated DMF (3 mL) was added with an argon-purged syringe, and the reaction was stirred for 26 h at room temperature. The mixture was diluted with tetrahydrofuran, and CupriSorb® was added stirred ca. 30 minutes to remove copper complex. Solid residue was filtered off and the mixture was poured into a 15% methanol, deionized water solution where white solid product was precipitated. The product was further purified by re precipitation and dried over vacuum. Yield: 537 mg (92%). $M_n$=8850 g/mol, $M_w/M_n$=1.30. $^1$H NMR (600 MHz, $CDCl_3$): δ (ppm) 7.68 (s), 7.44 (s), 4.48 (s), 4.31 (s), 4.19 (s), 4.00 (s), 3.3803.64 (m), 3.11 (m), 2.73 (d), 2.18-2.30 (bm), 1.79 (s), 1.28-1.62 (bm), 1.10 (s), 0.89 (m). FTIR (film, $cm^{-1}$): 3433, 2977, 2932, 2720, 2360, 1991, 1728, 1479, 1449, 1392, 1367, 1256, 1150, 1037, 845, 734.

See FIG. 31 for $^1$H NMR and FTIR.

6. Synthesis of Biotin Terminated poly(acrylic acid)

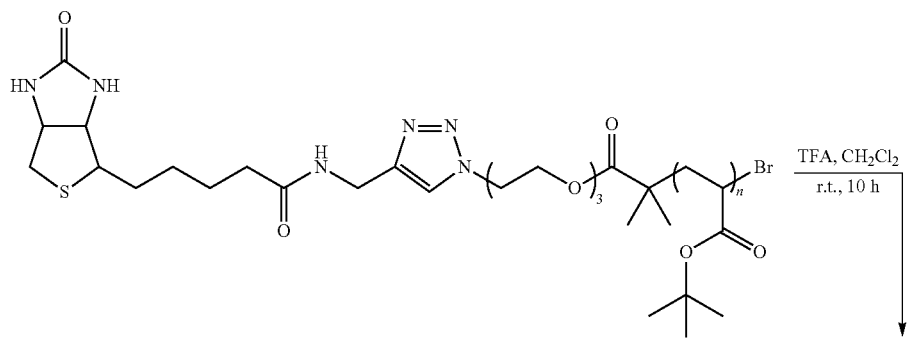

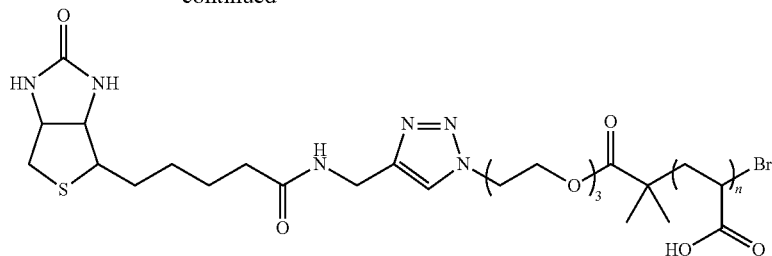

Biotin terminated poly(tert-butyl acrylate) (489 mg, 0.061 mmol) was dissolved in a solution of trifluoroacetic acid (1.5 mL, 19.5 mmol) in dichloromethane (13 mL). The reaction was allowed to stir at ambient temperature overnight. The solvent was removed under vacuum, and the resulting solid was dissolved in deionized water. The solution was transferred to a dialysis bag (MWCO 3.5 KDa), and dialyzed against a continuous flow of deionized water for overnight. The final polymer was isolated by lyophilization: Isolated yield 238 mg, (87%). $^1$H NMR (600 MHz, CDCl$_3$): δ (ppm) 12.23 (bs), 7.85 (s), 7.78 (s), 4.47 (t), 4.26-4.30 (m), 4.04 (b), 3.38-3.82, (bm), 3.23-3.25 (t), 3.08 (s), 2.87 (d), 2.80-2.83 (t), 2.68-2.74 (m), 2.19 (bs), 2.07 (t), 1.74 (bm), 1.22-1.60 (bm), 1.07 (bm), 0.88 (m).

Figure 32:
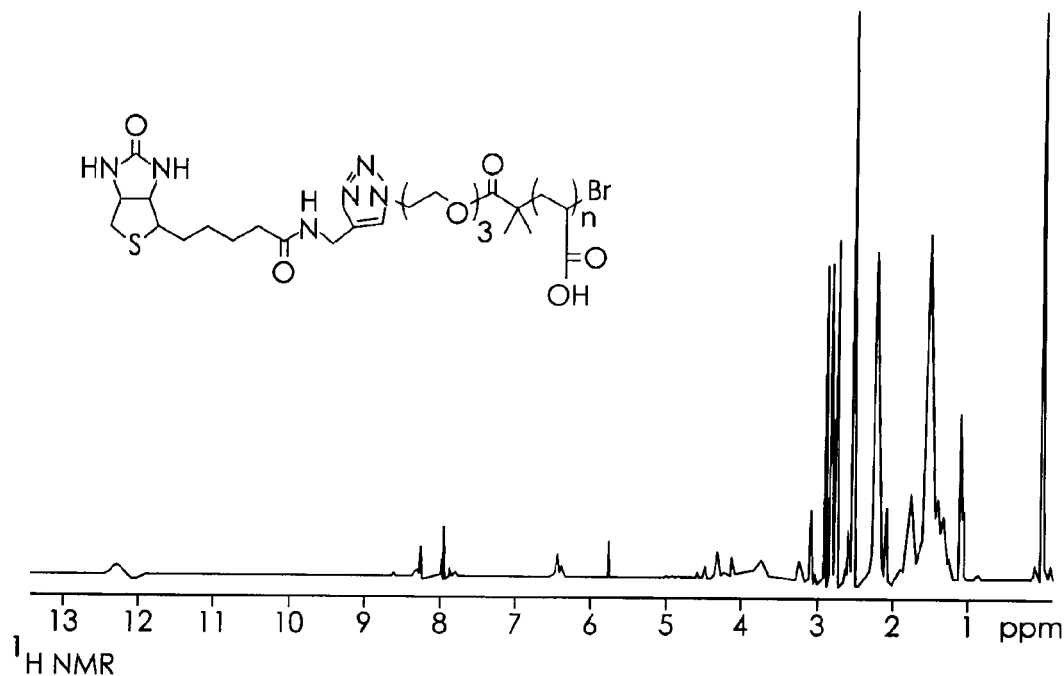

See FIG. 32 for $^1$H NMR.

Figure 33:
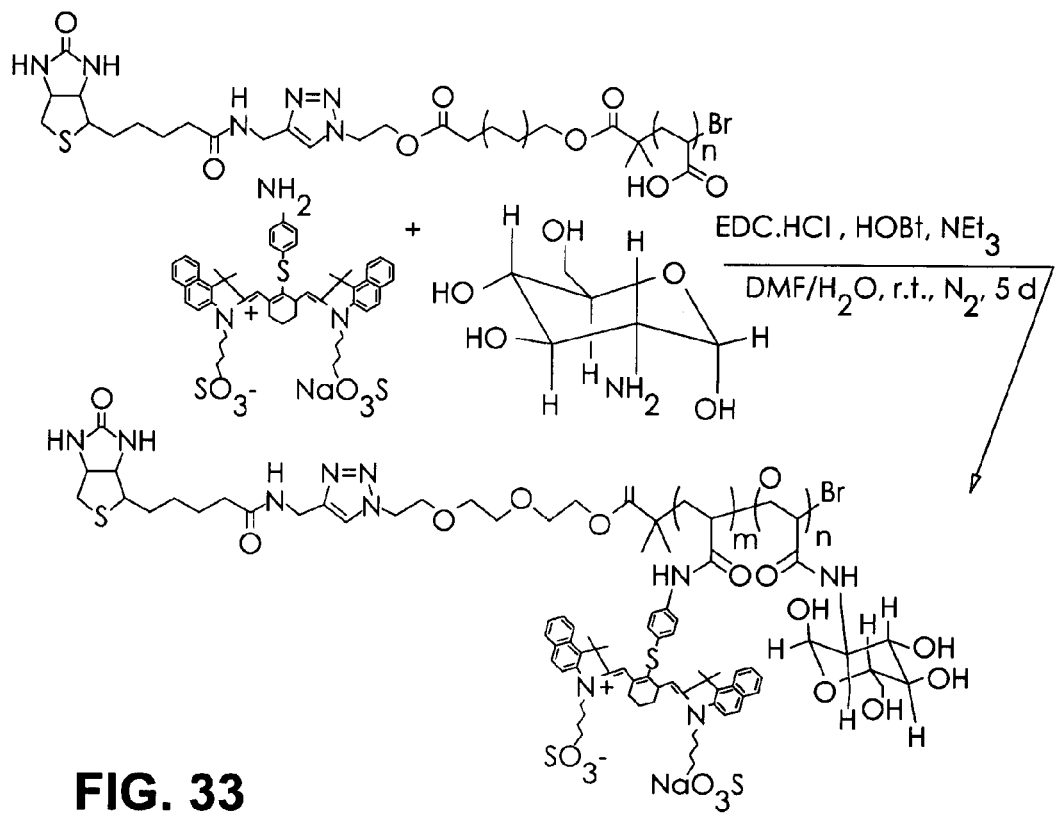
FIG. 33 shows a reaction scheme for Example 7.

7. Synthesis of Biotin Terminated poly(glucosamine)-poly(NIRF dye) copolymer See FIG. 33 for Reaction Scheme.

Biotinylated poly(acrylic acid) (76 mg, 1.055 mmol), Near infrared absorption dye (ADS832WS) (200 mg, 0.213 mmol), EDC.HCl (213 mg, 1.11 mmol), and HOBt (153 mg, 1.148 mmol) were dissolved in DMF (1.5 mL) in a r.b. followed by the addition of Triethylamine (0.15 mL, 1.08 mmol). After stirring for 2 days at room temperature, D(+)-glucosamine (230 mg, 1.067 mmol) (in water (2 mL) and DMF (1 mL) mixture solution) was added. EDC.HCl (200 mg, 1.043 mmol) was added, and the mixture was stirred another 3 day at room temperature. After stopping the reaction, the solution was transferred into a dialysis bag (MWCO 3.5 KDa), and the solution was dialyzed against a continuous flow of deionized water for 24 h. The dialyzed reaction mixture was filtered and lyophilized to yield greenish-brown crude product. The crude product was further purified with Sephadex™ LH-20 size-exclusion column with deionized water as eluent and lyophilized. Isolated yield: 249 mg. $M_n$=23259 g/mol, $M_w/M_n$=1.48. $^1$H NMR (600 MHz, CD$_3$OD) δ (ppm) 8.98 (d), 7.18-8.34 (bm), 6.68 (m), 6.37 (m), 5.27 (d), 4.63 (s), 4.30 (s), 3.31-3.96 (m), 3.19 (m), 3.12 (m), 2.99-3.02 (m), 2.86-2.91 (m), 2.79 (s), 1.35-2.22 (m), 1.61 (d), 1.19-1.32 (m), 1.08 (m).

Comparing the Mn=8850 of biotinylated poly(tert-butyl acrylate) and Mn=23259 of Biotin Terminated poly(glucosamine)-poly(NIRF dye) copolymer, the percent of dyes per polymer chain were calculated: subtracting the mol. wt. of the chain-end groups from Mn of poly(tert-butyl acrylate), the number of repeat units was calculated to be 64, this number was used as the total number of repeat units in the copolymer, employing the following equation the number of dye repeat unit per polymer chain was calculated: ax+b(64−x)=(Mn−c). Where x=number of dyes per polymer chain, a, b & c are mol. wts. of dye repeat unit, sugar repeat unit and chain-ends respectively, and the percentage of dyes per polymer chain was calculated to be ~17.

Figure 34:
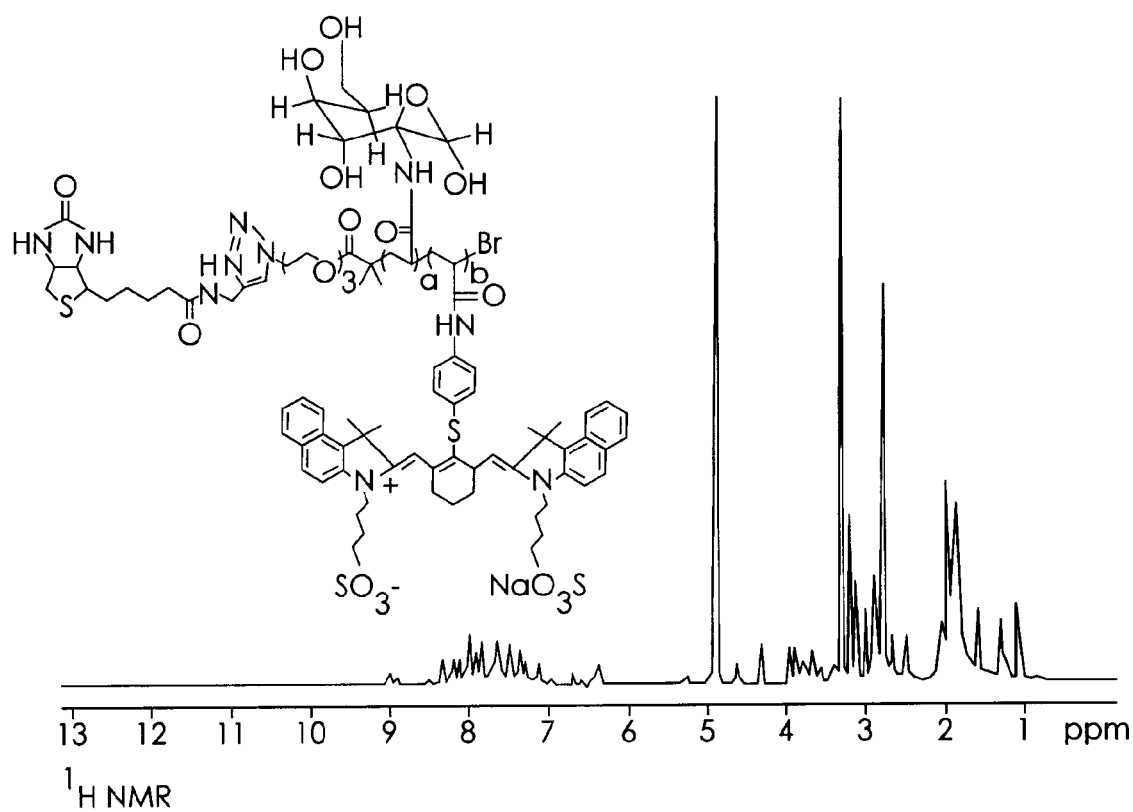

See FIG. 34 for $^1$H NMR.

8. Synthesis of Biotin Terminated Poly(acrylic acid)-poly(NIRF dye)

Figure 35:
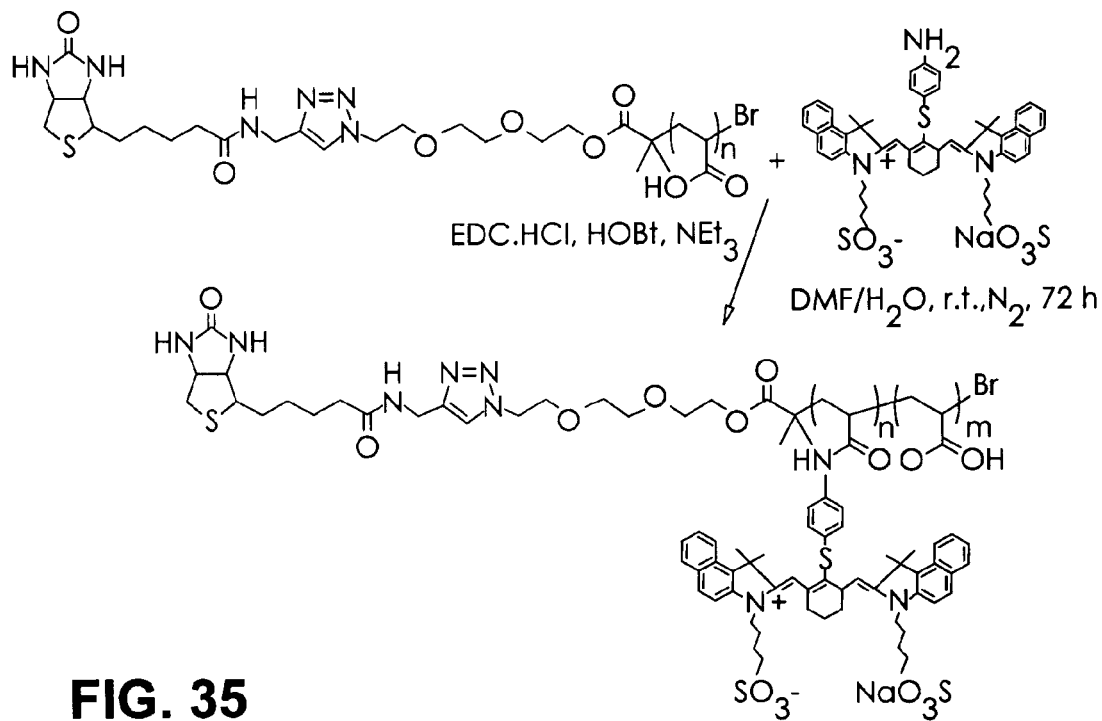
FIG. 35 shows a reaction scheme for Example 8.

See FIG. 35 for Reaction Scheme.

Biotinylated poly(acrylic acid) (76 mg, 1.055 mmol), Near infrared absorption dye (ADS832WS) (498 mg, 0.531 mmol), EDC.HCl (213 mg, 1.11 mmol), and HOBt (153 mg, 1.148 mmol) were dissolved in DMF (1.5 mL) in a r.b. followed by the addition of Triethylamine (0.03 mL, 0.17 mmol). The mixture was stirred 3 day at room temperature. After stopping of the reaction, the solution was transferred into a dialysis bag (MWCO 3.5 KDa), and the solution was dialyzed against a continuous flow of deionized water for 24 h. The dialyzed reaction mixture was filtered and lyophilized to yield greenish-brown cotton shaped crude product. The crude product was further purified with Sephadex™ LH-20 size-exclusion column with deionized water as eluent. Yield: 40 mg. $^1$H NMR (600 MHz, CD$_3$OD): δ (ppm) 8.83 (b), 7.13-8.23 (bm), 6.35 (b), 4.04-4.34 (b), 3.09-3.19 (bm), 2.55-3.07 (bm), 1.02-2.48 (bm).

Figure 36:
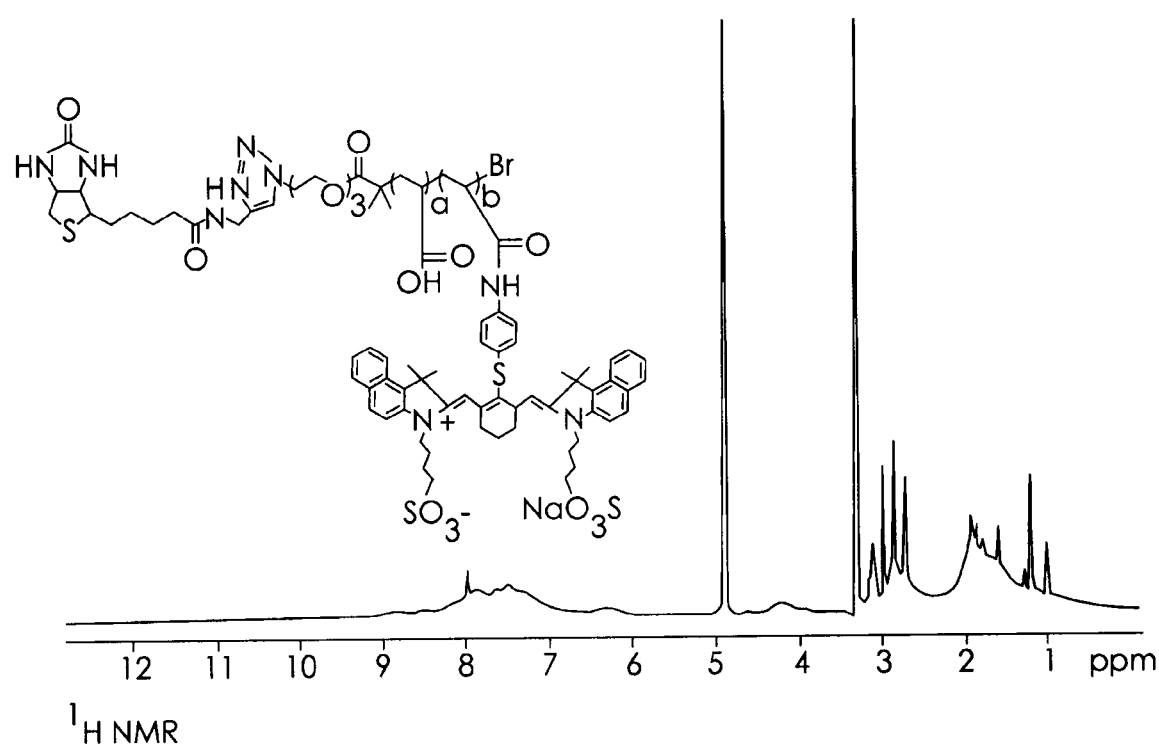

See FIG. 36 for $^1$H NMR.

9. Synthesis of Azide Terminated Poly(Acrylic acid)

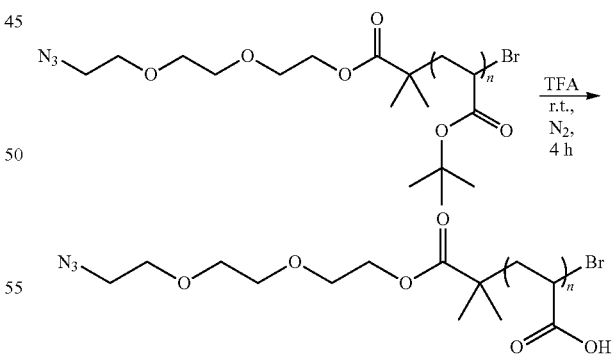

Trifluoro acetic acid (2 ml, 27 mmol) of was added dropwise to a round bottom flask containing azide terminated poly(tert-Butyl Acrylate) (0.3 g, 0.02 mmol). The reaction was stirred under N$_2$ for 4 hours. The reaction mixture was dialyzed using 3500 MWCO membrane in distilled water with several exchanges and finally the lyophilization yielded the polymer as white powder. Yield: 97% $^1$H NMR (600 MHz, D$_2$O), δ (ppm): 1.14-1.18 (m, 8H), 1.40 (s, 4H), 1.61 (s, 46H), 1.73 (s, 112H), 1.90 (s, 40H), 2.36 (s, 104H), 3.67-4.17 (m, 12H). FT-IR (cm$^{-1}$): 3022, 2117 (N$_3$), 1681, 1454.

Figure 37:
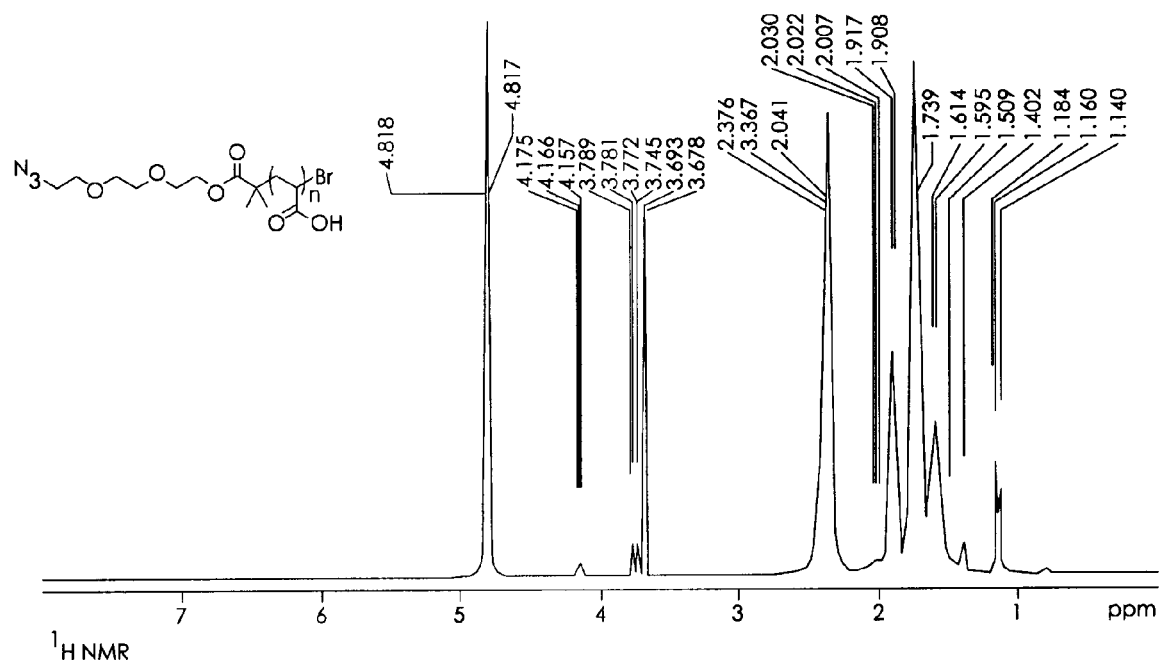
Figure 38:
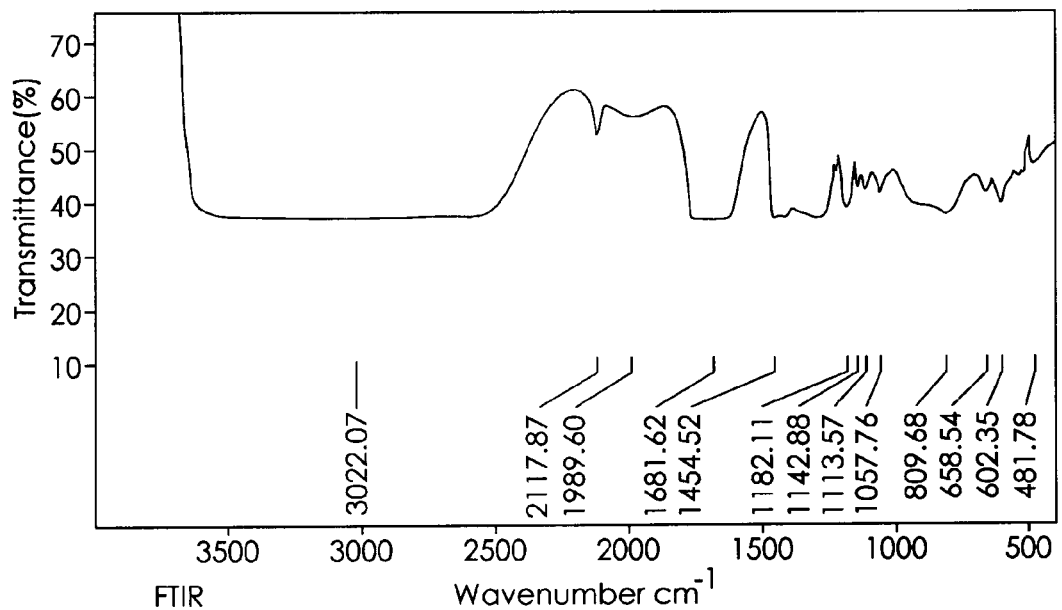

See FIGS. 37 and 38 for NMR and FTIR.

Figure 39:
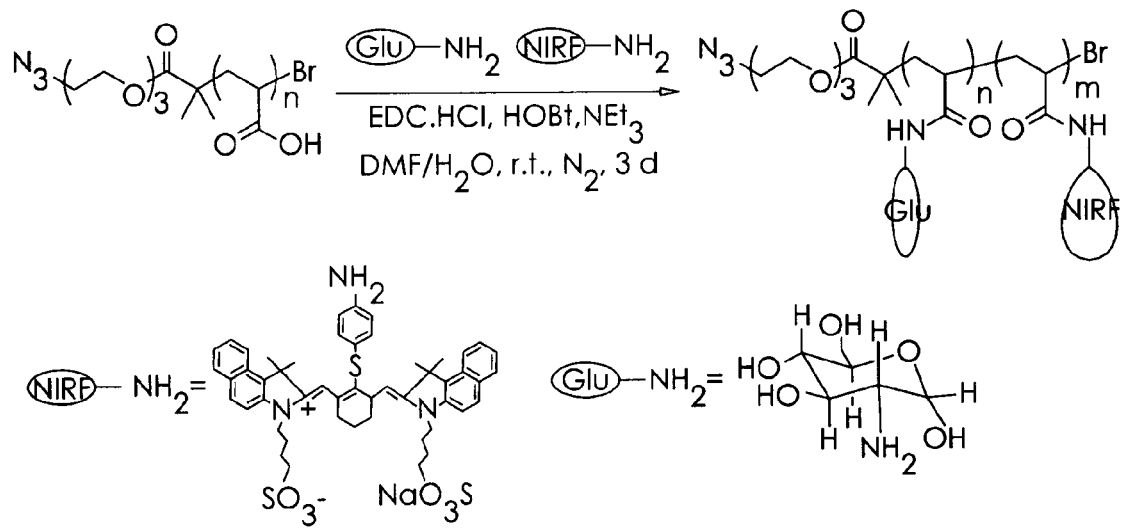
FIG. 39 shows a reaction scheme for Example 10.

10. Synthesis of Azide Terminated poly(glucosamine)-poly(NIRF dye) copolymer See FIG. 39 for synthetic scheme.

Azide terminated poly(acrylic acid) (72 mg, 0.003 mmol), NIRF dye (ADS832WS) (100 mg, 0.106 mmol), D(+)-Glucosamine (190 mg, 0.9 mmol), EDC.HCl (575 mg, 3.0 mmol) and HOBt (460 mg, 3.0 mmol) were dissolved in 10 ml of DMF in a round bottom flask and was degassed with N$_2$ and followed by dropwise addition of Et$_3$N (0.42 ml, 5 mmol). The reaction mixture was stirred at room temperature for 72 hours. The reaction mixture was dialyzed extensively using 10K MWCO membrane and then purified by passing through a Sephadex LH20 column. Finally the product was isolated as black-colored fluffy powder after lyophilization. Yield: 76%. $^1$H NMR (600 MHz, D$_2$O), δ (ppm): 1.03 (bs), 1.52-1.66 (bd), 1.76 (s), 2.01 (bs), 2.57 (s), 2.80 (s), 2.93 (bs), 3.59 (s), 3.65 (s), 3.75 (s), 5.09-5.22 (bm). FT-IR (cm$^{-1}$): 3431, 2935, 2111 (N$_3$), 1714, 1538, 1504, 1443, 1393, 1353, 1266, 1233, 1166, 1140, 1115. GPC (H$_2$O): Mn=19469, Mw=25074, PDI=1.28.

Comparing the Mn=8586 of poly(tert-butyl acrylate) and Mn=19469 of copolymer, the percent of dyes per polymer chain were calculated: employing the following equation the number of dye repeat unit per polymer chain was calculated: ax+b(64−x)=(Mn−c). Where r=number of dyes per polymer chain, a, b & c are mol. wts. of dye repeat unit, sugar repeat unit and chain-ends respectively, and the percentage of dyes per polymer chain was calculated to be ~8%.

Figure 40:
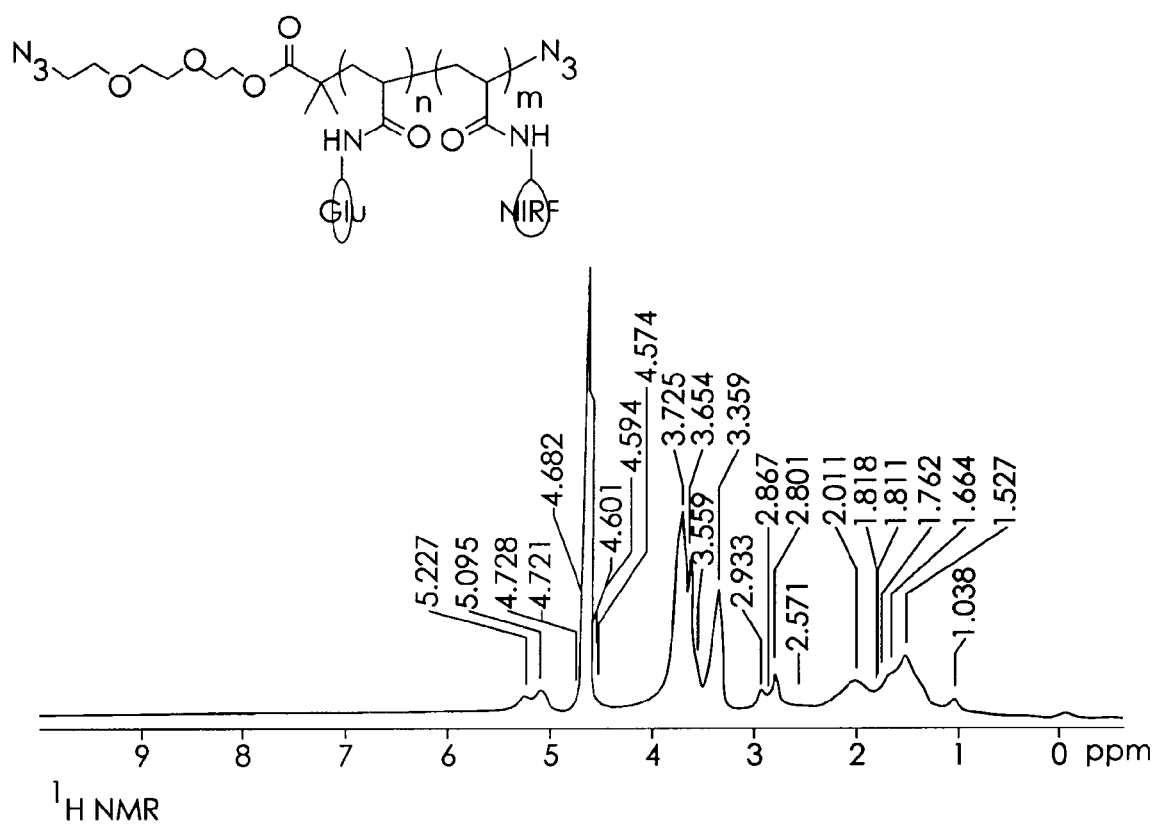
Figure 41:
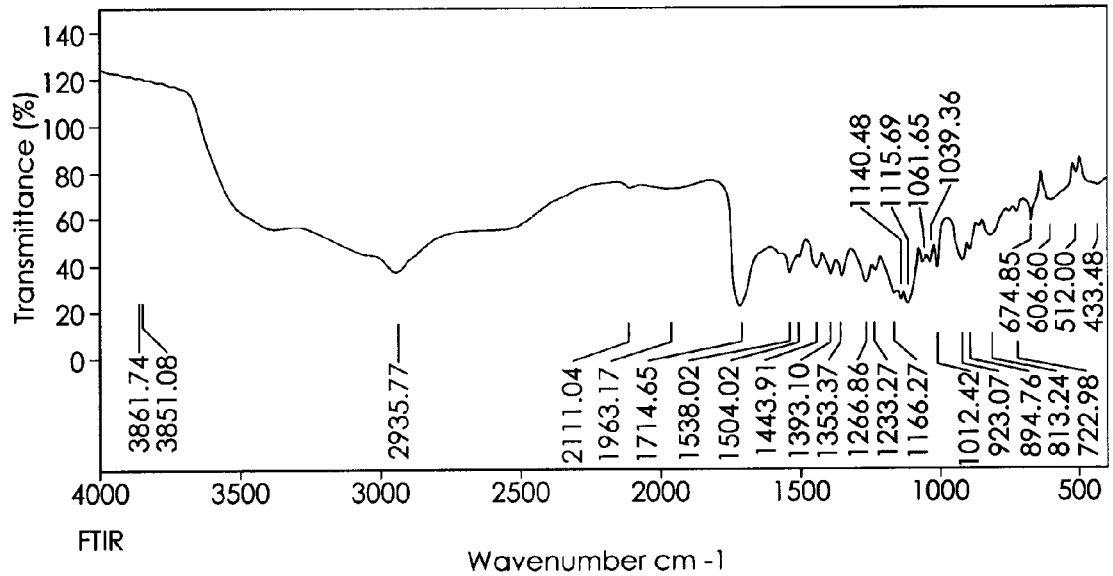

See FIG. 40 for $^1$H NMR. See FIG. 41 for FTIR.

Figure 42:
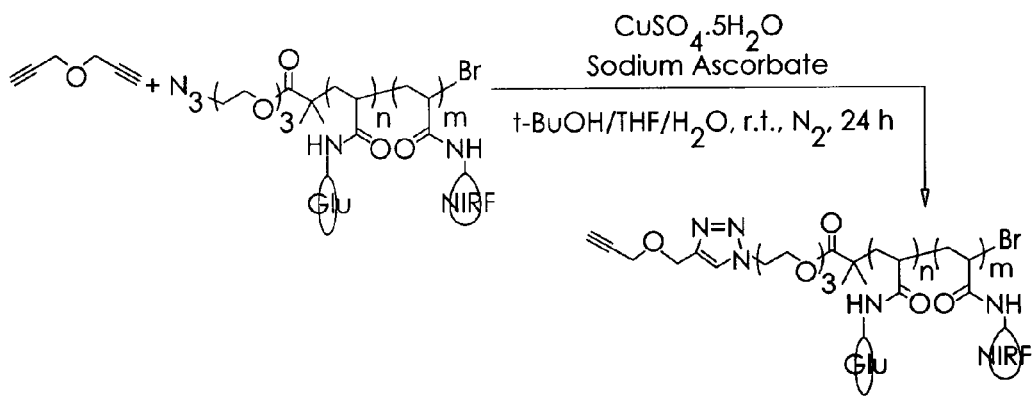
FIG. 42 shows a reaction scheme for Example 11.

11. Synthesis of Alkyne terminated poly(glucosamine)-poly(NIRF dye) copolymer See FIG. 42 for reaction scheme.

Poly(glucosamine)-poly(NIRF dye) copolymer (60 mg, 3 μmol) was dissolved in 3 ml of t-BuOH/THF/H$_2$O (1:1:1) and stirred with Propargyl ether (9.14 mg, 10 μL, 31.5 eq), CuSO$_4$.5H$_2$O (5 mg, 0.02 mmol), Sodium ascorbate (4 mg, 0.02 mmol) in a r.b. flask under N$_2$ atmosphere at room temperature for 24 h. The reaction was stopped and the reaction mixture was dialyzed extensively in deionized water using 10 kD MWCO membrane. The dialyzed mixture was further purified via Sephadex-LH 20 size exclusion chromatography and lyophilized. Yield: 42 mg (70%) $^1$H NMR (600 MHz, D$_2$O), δ (ppm): 1.03 (bs), 1.52-1.75 (bd), 2.01 (bs), 2.58 (s), 2.81 (s), 2.94 (s), 3.36 (s), 3.66-3.73 (bd), 5.06-5.23 (bm), 7.15-8.33 (m). GPC (H$_2$O): Mn=19988, Mw=28168, PDI=1.40. FT-IR (cm$^-$): 3299, 2928, (No N$_3$ peak ~2100), 1648, 1536, 1429, 1389, 1351, 1232, 1155, 1113. The absence of the azide peak (~2100 cm$^{-1}$) in the FT-IR spectra confirmed that all of the azide-end groups were reacted with dipropargyl ether. The polymer was used for further conjugation as it was.

Figure 43:
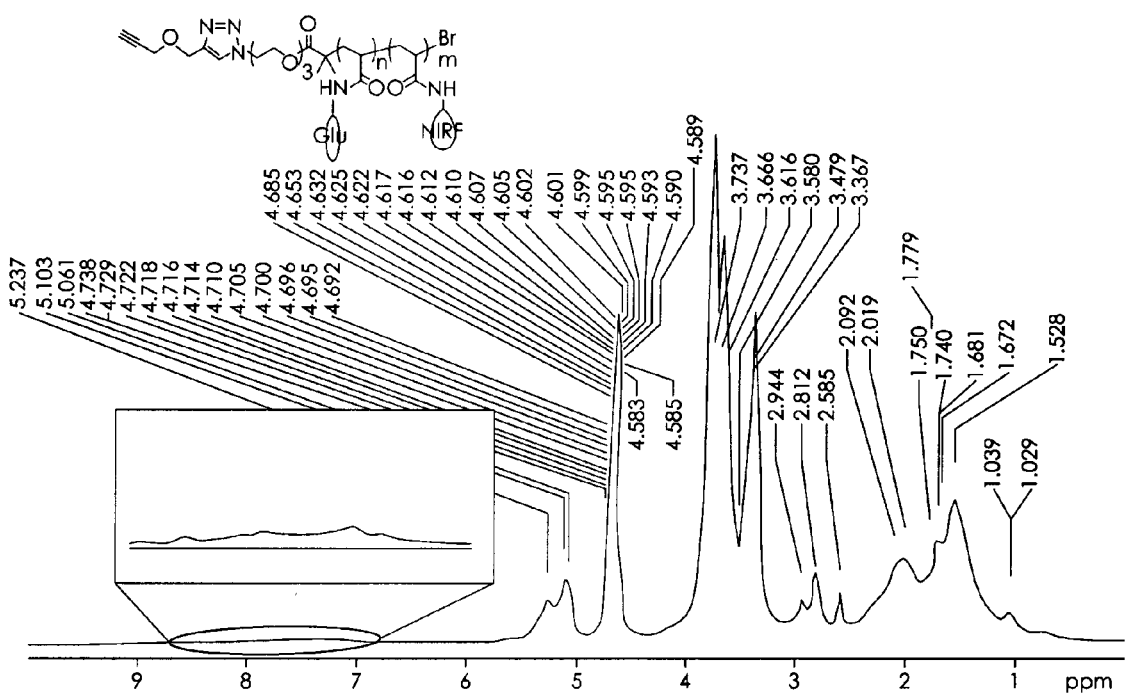
Figure 44:
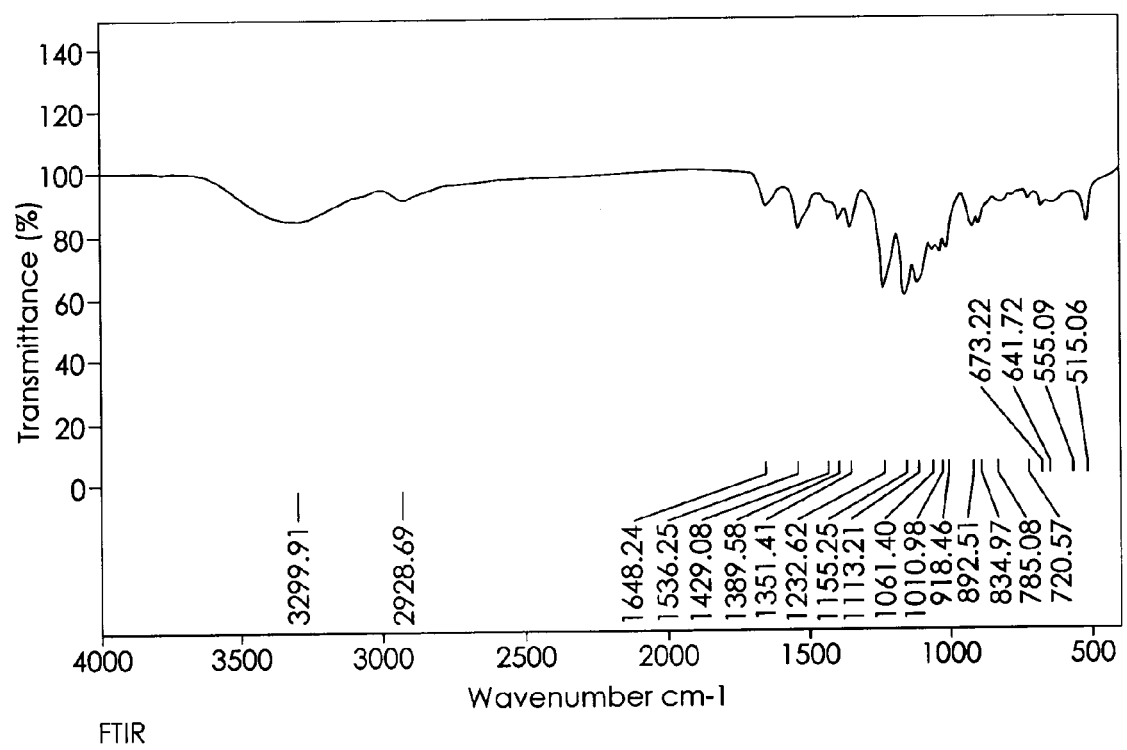

See FIG. 43 for $^1$H NMR. See FIG. 44 for FTIR.

12. Synthesis of Methyl-5-azido valerate

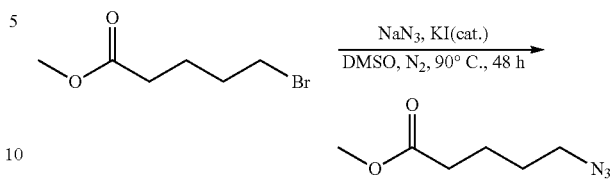

Methyl-5-bromovalerate (2.18 ml, 15.38 mmol) and Sodium azide (10 g, 10 eq) were dissolved in 20 ml DMSO in a round bottom flask and a pinch of KI was added. The mixture was stirred at 90° C. under N$_2$ atmosphere for 48 h. The reaction was cooled, diluted with water and extracted with hexanes. Organic layers were combined and dried over anhydrous Na$_2$SO$_4$. Solvent was evaporated to yield oily liquid. Yield: 2.2 g (91%); $^1$H NMR (600 MHz, CDCl$_3$, 25° C.): δ=1.56-1.59 (m, 2H; CH$_2$), 1.65-1.67 (m, 2H; CH$_2$), 2.30 (t, J=12 Hz, 2H; CH$_2$), 3.24 (t, J=12 Hz, 2H; CH$_2$), 3.62 (s, 3H; CH$_3$); $^{13}$C NMR (150 MHz, CDCl$_3$, 25° C.): δ=18.0, 24.2, 29.3, 47.0, 47.5, 169.5.

Figure 45:
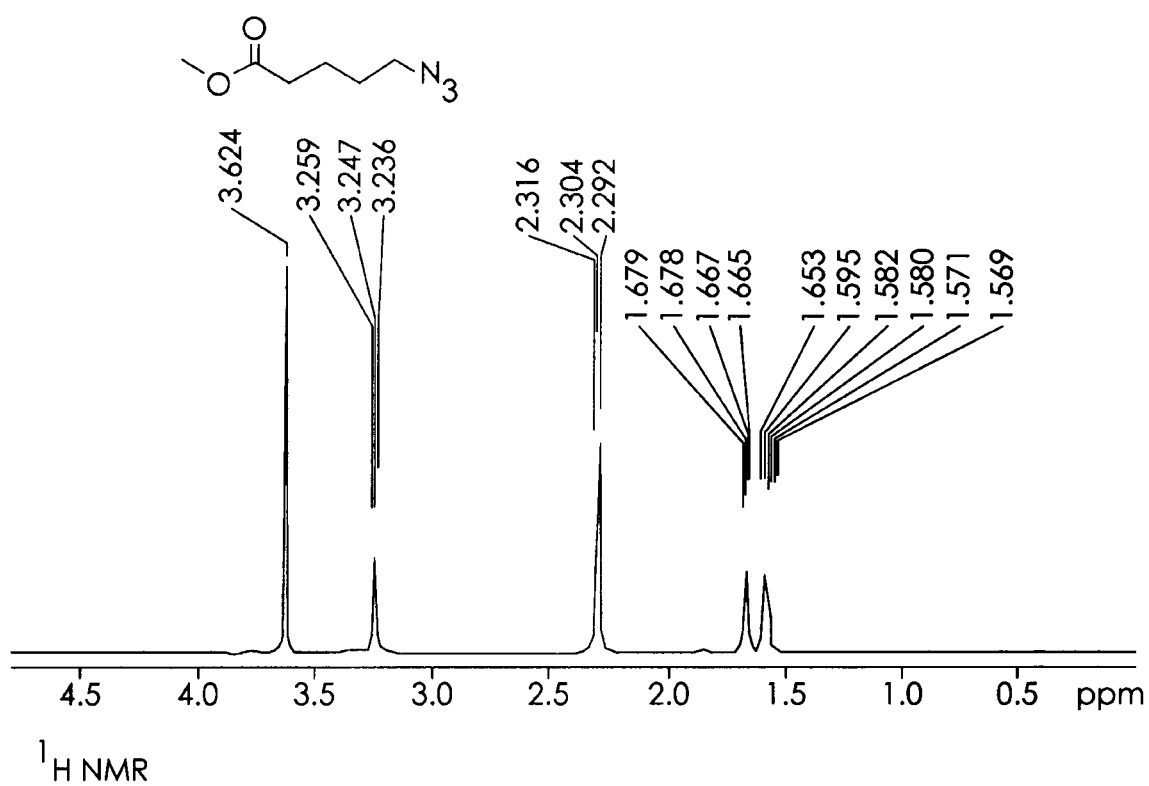
Figure 46:
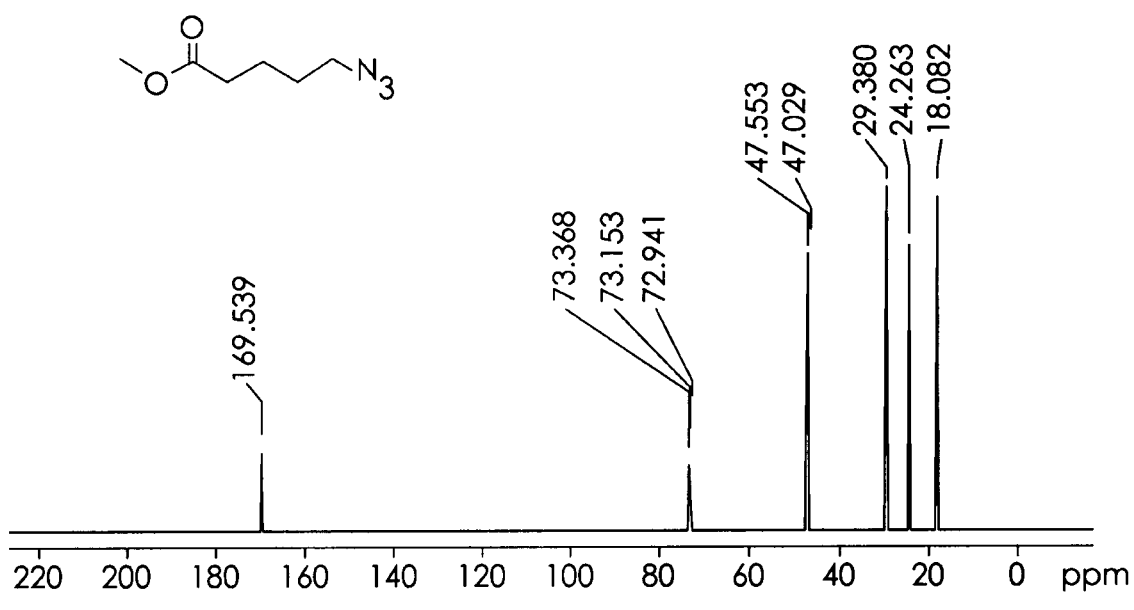

See FIG. 45 for $^1$H NMR and FIG. 46 for $^{13}$C NMR.

13. Synthesis of 5-Azido valeric acid

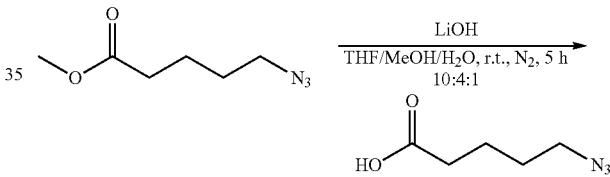

Methyl-5-azido valerate (2 g, 12.73 mmol) was dissolved in 150 ml THF/MeOH/H$_2$O (10:4:1) mixture and LiOH (3.05 g, 10 eq) was added. The mixture was stirred at mom temperature for 5 h. The reaction was stopped and acidified to pH=2 with H$_2$SO$_4$ and extracted with ethyl acetate. Organic layers were combined, dried over anhydrous Na2SO4, and finally the solvent was evaporated to yield oily product. Yield: 1.1 g (60%); $^1$H NMR (600 MHz, CDCl$_3$, 25° C.): δ=1.25 (t, J=12 Hz, 1H), 1.64-1.67 (m, 2H; CH$_2$), 1.70-1.73 (m, 2H; CH$_2$), 2.40 (t, J=11 Hz, 2H; CH$_2$), 3.30 (t, J=11 Hz, 2H; CH$_2$); $^{13}$C NMR (150 MHz, CDCl$_3$, 25° C.): S=15.5, 23.2, 29.5, 34.9, 52.4, 180.8.

Figure 47:
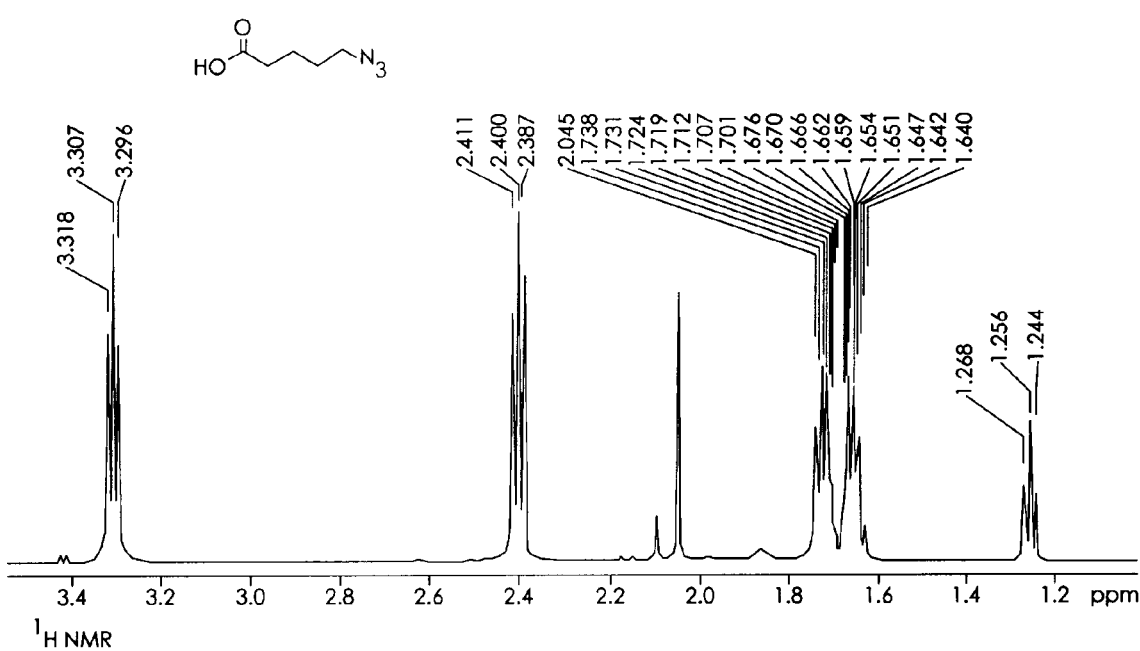
Figure 48:
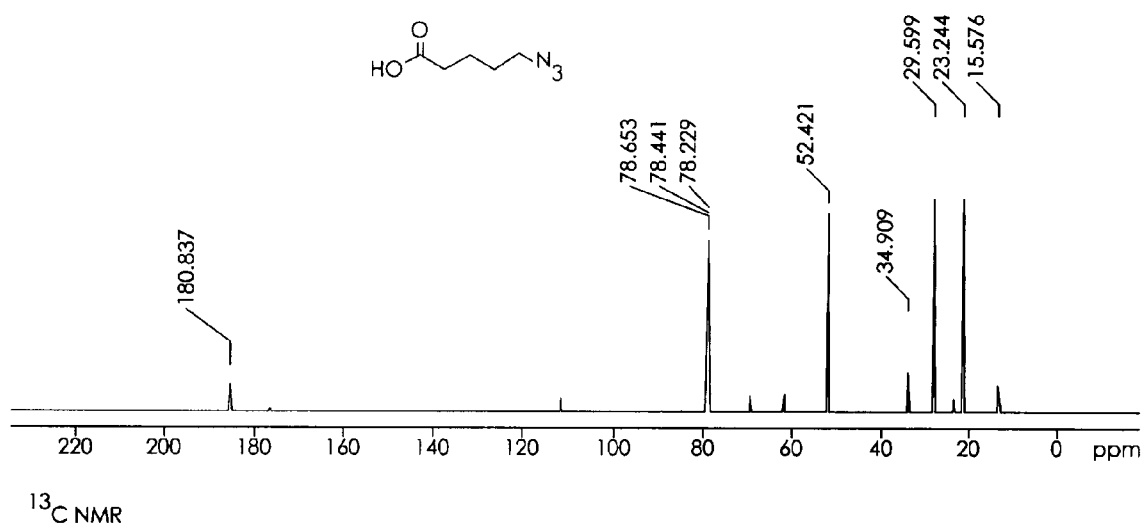

See FIG. 47 for $^1$H NMR and FIG. 48 for $^{13}$C NMR.

14. Synthesis of NHS-Azide

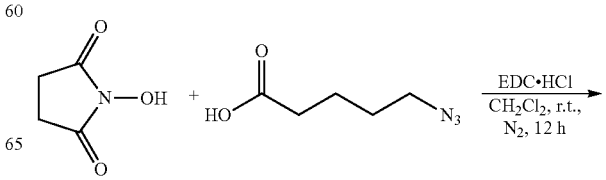

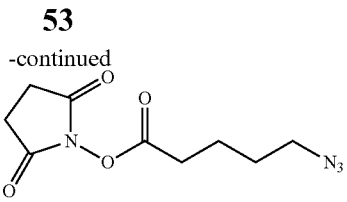

Figure 49:
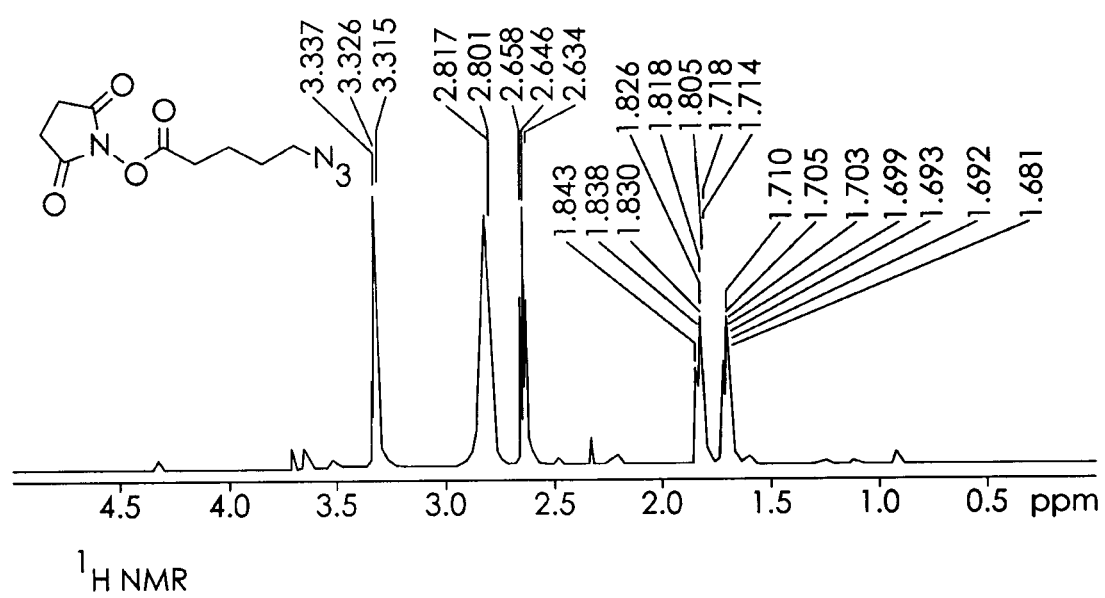

5-Azidovaleric acid (0.8 g, 5.6 mmol) and EDC.HCl (1.61 g, 1.5 mmol) were dissolved in 10 ml dry DCM and N-Hydroxysuccinimide (0.65 g, 1.01 mmol) was added. The reaction was stirred at room temperature under $N_2$ atmosphere for 12 h. The reaction was stopped, diluted with water and extracted with EtOAc. The organic layers were combined and washed with brine and dried over anhydrous Na2SO4. Finally the solvent was evaporated to yield white sticky product. Yield: 1.2 g (90%); $^1$H NMR (600 MHz, CDCl$_3$, 25° C.): δ=1.68-1.71 (m, 2H; CH$_2$), 1.80-1.84 (m, 2H; CH$_2$), 2.64 (t, J=12 Hz, 2H; CH$_2$), 2.81 (s, 4H; CH$_2$), 3.32 (t, J=11 Hz, 2H; CH$_2$); $^{13}$C NMR (150 MHz, CDCl$_3$, 25° C.): δ=17.8, 21.6, 23.9, 26.4, 46.8, 164.2, 165.1;

See FIG. 49 for $^1$H NMR and FIG. 50 for $^{13}$C NMR.

15. Synthesis of Azide Modified BSA

See FIG. 51, top, for reaction scheme.

BSA (5 mg, 5 mg/ml in PBS, pH 7.4) was incubated with NHS-Azide (5 mg in 100 μl DMSO, 10 eq to each modifiable lysine group) at room temperature for 3 h and then dialyzed against 0.1 M Tris buffer, pH 8.0 for 48 h to remove excess of azide linker. The dialyzed product was characterized via FPLC and used for further bioconjugation.

16. Conjugation of Biotin Terminated copolymer and Avidin

See FIG. 51, bottom, for reaction scheme.

Avidin (1 mg) was dissolved in 0.25 mL of PBS buffer, pH 7.4. Poly(glucosamine)-poly(NIRF dye) copolymer (5.5 mg) was dissolved in 0.65 ml PBS buffer, and slowly added. After 1.5 h at room temperature, the solution was extensively dialyzed using a 50 KDa MWCO membrane in deionized water, and the modified protein was analyzed by fast protein liquid chromatography (FPLC) and SDS-PAGE.

SDS PAGE

Sodium dodecylsulfate-polyacrylamide gel electrophoresis (SDS-PAGE) was performed by forming a complex of avidin with the polymer, and then avidin alone as a control. First a mixture of avidin with the polymer in the ratio of 1:20 was incubated in PBS overnight on a rocking platform at 4° C., then the samples were heated and loaded onto 10-20% PAGEgel SDS Cassette Gel 17-Well. The avidin, and the avidin binding complex were visualized using Odyssey imaging system (LI-COR, Lincoln, Nebr.) in the NIR at 800 nm, then detected after protein staining with coomassie.

Figure 52:
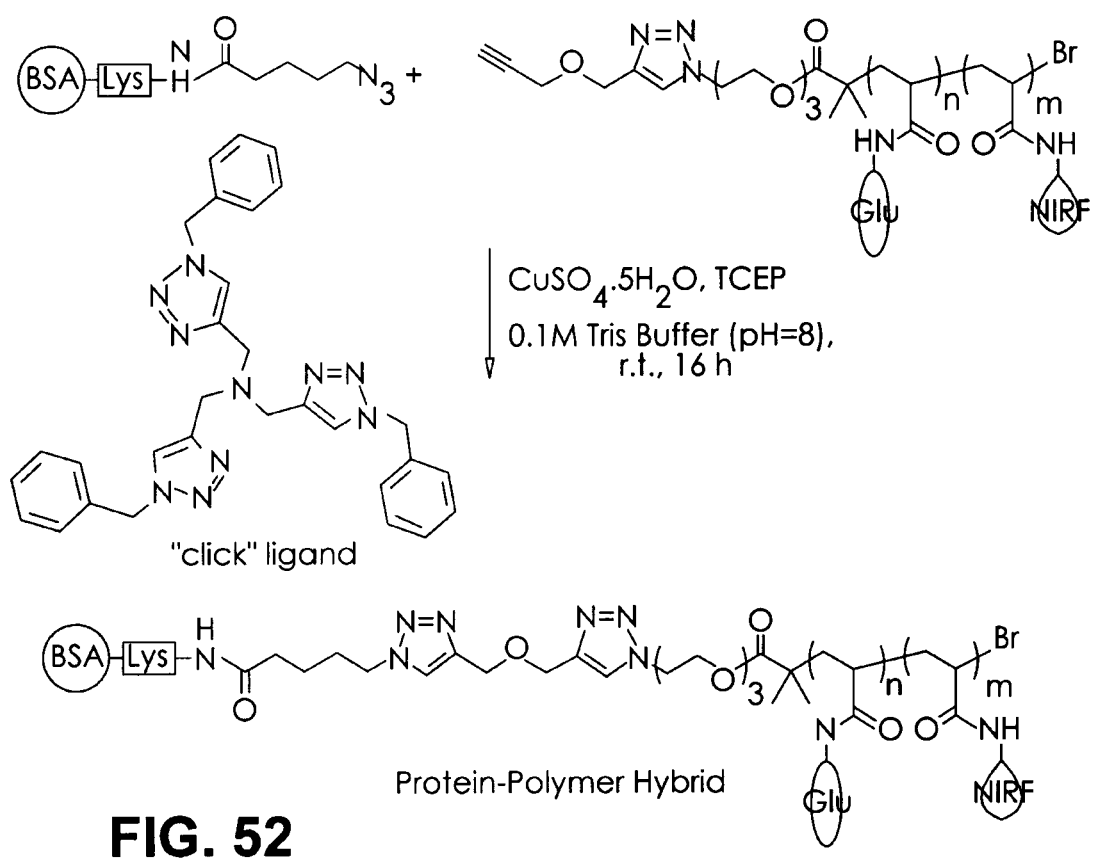
FIG. 52 shows a reaction scheme for Example 17.

17. Synthesis of Protein-Polymer Conjugate; BSA-"clicked"-poly(glucosamine)-poly(NIRF dye) copolymer See FIG. 52 for reaction scheme.

BSA-azide (5 mg, approx. 1.5 μmol in azide) was incubated with alkyne-poly(glucosamine)-poly(NIRF dye) copolymer (20 mg, 1 mop in Tris buffer (1800 μL, 0.1 M, pH 8) in the presence of TCEP (4 mM), "click" ligand (4 mM, dissolved in 200 μL if DMF) and copper sulfate (2 mM) for 16 h at 4° C. The ligand was added before the addition of copper sulfate. The reaction mixture was then dialyzed using Spectra Por 6 dialysis membrane (MWCO 50K) in PBS pH 7.4 for 48 h to remove excess of Copper and ligand. The conjugate was further characterized via Fast Protein Liquid Chromatographic system (Akta Purifier, Amarsham Biosciences) using HiPrep 26/10 Sephacryl S-200HR (GE Healthcare) size-exclusion column in PBS pH 7.4 as eluent buffer. The conjugate was also characterized via SDS PAGE.

SDS PAGE

Sodium dodecylsulfate-polyacrylamide gel electrophoresis (SDS-PAGE) was performed with BSA-polymer conjugate and alkyne-terminated poly(glucosamine)-poly(NIRF dye) copolymer, azide modified BSA as controls using a 10-20% PAGEgel SDS Cassette Gel. To confirm that the copolymer was indeed chemically bonded to the protein, the mixture of copolymer and modified BSA was incubated at 4° C. for 16 h in the same ratio but without the "click" reagents and dialyzed the mixture with a 50 KD MWCO membrane. The gel cassette was visualized using Odyssey imaging system (LI-COR, Lincoln, Nebr.) in the NIR at 800 nm, then detected after protein staining with coomassie.

18. Synthesis of Bromide-Terminated Methyl propanoate Poly(tert-butyl acrylate)

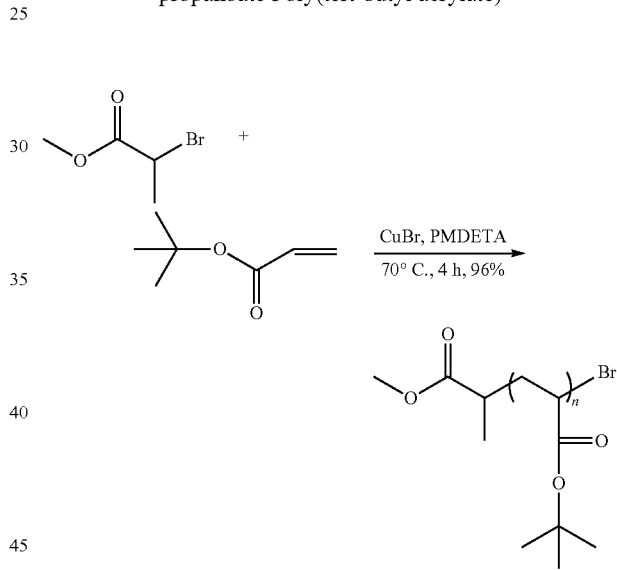

A 250 mL flask was charged with CuBr (0.448 g, 3.12 mmol), and a septum was placed over the stem of the stopcock. Under positive pressure of Ar$_e$, tert-butyl acrylate (10 mL, 68.18 mmol), methyl 2-bromopropanoate (0.12 mL, 1.09 mmol), and pentamethyldiethylenetriamine (PMDETA) (0.63 mL, 3.05 mmol) were added via syringe, followed by addition of 1 ml degassed toluene. Following three freeze-pump-thaw degassing cycles, the reaction was allowed to stir for 4 h at 70° C. After quenching of the polymerization by submerging the flask in liquid nitrogen, the mixture was allowed to warm to ambient temperature. The reaction mixture was diluted with tetrahydrofuran and Cuprisorb was added, after stirred ca. 15 minutes, filter and removed solvent under vacuum. Dissolved the sticky mixture in small amount THF and precipitated two times from 10% methanol, deionized water solution. Isolated yield was 8.35 g (93%). Mn=5889 g/mole, M$_w$/M°=1.1. $^1$H NMR (CD$_3$OD, 300 MHz) δ (ppm): 3.66 (s, CH$_3$—CH—COOCH$_3$), 2.27 (b, —CH—CH$_2$—CH—Br), 1.84-1.96 (bm, —CH—CH$_2$—CH—Br), 1.45 (s, —CH—COOC—(CH$_3$)$_3$), 1.17 (s, CH$_3$—

CH—COOCH$_3$); IR (cm$^{-1}$): 3434, 2977, 2933, 2258, 1991, 1728, 1479, 1449, 1392, 1367, 1259, 1155, 1035, 917, 845, 734.

See FIG. 53 for $^1$H NMR and FTIR.

19. Synthesis of Azido-Terminated Methyl propanoate Poly(tert-butyl acrylate)

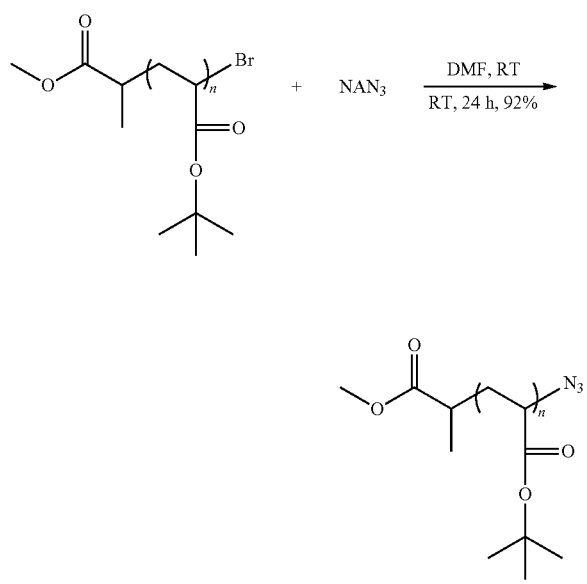

Bromide-terminated methyl propanoate Poly(tert-butyl acrylate) (1.51 g, 0.26 mmol) was dissolved in DMF (12 mL), and NaN$_3$ (0.1 g, 1.55 mmol) was added to the solution, which was stirred at room temperature for 24 hours. Put the mixture solution into plenty of 15% methanol, deionized water solution. The product was precipitated, washed with water, white solid was obtained. Dissolved in CH$_2$Cl$_2$, dried with Na$_2$SO$_4$, filtered, dried under vacuum, and mg polymer was obtained. Mn=5775 g/mole, M$_w$/M$_n$=1.20. $^1$H NMR (CD$_3$OD, 300 MHz) δ (ppm): 3.66 (s, CH$_3$—CH—COOCH$_3$), 2.25 (b, —CH—CH$_2$—CH—N$_3$), 1.72-1.84 (bm, —CH—CH$_2$—CH—N$_3$), 1.45 (s, —CH—COOC—(CH$_3$)$_3$), 1.17 (s, CH$_3$—CH—COOCH$_3$); IR (cm$^{-1}$): 3434, 2978, 2933, 2258, 2113, 1991, 1730, 1479, 1392, 1367, 1257, 1155, 1035, 917, 846, 734.

Figure 54:
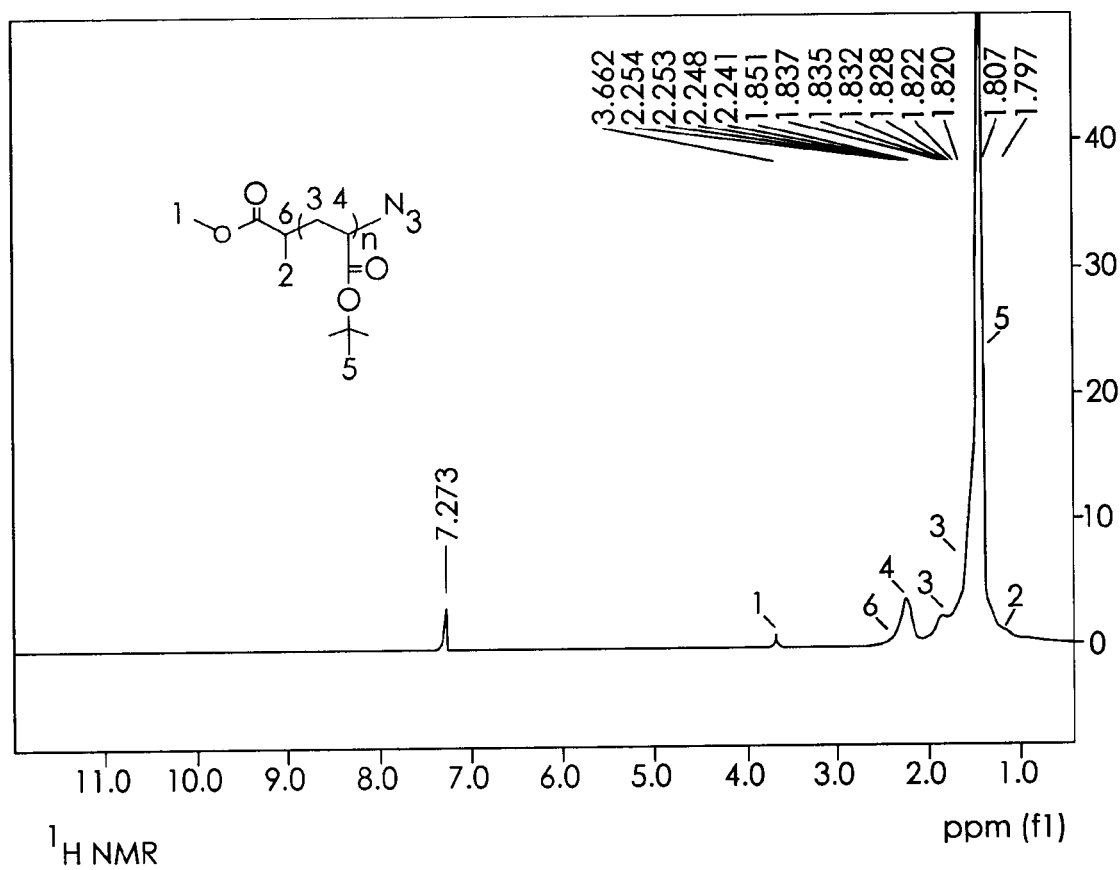
Figure 55:
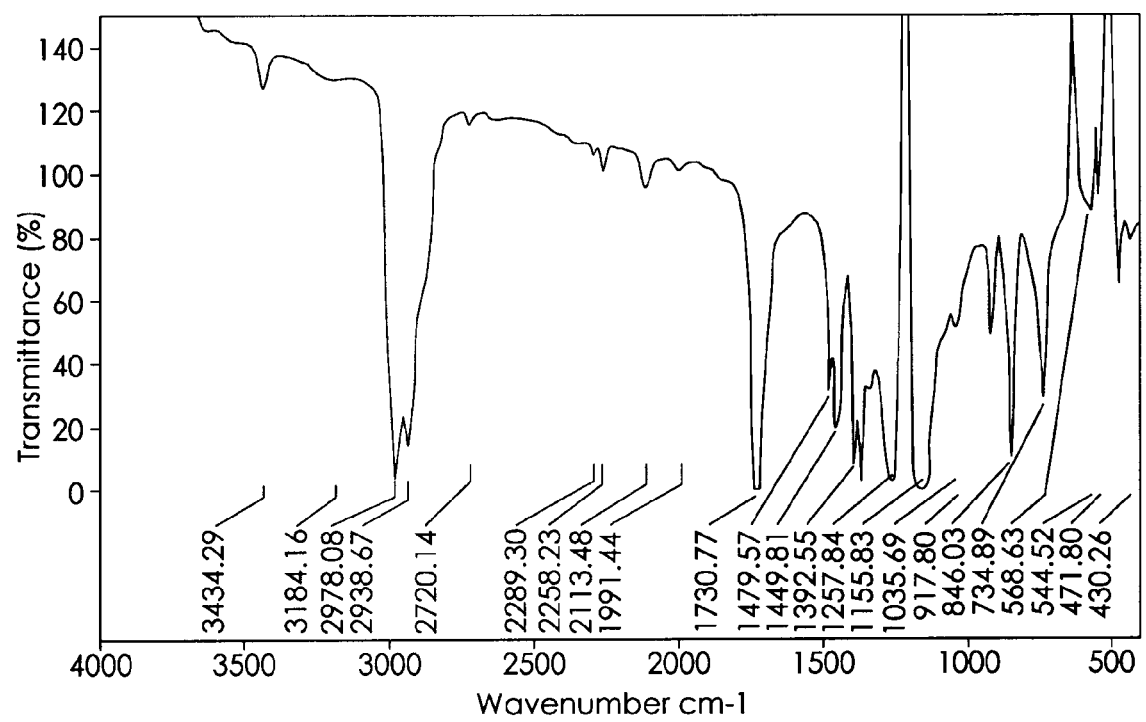

See FIG. 54 for $^1$H NMR and FIG. 55 for FTIR.

20. Synthesis of Azido-Terminated Methyl propanoate Poly(acrylic acid)

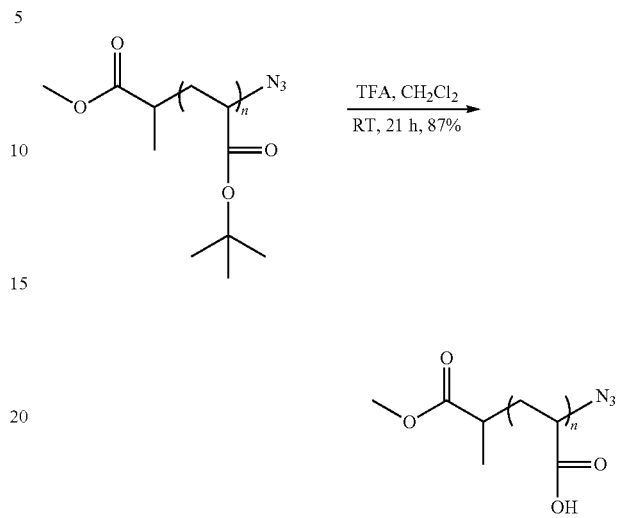

Azide-terminated methyl propanoate Poly(tert-butyl acrylate) was dissolved in a solution of trifluoroacetic acid (3.5 mL, 46 mmol) in dichloromethane (12 mL). The reaction was allowed to stir at ambient temperature for overnight. The solvent was removed under vacuum, and the resulting solid was dissolved in water. The solution was transferred to a dialyzed bag (MWCO 3.5 kDa), and the solution was dialyzed against a continuous flow of deionized water for 24 h. The final water soluble polymer was isolated by lyophilization: Isolated yield 0.575 g, (87%). $^1$H NMR (DMSO, 300 MHz) δ (ppm): 12.27 (s, CH—COOH), 3.58 (s, CH$_3$—CH—COOCH$_3$), 2.22 (s, —CH—CH$_2$—CH—N$_3$), 1.76 (b, —CH—COOC—(CH$_3$)$_3$, —CH—COOH), 1.52 (bm, —CH—COOC—(CH$_3$)$_3$, —CH$_2$—CH—COOH), 1.24 (s, CH$_3$—CH$_2$—CH—COOH), 1.08 (s, CH$_3$—CH$_2$—CH—COOCH$_3$); IR (cm$^{-1}$): 3022, 2118, 1989, 1681, 1454, 1182, 1142, 1113, 1057, 921, 809.

About 4% tert-butyl acrylate group wasn't move from $^1$H NMR by comparing the integral of protons (—CH—CH$_2$—CH—N$_3$) from the repeat units at δ=2.22 ppm to COOH (δ=12.27 ppm) from the carboxylic acid component.

21. Azido-Terminated Methyl propanoate Poly(acrylic acid)-poly(ADS832WS) [low dye loading]

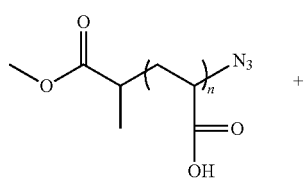 +

-continued

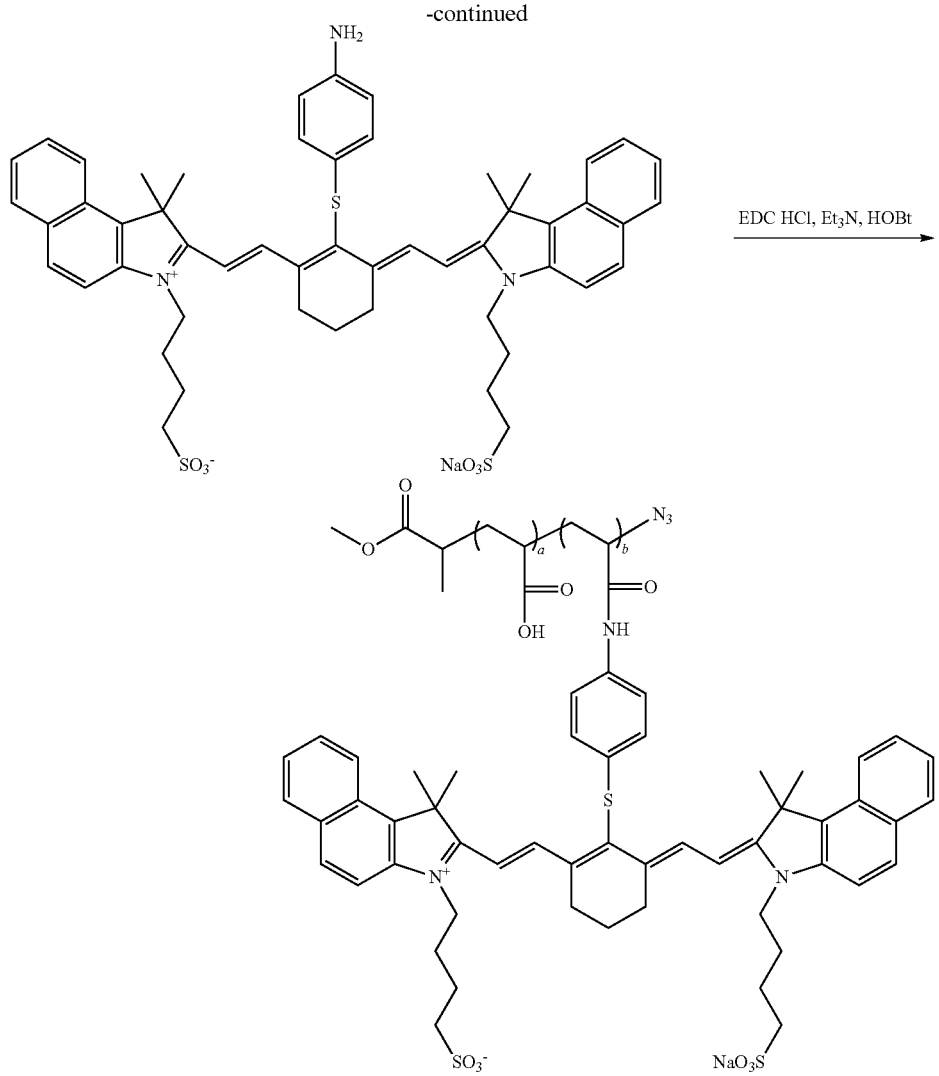

Azido-terminated methyl propanoate Poly(acrylic acid) (72 mg, 0.99 mmol), near infrared absorption dye ADS832WS (20 mg, 0.02 mmol), EDC.HCl (25 mg, 0.13 mmol), and HOBt (16.3 mg, 0.12 mmol) were dissolved in DMF (3.8 mL), Triethylamine (0.03 mL, 0.17 mmol) was added. The mixture was stirred 2.5 day at room temperature. After stopping of the reaction, the solution was transferred to a dialysis bag (MWCO 3.5 KDa), and the solution was dialyzed against a continuous flow of deionized water for 24 h. After dialysis, filtered, and lyophilized, green brown cotton shape crude product was obtained. The final water soluble polymer (4) was isolated by Sephadex™ LH-20 column and lyophilization: Isolated yield was 38 mg. $^1$H NMR (CD$_3$OD, 300 MHz) δ (ppm): 8.93 (bd), 8.18 (bd), 7.98 (bm), 7.62 (bs), 7.47 (bm), 7.12 (bm), 6.45 (bm), 4.31 (bs), 3.66 (s), 3.21 (m), 2.86 (s), 2.45 (bs), 1.93 (bs), 1.69 (bm), 1.30 (m), 1.12 (m). IR (cm$^{-1}$): 3440, 2932, 2114, 1967, 1715, 1537, 1503, 1430, 1392, 1353, 1269, 1236, 1169, 1139, 1116, 1063, 1039, 1012, 922, 894.

The quantity of different compositions in the copolymer was quantified by comparing the peak area of the protons from dye ADS832WS at 7.12-8.93 ppm to that of —CH$_2$—CH— protons from main chain of polymer at 1.69-1.93 ppm, and results showed the loading number of dye ADS832WS was 8.10%.

See FIG. 56 for $^1$H NMR and FTIR.

22. Azido-Terminated Methyl propanoate Poly(acrylic acid)-poly(ADS832WS) [medium dye loading]

Figure 57:
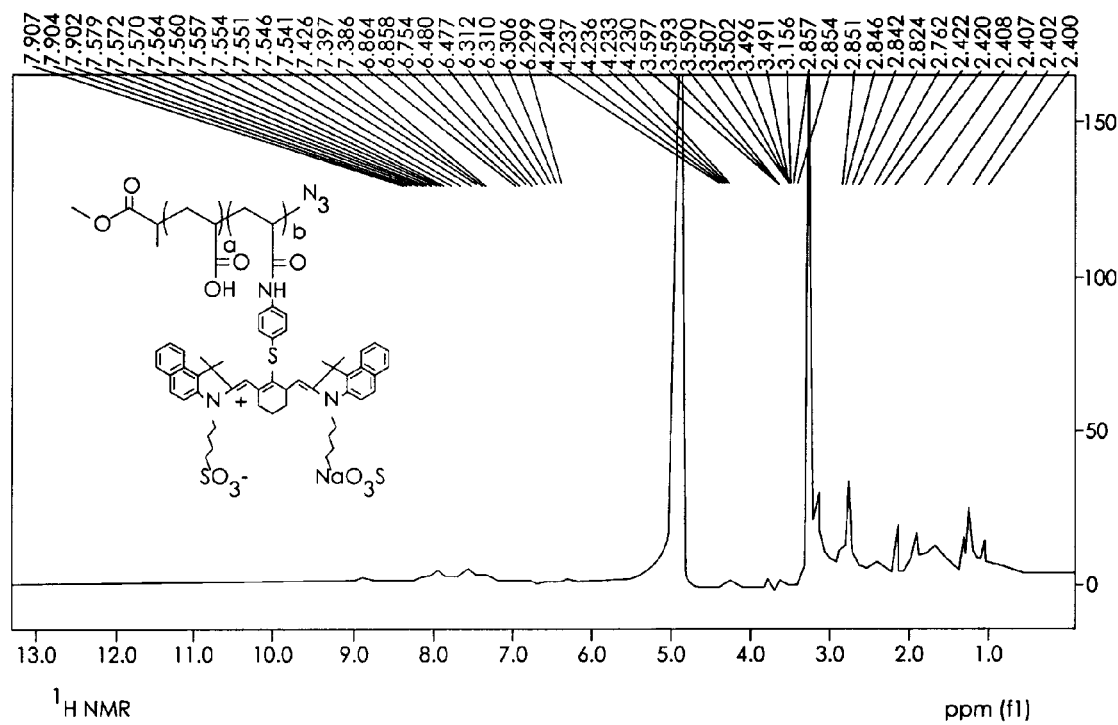
Figure 58:
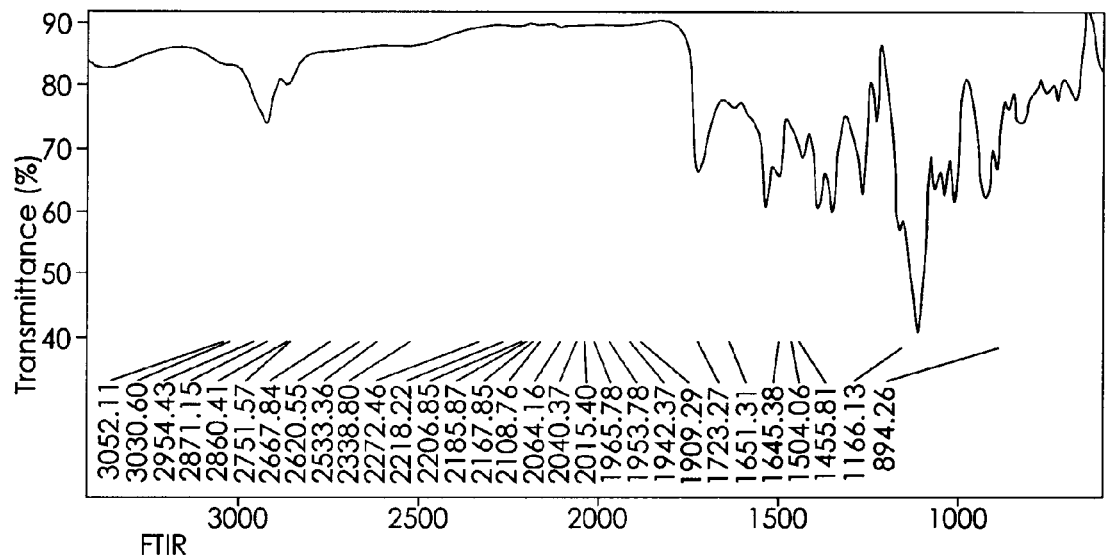

$^1$H NMR (CD$_3$OD, 300 MHz) δ (ppm): 8.91 (bd), 8.15 (bm), 7.91 (bm), 7.57 (bs), 7.42 (bm), 7.1 (bm), 6.48 (bm), 4.23 (bs), 3.59 (s), 3.49 (s), 3.15 (m), 2.85 (m), 2.42 (s), 1.93 (s), 1.69 (bm), 1.25 (m), 1.06 (m). IR (cm$^{-1}$): 3440, 2929, 2860, 2109, 1723, 1538, 1504, 1456, 1393, 1353, 1266, 1233, 1166, 1140, 1115, 1061, 1039, 1012, 923, 894.

loading number of dye ADS832WS was 13.14%.
See FIG. 57 for $^1$H NMR and FIG. 58 for FTIR.

23. Azido-Terminated Methyl propanoate Poly(acrylic acid)-poly(ADS832WS) [high dye loading]

Figure 59:
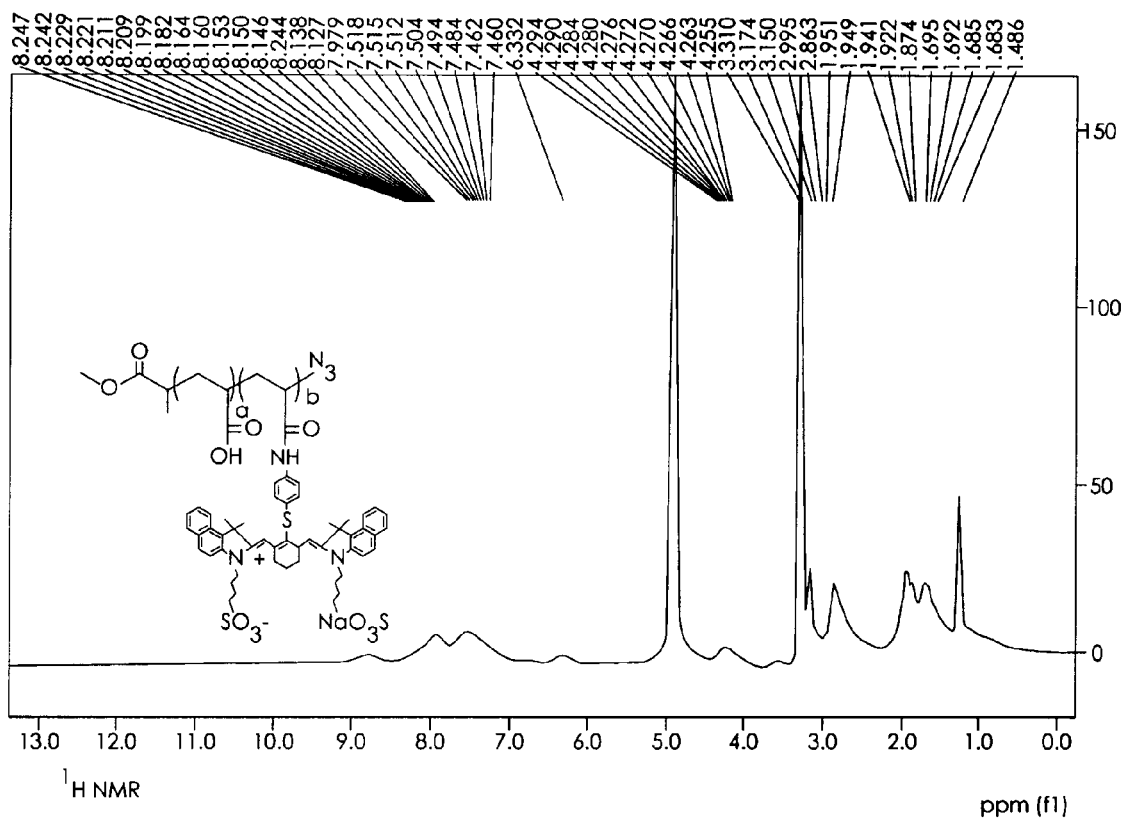
Figure 60:
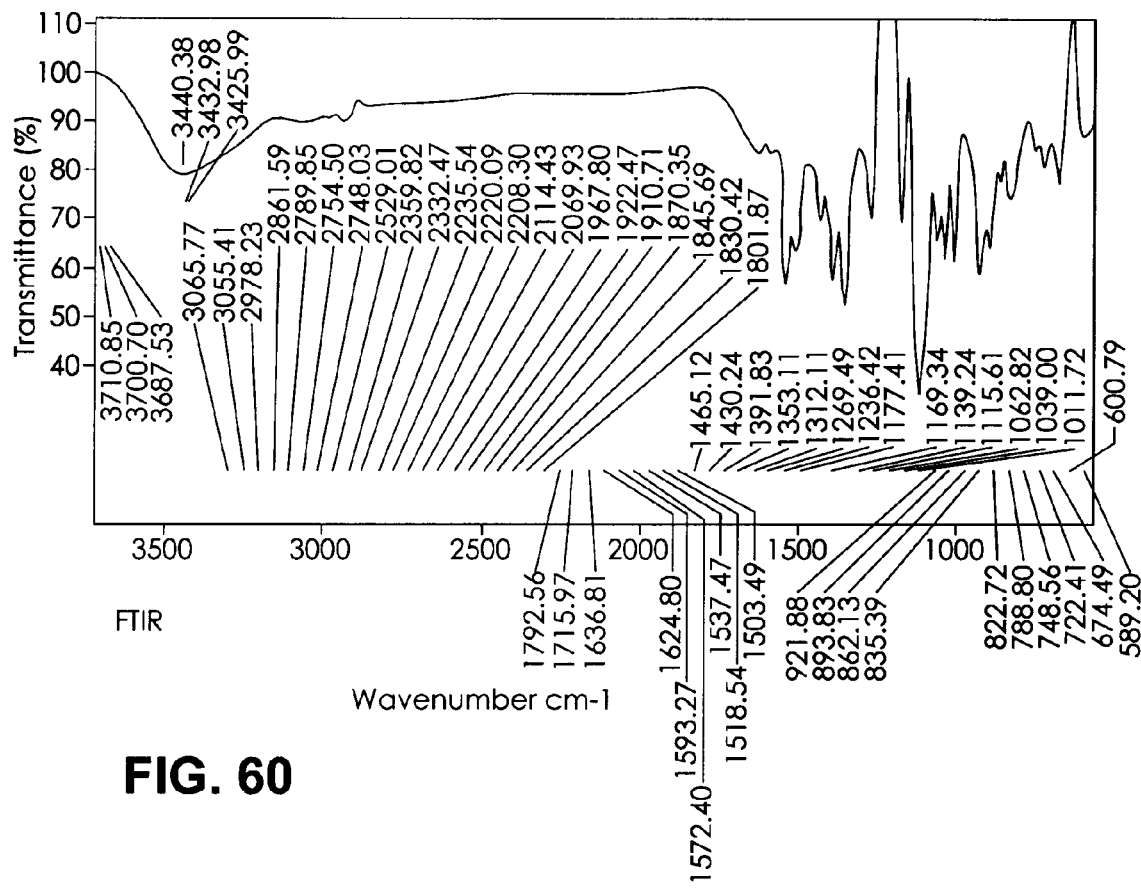

$^1$H NMR (CD$_3$OD, 300 MHz) δ (ppm): 8.91 (bs), 8.21 (bm), 7.98 (bm), 7.51 (bm), 7.42 (bm), 7.2 (bm), 6.33 (bm), 4.27 (bs), 3.5 (s), 3.17 (m), 2.86 (m), 2.45 (bs), 1.95 (bm), 1.69 (bm), 1.25 (m). IR (cm$^{-1}$): 3440, 2929, 2860, 2114, 1723, 1538, 1504, 1456, 1393, 1353, 1266, 1233, 1166, 1140, 1115, 1061, 1039, 1012, 923, 894.

loading number of dye ADS832WS was 38.85%.
See FIG. 59 for $^1$H NMR and FIG. 60 for FTIR.

24. Azido-Terminated Methyl propanoate Poly(glucoseamine)-poly(ADS832WS)
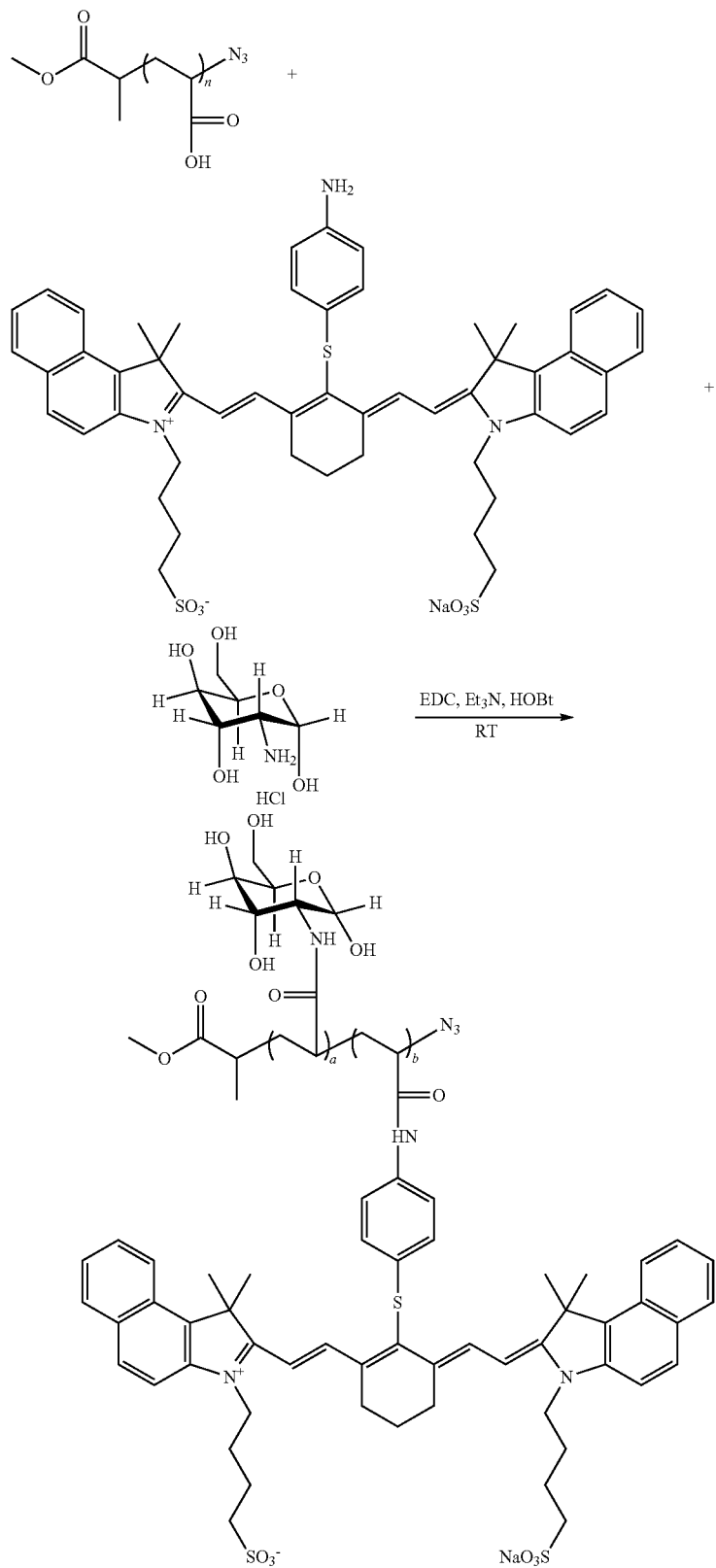

Azido-terminated methyl propanoate Poly(acrylic acid) (72 mg, 0.99 mmol), near infrared absorption dye ADS832WS (20 mg, 0.02 mmol), EDC.HCl (25 mg, 0.13 mmol), and HOBt (16.3 mg, 0.12 mmol) were dissolved in DMF (3.8 mL), Triethylamine (0.03 mL, 0.17 mmol) was added. After stirred 2 day at room temperature, glucosamine (248 mg, 1.15 mmol) in water (1.5 mL), EDC.HCl (218 mg, 1.137 mmol), and HOBt (153 mg, 1.149 mmol) mixture solution in DMF (1.5 mL) were added via syringe. The mixture was stirred another 3 day at room temperature. After stopping of the reaction, the solution was transferred to a dialysis bag (MWCO 3.5 KDa), and the solution was dialyzed against a continuous flow of deionized water for 24 h. After dialysis, filtered, and lyophilized, green brown cotton shape crude product was obtained. The final water soluble copolymer was isolated by Sephadex™ LH-20 column and lyophilization: Isolated yield 195 mg. $^1$H NMR (DMSO, 300 MHz) δ (ppm): 7.35-8.60 (bm), 6.58 (bm), 5.10 (bs), 4.60 (bm), 3.62 (bs), 3.18 (bs), 1.25-2.30 (bm), 1.04 (bs). IR (cm$^{-1}$):

The quantity of different compositions in the copolymer was quantified by comparing the peaks area of the protons from dye ADS832WS at 7.35-8.60 ppm, glucosamine at 5.10 and 4.60 ppm, and that of —CH$_2$—CH— protons from main chain of polymer at 1.25-2.30 ppm. Results showed the loading number of dye ADS832WS and glucosamine were 11.92% and 81.97% respectively.

Figure 61:
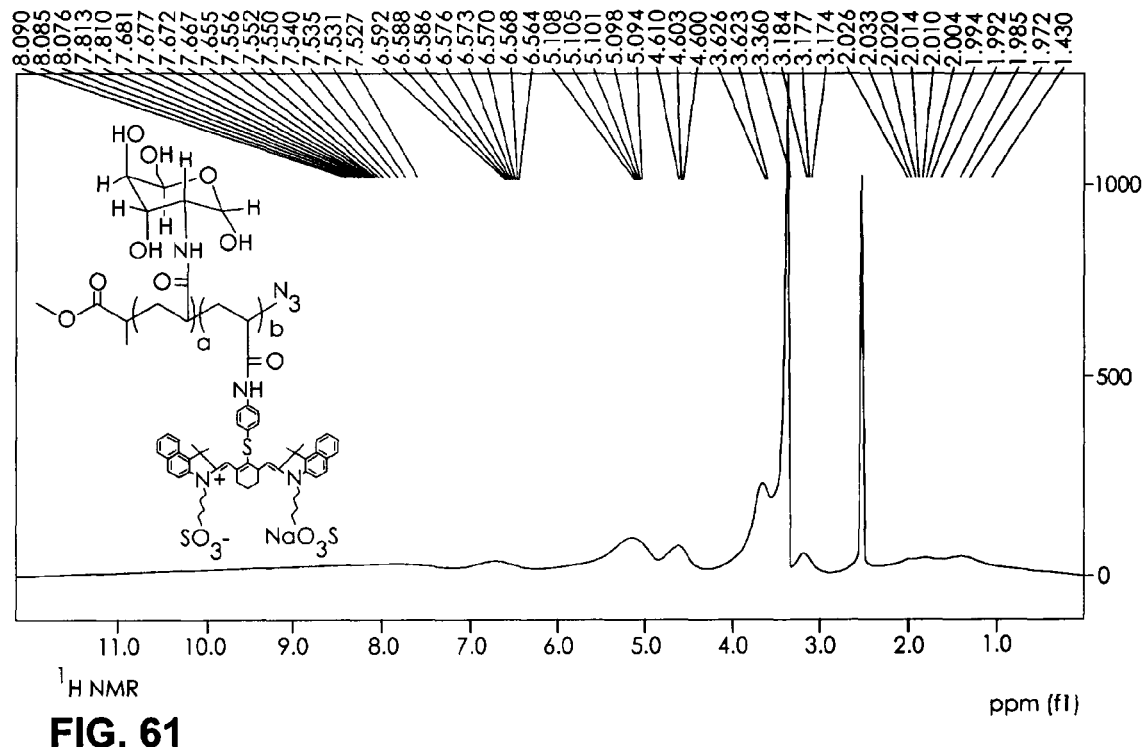

See FIG. 61 for $^1$H NMR.

25. Azido-Terminated Methyl propanoate Poly(glucoseamine)-poly(ADS832WS)

Figure 62:
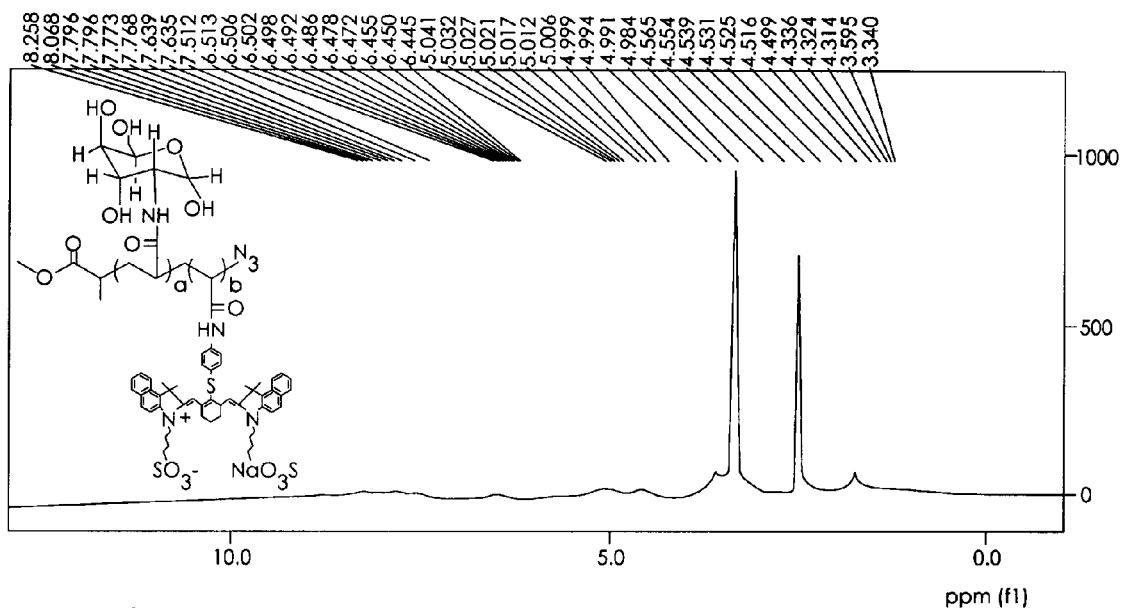

Results showed the loading number of dye ADS832WS and glucosamine were 13.66% and 32.93% respectively.
See FIG. 62 for $^1$H NMR.

26. Azido-Terminated Methyl propanoate Poly(glucoseamine)-poly(ADS832WS) (9)

Figure 63:
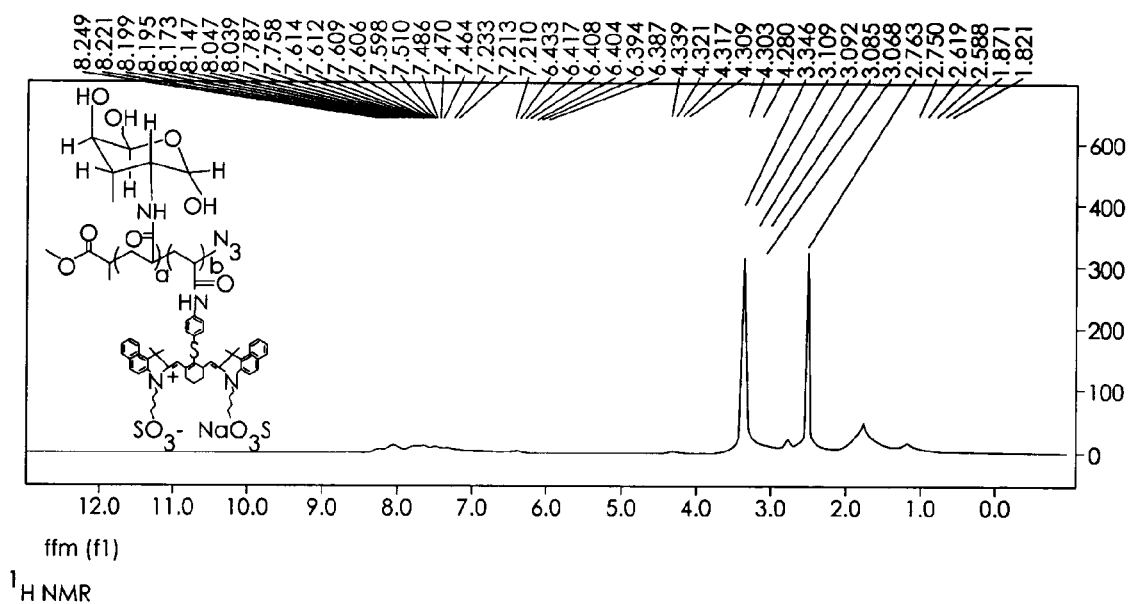

Results showed the loading number of dye ADS832WS and glucosamine were 33.65% and 5.46% respectively.
See FIG. 63 for $^1$H NMR.

Synthesis of Azide Polymers by Novel Nucleophilic Substitution Methodology

27. Synthesis of 3-bromo-1-(2-(2-(2-chloroethoxy)ethoxy)ethoxy)-3-methylbutan-2-one

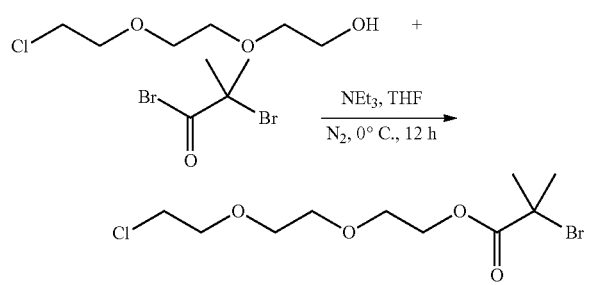

A solution of 2-bromoisobutyryl bromide (4.58 g, 19.9 mmol) and triethylamine (2.18 g, 21.5 mmol) in THF (5 mL) was cooled to 0° C. in a 2-necked round-bottomed flask. A solution of 2-[2-(2-azidoethoxy)ethoxy]ethanol (3 g, 17.8 mmol) in THF (5 mL) was added dropwise with stirring. The reaction mixture was then stirred at room temperature for 12 h, filtered, and the solvent was removed by rotatory evaporation. The crude product was added to a cooled (ice bath) 5% aqueous (Na$_2$CO$_3$) solution and the resulting mixture was extracted with ethyl acetate (3×50 mL). The combined organic layers were washed with water, dried over anhydrous (Na$_2$SO$_4$), and evaporated to provide 3 as dark yellow oil. Yield: 89%. $^1$H NMR (CDCl3, 600 MHz), δ (ppm): 1.88 (s, 6H), 3.56-3.58 (m, 4H), 3.63 (t, 6H), 3.70-3.71 (t, 2H), 4.27-4.28 (t, 2H)

Figure 64:
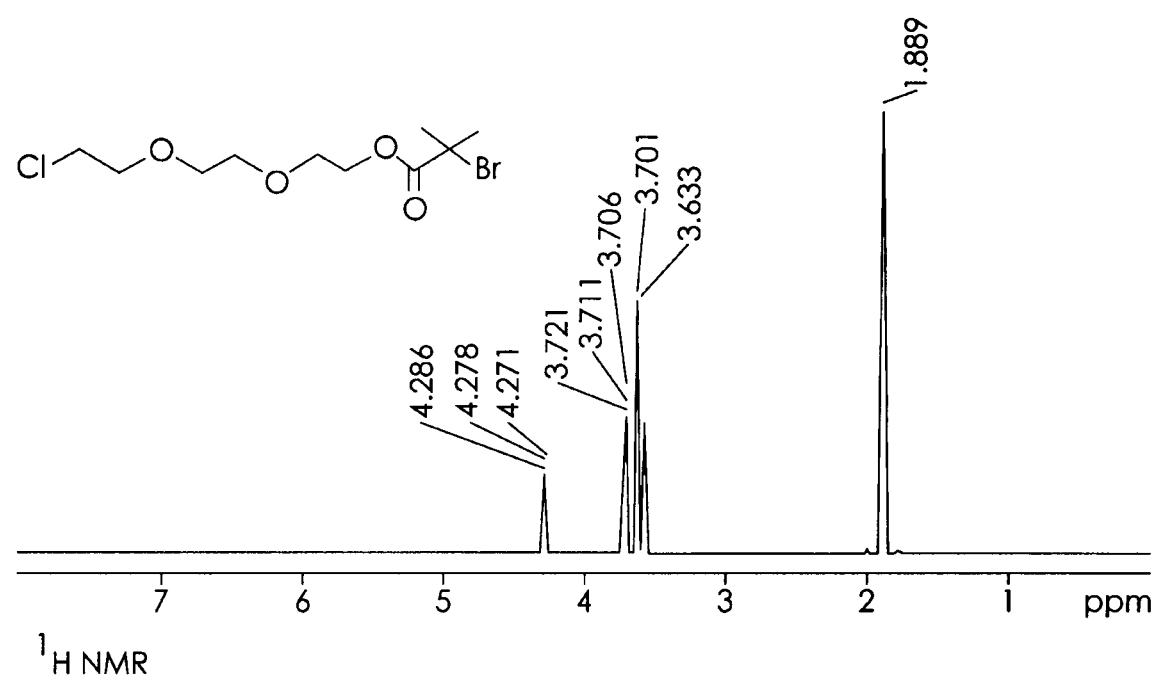

See FIG. 64 for $^1$H NMR.

28. Synthesis of Chloro Terminated Poly(tert-Butyl Acrylate)

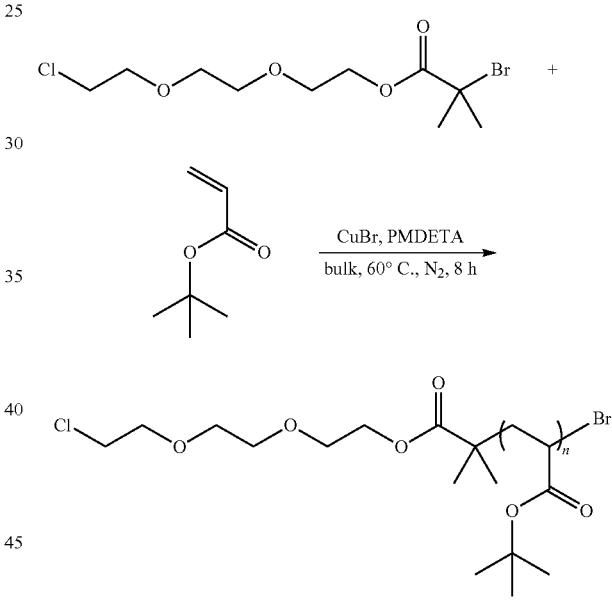

3-bromo-1-(2-(2-(2-chloroethoxy)ethoxy)ethoxy)-3-methylbutan-2-one (0.500 g, 1.57 mmol), tert-butyl acrylate (20.12 g, 157 mmol), and Cu(I)Br (0.563 g, 3.92 mmol) were added to a 100 ml round bottom flask. The reaction mix was freezed, pumped, and then thawed 3 times. After the solution thawed PMDETA (0.68 g, 3.92 ml) was added dropwise. The reaction was run under N$_2$. After 8 hours the reaction was stopped by placing the round bottom flask into a dry ice-acetone bath for 1 minute. The reaction mixture was diluted with THF and filtered. The excess copper was removed using Cuprisorb™. The polymer was purified by precipitation into a 20% MeOH—H$_2$O mixture. The final product was a white powder. Yield: 92%. $^1$H NMR (CDCl$_3$, 600 MHz), δ (ppm): 1.40-1.41 (s, 1644H), 1.18-1.81 (m, 76H), 2.18-2.54 (m, 160), 2.46-2.48 (t, 6H), 3.59-4.33 (m, 12H). FTIR (cm$^{-1}$): 3424, 2974, 2930, 1721. GPC (THF): Mn=14586, Mw=17186, PDI=1.17

Figure 65:
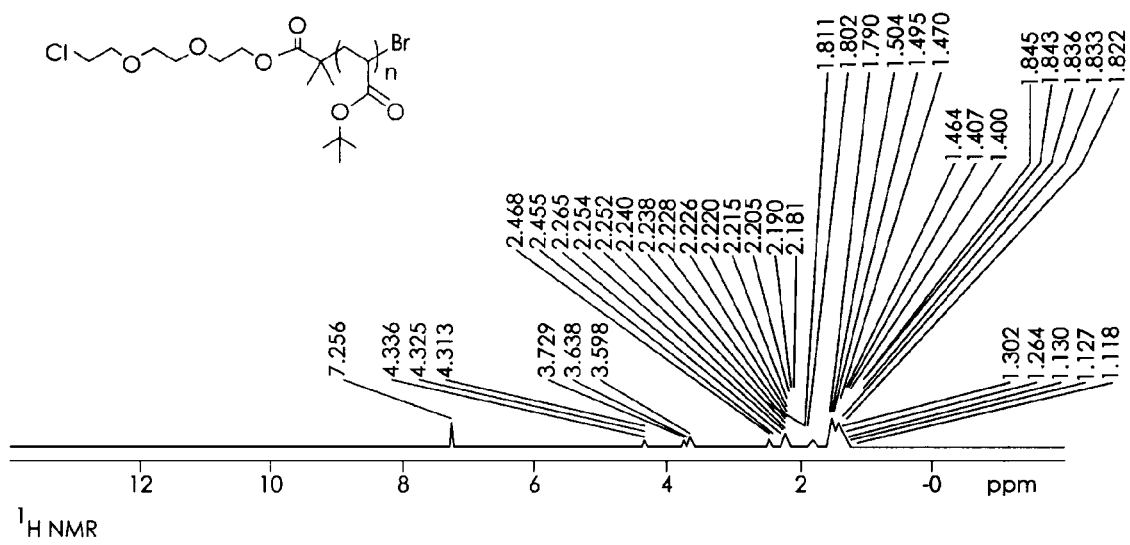

See FIG. 65 for $^1$H NMR.

29. Synthesis of Azide Terminated Poly(tert-Butyl Acrylate)

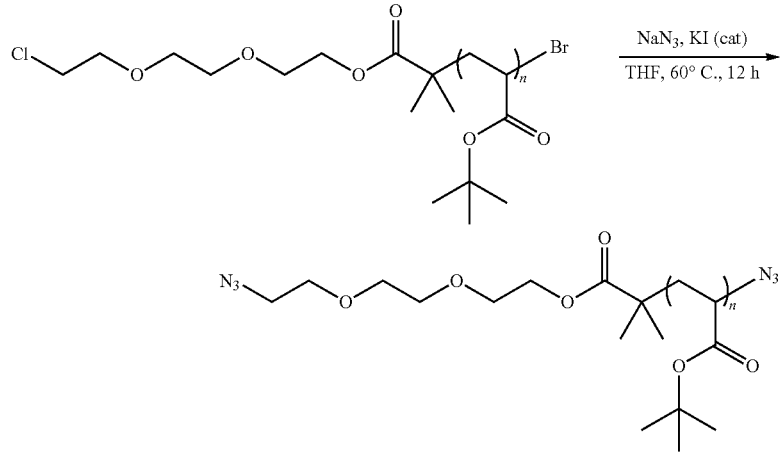

In a round bottom flask Chloro Terminated poly(tert-Butyl Acrylate) (0.5 g, 0.037 mmol), sodium azide (0.325 g, 5 mmol), and a pinch of KI were added to 10 ml of THF. The reaction mixture was stirred at 60° C. After 12 hours the reaction was stopped filtered and the solvent was evaporated. The polymer was purified by solvent extraction method using chloroform/water mixture. The organic layer was dried over $Na_2SO_4$ and the evaporation of the solvent yielded the product as white fluffy powder. Yield: 98%. $^1$H NMR (CDCl$_3$, 600 MHz), δ (ppm): 1.38-1.43 (s, 1644H), 1.49-1.53 (m, 76H), 1.806 (s), 2.21-2.46 (m, 160H), 2.49-2.51 (t, 6H), 3.63-4.35 (m, 12H). FTIR (cm$^{-1}$): 3434, 2982, 2930, 2108 (N$_3$), 1730. GPC (THF): Mn=14958, Mw=17150, PDI=1.14

Figure 66:
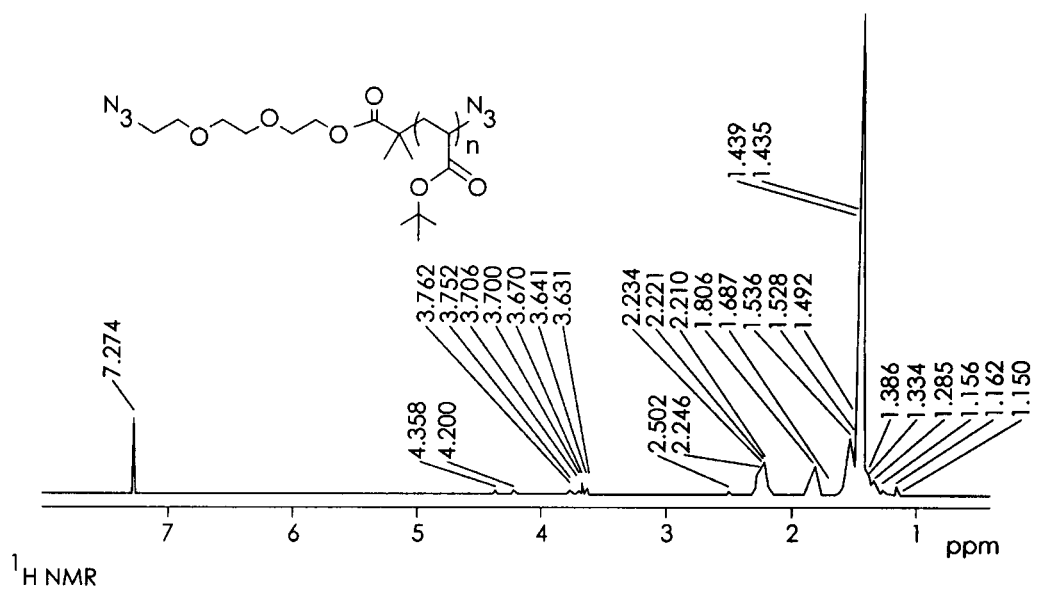

See FIG. 66 for $^1$H NMR.

30. Synthesis of Azide Terminated Poly(Acrylic acid)

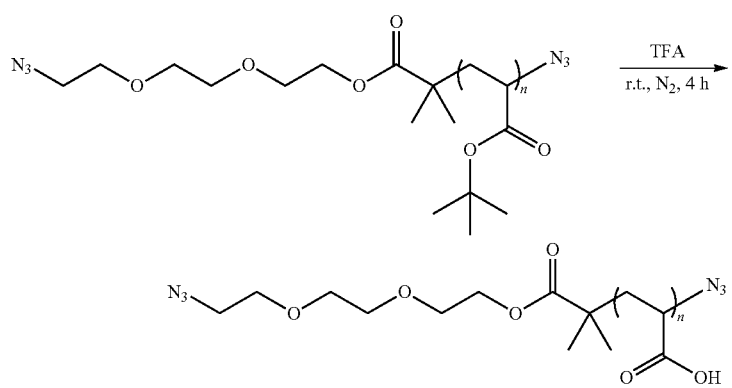

Trifluoro acetic acid (2 ml, 27 mmol) of was added dropwise to a round bottom flask containing poly(tert-Butyl Acrylate) (0.3 g, 0.02 mmol). The reaction was stirred under N$_2$ for 4 hours. The reaction mixture was dialyzed using 3500 MWCO membrane in distilled water with several exchanges and finally the lyophilization yielded the polymer as white powder. Yield: 97% 111 NMR (D$_2$O, 600 MHz), δ (ppm): 1.49-1.61 (m, 394H), 1.81 (s, 86H), 2.27 (s, 228H), 3.45-4.18 (m, 12H).

Figure 67:
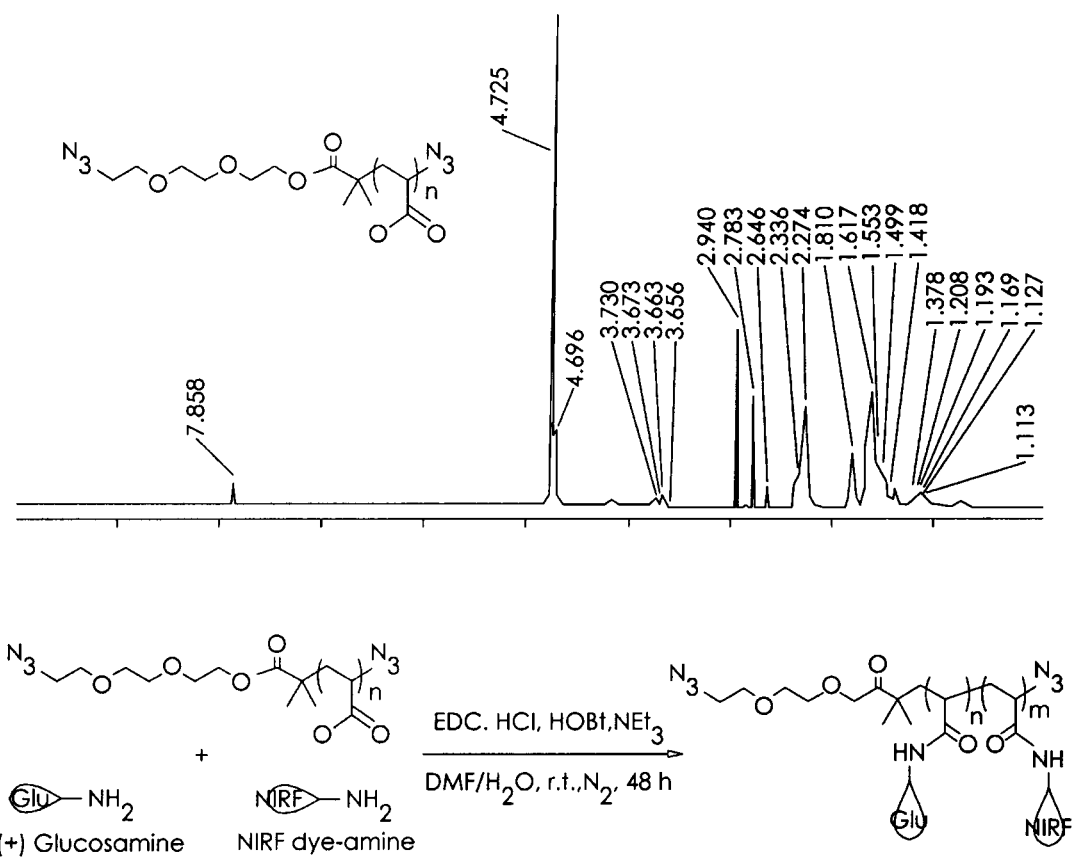

See FIG. 67 (top) for $^1$H NMR.

31. Synthesis of Azide Terminated Poly(Acrylic acid) containing Glucosamine and NIRF dye See FIG. 67 (bottom) for reaction scheme.

Azide terminated poly(acrylic acid) (72 mg, 0.003 mmol), NIRF dye (ADS832WS) (235 mg, 0.25 mmol), D(+)-Glucosamine (160 mg, 0.75 mmol), EDC.HCl (575 mg, 3.0 mmol) and HOBt (460 mg, 3.0 mmol) were dissolved in 10 ml of DMF in a round bottom flask and was degassed with N$_2$ and followed by dropwise addition of Et$_3$N (0.42 ml, 5 mmol). The reaction mixture was stirred at room temperature for 48 hours. The reaction mixture was dialyzed extensively using 3500 MWCO membrane and then purified by passing through a Sephadex LH20 column. Finally the product was isolated as black-colored fluffy powder after lyophilization. Yield: 76%. $^1$H NMR (D$_2$O, 600 MHz), δ (ppm): 1.03 (bs), 1.52-1.66 (bd), 1.76 (s), 2.01 (bs), 2.57 (s), 2.80 (s), 2.93 (bs), 3.59 (s), 3.65 (s), 3.75 (s), 5.09-5.22 (bm). FTIR (cm$^{-1}$): 3331, 2120 (N$_3$), 1636. GPC (H$_2$O): Mn=19469, Mw=25074, PDI=1.28.

Figure 68:
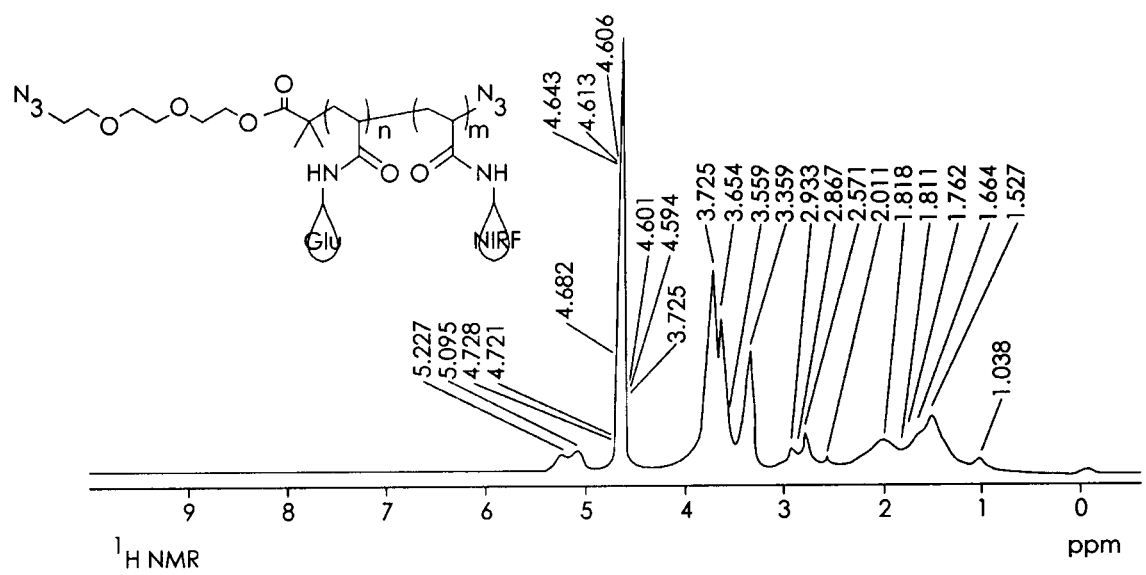

See FIG. 68 for $^1$H NMR.

32. Synthesis of 5-oxo-5-(prop-2-ynylamino)pentanoic acid

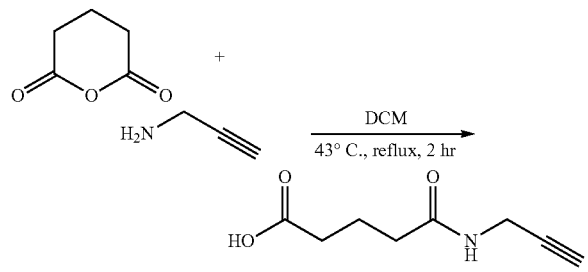

Glutaric anhydride (2.34 g, 0.2 mmol) was dissolved in 100 ml dry DCM in a round bottom flask and degassed with Ar. Propargyl amine (1.4 ml, 20 mmol) was added and the reaction mixture was refluxed at 43° C. for 2 hours and then stirred at room temperature for 2 hours. The solvent was evaporated and the crude product was purified by column chromatography using 95:5 $CH_2Cl_2$/MeOH. Yield: 75%. $^1$H NMR ($CDCl_3$, 200 MHz) δ (ppm): 1.67-1.76 (m, 2H), 2.09-2.26 (m, 4H), 2.38-2.41 (m, 1H), 3.75-3.76 (d, 2H).

Figure 69:
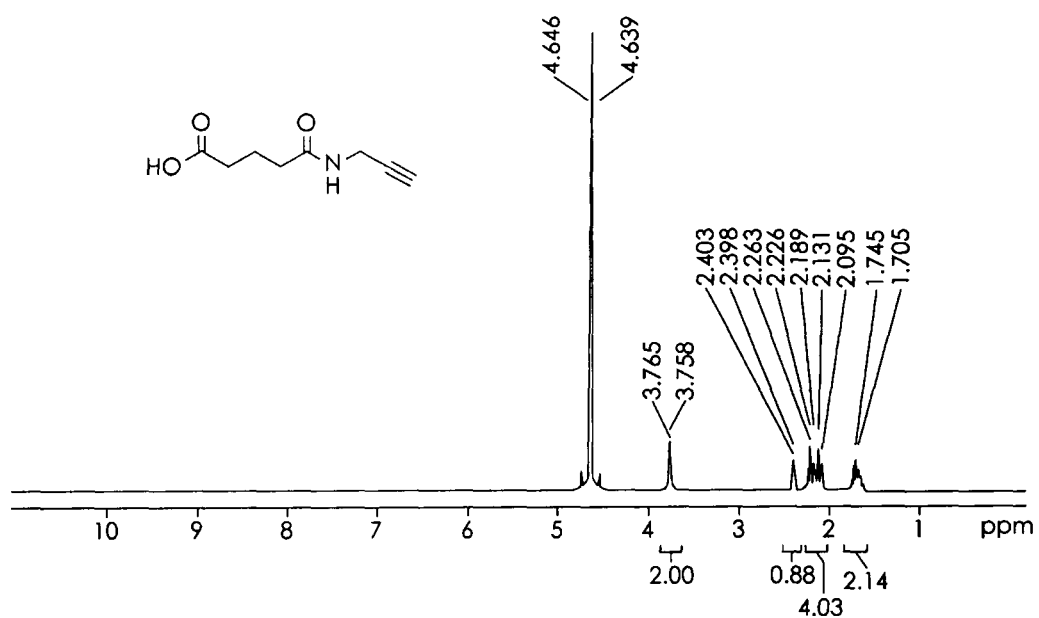

See FIG. 69 for $^1$H NMR.

33. Synthesis of 2,5-dioxopyrrolidin-1-yl-5-oxo-5-(prop-2-ynylamino)pentanoate (NHS-Alkyne)

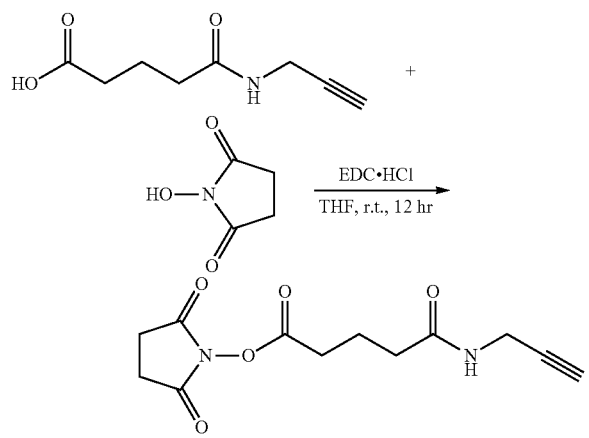

N-Hydroxy succinimide (0.93 g, 8.05 mmol), 5-oxo-5-(prop-2-ynylamino)pentanoic acid (1.01 g, 6 mmol) and EDC.HCl (1.22 g, 6.4 mmol) were dissolved in 50 ml of THF in a round bottom flask and degassed with Ar. The mixture was stirred at room temperature for 12 hrs and then the solvent was evaporated. Further the crude reaction mixture was dissolved in DCM and washed thoroughly with water, saturated $NahCO_3$, and brine. The organic layer was collected and dried over $Na_2SO_4$ and finally the solvent was evaporated to produce the product as white powder. Yield: 71%. $^1$H NMR ($CDCl_3$, 300 MHz) δ (ppm): 2.12-2.19 (m, 2H), 2.23-2.25 (t, 1H), 2.34-2.38 (t, 2H), 2.69-2.75 (m, 2H), 2.89 (s, 4H), 4.06-4.89 (m, 2H), 6.22 (bs, 1H).

Figure 70:
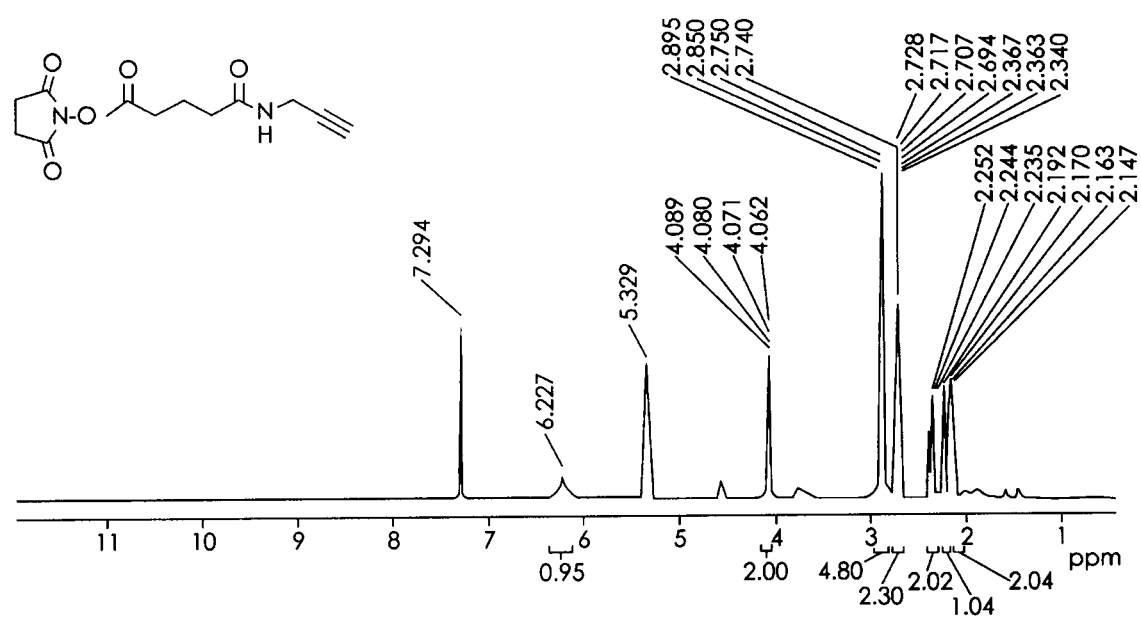

See FIG. 70 for $^1$H NMR.

34. UV-VIS-NIR and Fluorescence Spectroscopy of NIRF dye and Azide terminated poly(glucosamine)-poly(NIRF dye) copolymer 9

NIRF dye (ADS832WS) (2.8 mg) was dissolved in 10 ml of deionized water to prepare a stock solution of 3 μM. Azide terminated poly(glucosamine)-poly(NIRF dye) copolymer 9 (11.7 mg; 5 dye molecule per polymer chain) was dissolved in 10 ml of deionized water to prepare a solution of 0.3 mM of effective dye concentration. The stock solution of NIRF dye was further diluted to 0.3 μM. The UV-VIS-NIR spectra were obtained on an Agilent Technologies 845×UV-Vis System using deionized water as blank. The fluorescence spectra of both the dye and the dye incorporated copolymer 9 were obtained on JobinYvon Horiba FluoroMax-3 instrument using the solutions containing 0.3 μM effective dye concentration.

35. Test of the Utility of Protein-Polymer Hybrid in Non Invasive Imaging in Mice Each of two female, six months old mice were injected with 200 μl of the NIRF dye, and the biotin terminated poly(glucosamine)-poly(NIRF dye) copolymer 6 (0.2 mM effective dye concentration in both cases) via the tail vein. Each mouse was then anaesthetized using mixture of 15 μL Xylezene mixed with 54 μL Ketamine to reach a dose of 10 mg/kg body weight of Xylezene, and 90 mg/kg bodyweight of Ketamine per mouse, and then scanned using a Odyssey scanner (Near IR) at wavelength 800 nm. To investigate the extent of fluorescence, and the extent of catabolism of the polymer the mice were scanned after one hour and four hours. Another female six months old mouse (control mouse) was anaesthetized with the same anesthetic mixture and then scanned to eliminate background fluorescence.

36. Detection of Binding of Biotinylated Copolymers to Streptavidin Coated Wells Control poly(glucosamine)-poly(NIRF dye) copolymer, biotin terminated poly(acrylic acid)-poly(NIRF Dye) polymer 6a, and biotin terminated poly(glucosamine)-poly(NIRF dye) copolymer 6. All samples were prepared at a starting effective molar dye concentration of 0.2 mM in PBS (pH=7.4), then each of the three samples were successively diluted ten-fold to final concentrations of 0.02, $2.0 \times 10^{-3}$, $2.0 \times 10^{-4}$ mM. 50 μl of each solution was then added to the wells, and incubated overnight at 4 degrees Celsius. Then the wells were washed four times with PBS containing 0.05% Tween-20. Finally, the wells were then visualized using the Odyssey imaging system (LI-COR, Lincoln, Nebr.) at 800 nm.

37. Cell Surface Imaging Using Retinal Epithelial Cells

Retinal pigment epithelial cells were divided onto four wells, and then allowed to grow for three days with regular feeding; the cells were then fixed using 2% PFA, then rinsed three times for five minutes each using PBS (pH=7.4). The nonspecific binding sites were then blocked using a blocking buffer and incubated for overnight. The blocking buffer was then removed, and well (a) only was incubated with the primary antibody, and incubated for overnight at 4° C. The primary antibody was then rinsed three times five minutes each, and then the secondary antibody was added to wells (a & b), and incubated for overnight at 4° C. Rinsing was performed for the excess secondary antibody using the same technique used for the primary antibody, then 500 µl of Avidin (1 mg/ml) was added to each of wells (a,b & c) and incubate for overnight at 4° C., and excess of avidin was washed off with PBS (pH=7.4) three times five minutes each. Finally 500 µl of poly(glucosamine)-poly(NIRF dye) copolymer 6 (0.1 mg/ml) was added to each of the wells (a,b,c & d) and incubated for two hours at 37° C. at a controlled temperature chamber. Excess polymer was washed off using PBS (pH=7.4) three times five minutes each, fresh PBS was then added to the wells and scanned using Odyssey imaging system (LI-COR, Lincoln, Nebr.) with detection in the NW region at 800 nm.

Blocking Solution:
4% Normal goat serum (NGS)
2% BSA
0.05% Tween 20
Antibody Dilution Buffer:
2% NGS
1% BSA
0.05% Tween 20
50% blocking buffer in PBS was used to prepare the Antibody Dilution Buffer Preparation of Antibodies Primary Antibody:
(2B-α5 Rabbit polyclonal IgG)
1:200 preparation of the antibody in 2% ADB without Tween (not to permeate the cells).
Secondary Antibody:
(GtxRb secondary Lot: 0507003644)
1:200 preparation of the antibody in 2% ADB without Tween (not to permeate the cells).

REFERENCES CONSULTED

1. Harris, J. M. "Poly(ethylene glycol) chemistry; Biotechnical and Biomedical Applications." Edited by Harrris, J. Milton, Plenum Press, New York. 1992.
2. Nicolas, J.; Mantovani, G.; Haddleton, D. M. "Living Radical Polymerization as a Tool for the Synthesis of Polymer-Protein/Peptide Bioconjugates." Macromol. Rapid Commun., 2007, 28, 1083-1111.
3. Raja, K. S.; Wang, Q. "Bionanoparticles." Dekker Encyclopedia of Nanoscience and Nanotechnology Edited by Prof. James A. Schwarz, Dr. Cristian Contescu, and Dr. Karol Putyera. Marcel Dekker, 2004, 330-331.
4. Vriezema, D. M.; Aragones, M. C.; Elemans, J. A. A. W.; Cornelissen, J. J. L. M.; Rowan, A. E.; Nolte, R. J. M. "Self-Assembled Nanoreactors." Chemical Reviews, 2005, 105, 1445-1489.
5. Douglas, T.; Young, M. "Viruses: Making Friends with Old Foes." Science, 2006, 312, 873-875.
6. Wang, J. S.; Matyjaszewski, K. "Controlled"/"living" radical polymerization. Atom Transfer Radical Polymerization in the presence of transition-metal complexes." J. Am. Chem. Soc., 1995, 117, 5614-5615.
7. Perrier, S.; Takolpuckdee, P. "Macromolecular design via reversible addition-fragmentation chain transfer (RAFT)/ xanthates (MADIX) polymerization." Journal of Polymer Science: Part A: Polymer Chemistry, 2005, 43, 5347-5393.
8. Kulkarni, S.; Schilli, C.; Grin, B.; Mueller, A. H. E.; Hoffman, A. S.; Stayton, P. S. "Controlling the Aggregation of Conjugates of Streptavidin with Smart Block Copolymers Prepared via the RAFT Copolymerization Technique." Biomacromolecules, 2006, 7, 2736-2741.
9. Sengupta, S.; Raja, K. S.; Kaltgrad, E.; Strable, E.; Finn, M. G. "Virus-glycopolymer conjugates by copper(I) catalysis of atom transfer radical polymerization and azide-alkyne cycloaddition." Chem. Comm., 2005, 34, 4315-4317.
10. Hou, S.; Sun, X.-L.; Dong, C.-M.; Chaikof, E. L. "Facile Synthesis of Chain-End Functionalized Glycopolymers for Site-Specific Bioconjugation." Bioconjugate Chemistry, 2004, 15, 954-959.
11. Bontempo, D.; Maynard, H. D. "Streptavidin as a Macroinitiator for Polymerization: In Situ Protein-Polymer Conjugate Formation." J. Am. Chem. Soc., 2005, 127, 6508-6509.
12. Lele, B. S.; Murata, H.; Matyjaszewski, K.; Russell, A. J. "Synthesis of Uniform Protein-Polymer Conjugates." Biomacromolecules, 2005, 6, 3380-3387.
13. Ayres, L.; Vos, M. R. J.; Adams, P. J. H. M.; Shklyarevskiy, I. O.; vanHest, J. C. M. "Elastin-Based Side-Chain Polymers Synthesized by ATRP." Macromolecules, 2003, 36, 5967-5973.
14. Nicolas, J.; Khoshdel, E.; Haddleton, D. M. "Bioconjugation onto biological surfaces with fluorescently labeled polymers." Chem. Comm., 2007, 17, 1722-1724.
15. Aggarwal, B. B.; Shishodia, S. "Molecular targets of dietary agents for prevention and therapy of cancer." Biochemical Pharmacology, 2006, 71, 1397-1421.
16. Leyon, P. V.; Kuttan, G. "Studies on the role of some synthetic curcuminoid derivatives in the inhibition of tumour specific angiogenesis." Journal of Experimental & Clinical Cancer Research, 2003, 22, 77-83.
17. Nurfina, A. N.; Reksohadiprodjo, M. S.; Timmerman, H.; Jenie, U. A.; Sugiyanto, D.; Van Der Goot, H. "Synthesis of some symmetrical curcumin derivatives and their antiinflammatory activity." Euro. J. Med. Chem., 1997, 32, 321-328.
18. Yang, F.; Lim, G. P.; Begum, A. N.; Ubeda, O. J.; Simmons, M. R.; Ambegaokar, S. S.; Chen, P. P.; Kayed, R.; Glabe, C. G.; Frautschy, S. A.; Cole, G. M. "Curcumin Inhibits Formation of Amyloid Oligomers and Fibrils, Binds Plaques, and Reduces Amyloid in Vivo." Journal of Biological Chemistry, 2005, 280, 5892-5901.
19. Raja, K. S.; Banerjee, P., Lamerouex, W., Shi, W. "Novel Curcumin and Tetrahydrocurcumin derivatives." patent application number 07/21805.
20. Shi, W.; Dolai, S.; Rizk, S.; Hussain, A.; Tariq, H.; Averick, S.; L'Amoreaux, W.; El Idrissi, A.; Banerjee, P.; Raja, K. S. "Synthesis of monofunctional curcumin derivatives, clicked curcumin dimer and a PAMAM dendrimer curcumin conjugate for therapeutic applications." Organic Letters, 2007, 9, 5461-5464.
21. Raja, K. S.; Wang, Q.; Gonzalez, M. J.; Manchester, M.; Johnson, J. E.; Finn, M. G. "Hybrid Virus-Polymer Materials Synthesis and Properties of PEG-Decorated Cowpea Mosaic Virus." Biomacromolecules, 2003, 4, 472-476.
22. Wang, Q.; Raja, K. S.; Lin, T.; Janda, K. D.; Johnson, J. E.; Finn, M. G. "Blue Fluorescent Antibodies as reporters of steric accessibility in Virus conjugates." Bioconjugate Chemistry, 2003, 14, 38-43.
23. Schlick, T. L.; Ding, Z.; Kovacs, E. W.; Francis, M. B. "Dual-surface modification of the Tobacco mosaic virus." J. Am. Chem. Soc., 2005, 127, 3718-3723.
24. Wang, Q.; Lin, T.; Tang, L.; Johnson, J. E.; Finn, M. G. "Icosahedral virus particles as addressable nanoscale building blocks." Angew. Chem. Int. Ed, 2002, 41, 459-462.
25. Raja, K. S.; Wang, Q.; Finn, M. G. "Icosahedral virus particles as polyvalent carbohydrate display platforms." Chem. BioChem., 2003, 4, 1348-1351.

26. Anderson, E. A.; Isaacman, S.; Peabody, D. S.; Wang, E. Y.; Canary, J. W.; Kirshenbaum, K. "Viral Nanoparticles Donning a Paramagnetic Coat: Conjugation of MRI Contrast Agents to the MS2 Capsid." Nano Letters, 2006, 6, 1160-1164.
27. Flenniken, M. L.; Liepold, L. O.; Crowley, B. E.; Willits, D. A.; Young, M. J.; Douglas, T. "Selective attachment and release of a chemotherapeutic agent from the interior of a protein cage architecture." Chem. Comm., 2005, 4, 447-449.
28. Raja, K. S.; McDonald, R.; Tuck, S.; Rodriguez, R.; Milley, B.; Traquina, P. "One-Pot Synthesis, Purification, and Formulation of Bionanoparticle-CpG Oligodeoxynucleotide Hepatitis B Surface Antigen Conjugate Vaccine via Tangential Flow Filtration." Bioconjugate Chem., 2007, 18, 285-288.
29. Ehrlich, P. "The Collected Papers of Paul Ehrlich." Edited by F. Himmelweit, Pergamon, London. 1960.
30. Rick, M. "The next wave in Biopharmaceuticals." Chem. Eng. News, 2005, 83, 16-19.
31. Hata, K. "Efficacy of Mylotarg for acute myeloid lukhemia." Annual Review Ketsueki, 2006, 114-123.
32. Wu, A. M.; Senter, P. D. "Arming antibodies: prospects and challenges for immunoconjugates." Nature Biotechnology, 2005, 23, 1137-1146.
33. Hermenson, G. T. "Bioconjugate Techniques." $2^{nd}$ Ed. ed., Academic Press, San Diego, Calif., 2008.
34. Cheng, Z.; Levi, J.; Xiong, Z.; Gheysens, O.; Keren, S.; Chen, X.; Gambhir, S. S. "Near-Infrared Fluorescent Deoxyglucose Analogue for Tumor Optical Imaging in Cell Culture and Living Mice." Bioconjugate Chemistry, 2006, 17, 662-669.
35. Kovar, M., Strohalm, J., Etrych, T.; Ulbrich, K.; Rihova, B. "Star Structure of Antibody-Targeted HPMA Copolymer-Bound Doxorubicin: A Novel Type of Polymeric Conjugate for Targeted Drug Delivery with Potent Antitumor Effect." Bioconjugate Chemistry, 2002, 13, 206-215.
36. Savage, M. D. "Avidin-Biotin Chemistry: A Handbook." Rockford, Ill.: Pierce Chemical Company, 1992.
37. Geng, J.; Mantovani, G.; Tao, L.; Nicolas, J.; Chen, G.; Wallis, R.; Mitchell, D. A.; Johnson, B. R.; Evans, S. D.; Haddleton, D. M. "Site-directed conjugation of "clicked" glycopolymers to form glycoprotein mimics: binding to mammalian lectin and induction of immunological function." J. Am. Chem. Soc., 2007, 129, 15156-63.
38. Wadia, J. S.; Steven, F.; Dowdy, Z. "Protein transduction technology." Current Opinion in Biotechnology, 2002, 13, 52-56.
39. Toublan, F. J. J.; Boppart, S.; Suslick, K. S. "Tumor Targeting by Surface-Modified Protein Microspheres." J. Am. Chem. Soc., 2006, 128, 3472-3473.
40. Vazquez-Dorbatt, V.; Maynard, H. D. "Biotinylated glycopolymers synthesized by atom transfer radical polymerization." Biomacromolecules, 2006, 7, 2297-302.
41. Luxenhofer, R.; Jordan, R. "Click Chemistry with Poly (2-oxazoline)s." Macromolecules, 2006, 39, 3509-3516.
42. Sen Gupta, S.; Kuzelka, J.; Singh, P.; Lewis, W. G.; Manchester, M.; Finn, M. G. "Accelerated bioorthogonal conjugation: a practical method for the ligation of diverse functional molecules to a polyvalent virus scaffold." Bioconjug. Chem., 2005, 16, 1572-9.

We claim:

1. A polymer having the formula:

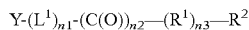

wherein:
Y represents:

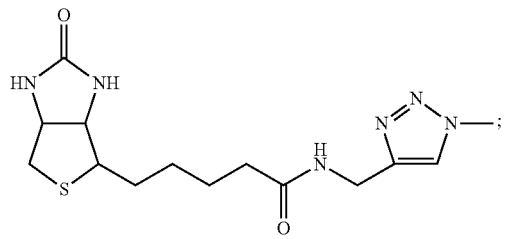 [SMILES: Cn1cc(CNC(=O)CCCCC2SCC3NC(=O)NC32)nn1]

$L^1$ represents —(CH$_2$CH$_2$O—)$_p$—C(O)—C(CH$_3$)$_2$— or —(OCH$_2$CH$_2$—)$_p$—C(O)—C(CH$_3$)$_2$— wherein p represents a minimum of 1 and a maximum of 20,

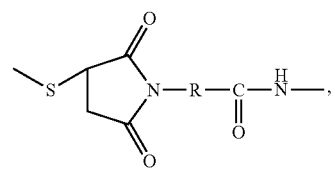

or

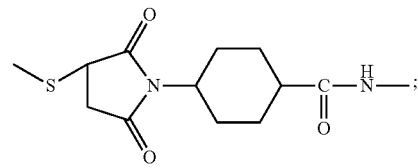

n1 represents 0 or 1;
n2 represents 0 or 1;
$R^1$ independently represents:

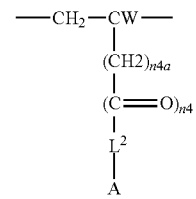

W independently represents —H, —CH$_3$, —COOH, or —CH$_2$COOH;
n4a independently represents 0 or 1;
n4 independently represents 0 or 1;
$L^2$ represents —NH—;
R represents:
(i) C$_1$-C$_{12}$ alkyl optionally substituted with one or more hydroxyl or oxo substituents, and wherein one or more carbon atoms in the alkyl chain is optionally substituted with a heteroatom selected from the group consisting of —O—, —S—, and —NH—; (ii) phenyl or biphenyl, (iii) a carbocyclic non-aromatic ring having 5-7 carbon atoms; (iv) an aromatic heterocyclic ring having five or six atoms wherein at least one of the ring carbon atoms is substituted by a heteroatom selected from the group consisting of O, S, or NH, and (v) a non-aromatic heterocyclic ring having 5-7 carbon atoms wherein at least one of the ring carbon atoms is substituted by a heteroatom selected from the group consisting of O, S, or NH;

A represents $(A^1)_n$ and $(A^2)_m$;

$A^1$ represents glucose;

$A^2$ represents NIRF dye;

n and m independently represent 2 to about 60;

n3 represents n+m; and $R^2$ represents H, an a straight chain or branched alkyl group having 1-6 carbon atoms, Cl or Br.

2. A polymer according to claim 1, wherein $L^1$ results from the chain initiation step of the polymerization process.

3. A polymer according to claim 1, wherein p represents 2-4.

4. A polymer according to claim 1, wherein p represents 3.

5. A polymer according to claim 1, wherein R represents —(CH$_2$CH$_2$O—)$_p$— or —(OCH$_2$CH$_2$—)$_p$—, and p represents a minimum of 1 and a maximum of 20.

6. A polymer according to claim 1, wherein Y is replaced by E-X, and wherein E represents a protein or a peptide having up to twelve amino acids, and
X is 7. A polymer according to claim 6, wherein E is a chromophore, a radioactive label, a biologically active molecule or an MRI imaging agent.

8. A polymer according to claim 6, wherein E is a targeting protein or peptide.

9. A polymer according to claim 8, wherein E is selected from the group consisting of an antibody, HIV Tat, RGD peptides, avidin, and streptavidin.

10. A polymer according to claim 9, wherein E is a primary, secondary, or monoclonal antibody.

11. A polymer according to claim 9, wherein the antibody is genetically or chemically modified.

12. A polymer according to claim 11, wherein the antibody is chimerized or humanized.

13. A polymer according to claim 6, wherein E is an enzyme.

14. A polymer according to claim 13, wherein the enzyme is horseradish peroxidase, beta-galactosidase or luciferase.

15. A polymer according to claim 6, wherein E is a bio-nanoparticle.

16. A polymer according to claim 15, wherein the bionanoparticle is a virus, ferritin, or apoferritin.

17. A polymer according to claim 16, wherein the bionanoparticle is a virus, and the virus is tobacco mosaic virus or cauliflower mosaic virus.

18. A polymer according to claim 16, wherein the virus is genetically or chemically modified.

19. A polymer according to claim 18, wherein the virus is an empty capsid.

20. A polymer according to claim 6, wherein E is a protein selected from the group consisting of Protein A, Protein G, Protein L, BSA, and ovalbumen.

21. A polymer according to claim 6, wherein E is hepatitis B surface antigen.

22. A polymer according to claim 6, wherein E is a therapeutic protein.

23. A polymer according to claim 22, wherein the therapeutic protein is erythropoietin, human growth hormone, and insulin.
24. A polymer according to claim 1, wherein n is 30 to 60 and m is 2 to 20.
25. A polymer represented by the following formula:
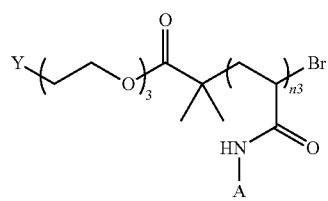
wherein:
Y represents:
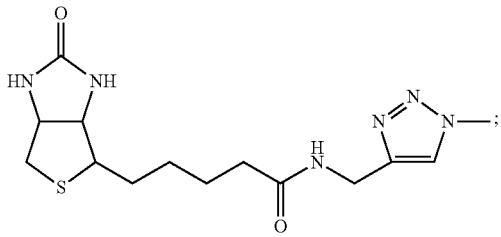 [SMILES: Cn1cc(CNC(=O)CCCCC2SCC3NC(=O)NC32)nn1]
A represents $(A^1)_n$ and $(A^2)_m$;
$A^1$ represents glucose;
$A^2$ represents NIRF dye;
n is 30 to 60;
m is 2 to 20; and
n3 represents n+m.
* * * * *

UNITED STATES PATENT AND TRADEMARK OFFICE
CERTIFICATE OF CORRECTION

PATENT NO. : 9,242,010 B2
APPLICATION NO. : 12/992854
DATED : January 26, 2016
INVENTOR(S) : Raja et al.

Page 1 of 1

It is certified that error appears in the above-identified patent and that said Letters Patent is hereby corrected as shown below:

In the specification,

Column 44, line 42

Now reads: "See FIG. 25 for H NMR and $^{13}$C NMR."

Should read: -- See FIG. 25 for $^1$H NMR and $^{13}$C NMR. --

Column 52, line 43

Now reads: "The mixture was stirred at mom temperature for 5h."

Should read: -- The mixture was stirred at room temperature for 5h. --

Signed and Sealed this
Twenty-third Day of August, 2016

Michelle K. Lee
*Director of the United States Patent and Trademark Office*